US009000127B2

(12) United States Patent
Stennicke et al.

(10) Patent No.: US 9,000,127 B2
(45) Date of Patent: Apr. 7, 2015

(54) ANTIBODIES THAT BIND AND BLOCK TRIGGERING RECEPTOR EXPRESSED ON MYELOID CELLS-1 (TREM-1)

(71) Applicant: Novo Nordisk A/S, Bagsvaerd (DK)

(72) Inventors: Vibeke Westphal Stennicke, Kokkedal (DK); Christine Brender Read, Soeborg (DK); Susanne Nedergaard Grell, Soeborg (DK); Charlotte Wiberg, Bjarred (SE); Rune Salbo, Hvidovre (DK); Anette Henriksen, Alleroed (DK); Soeren Padkjaer, Vaeloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 102 days.

(21) Appl. No.: 13/690,748

(22) Filed: Nov. 30, 2012

(65) Prior Publication Data

US 2013/0211050 A1 Aug. 15, 2013

Related U.S. Application Data

(60) Provisional application No. 61/598,968, filed on Feb. 15, 2012, provisional application No. 61/599,447, filed on Feb. 16, 2012, provisional application No. 61/672,799, filed on Jul. 18, 2012, provisional application No. 61/674,434, filed on Jul. 23, 2012.

(30) Foreign Application Priority Data

| Feb. 15, 2012 | (EP) | 12155641 |
| Mar. 12, 2012 | (EP) | 12158974 |
| Jul. 18, 2012 | (EP) | 12176892 |

(51) Int. Cl.
| *A61K 39/395* | (2006.01) |
| *C07K 16/00* | (2006.01) |
| *C07K 16/18* | (2006.01) |
| *C07K 16/28* | (2006.01) |
| *A61K 39/00* | (2006.01) |

(52) U.S. Cl.
CPC .............. *C07K 16/28* (2013.01); *C07K 16/2803* (2013.01); *C07K 16/2896* (2013.01); *A61K 2039/505* (2013.01); *C07K 2317/24* (2013.01); *C07K 2317/33* (2013.01); *C07K 2317/34* (2013.01); *C07K 2317/76* (2013.01); *C07K 2317/92* (2013.01); *C07K 2317/55* (2013.01); *C07K 2317/565* (2013.01); *C07K 2317/567* (2013.01); *C07K 2317/74* (2013.01)

(58) Field of Classification Search
None
See application file for complete search history.

(56) References Cited

U.S. PATENT DOCUMENTS

| 4,444,887 | A | 4/1984 | Hoffmann |
| 4,522,811 | A | 6/1985 | Eppstein et al. |
| 4,676,980 | A | 6/1987 | Segal et al. |
| 4,683,195 | A | 7/1987 | Mullis et al. |
| 4,683,202 | A | 7/1987 | Mullis |
| 4,716,111 | A | 12/1987 | Osband et al. |
| 4,736,866 | A | 4/1988 | Leder et al. |
| 4,741,900 | A | 5/1988 | Alvarez et al. |
| 4,816,397 | A | 3/1989 | Boss et al. |
| 4,816,567 | A | 3/1989 | Cabilly et al. |
| 4,870,009 | A | 9/1989 | Evans et al. |
| 4,873,191 | A | 10/1989 | Wagner et al. |
| 4,873,316 | A | 10/1989 | Meade et al. |
| 4,946,778 | A | 8/1990 | Ladner et al. |
| 4,980,286 | A | 12/1990 | Morgan et al. |
| 4,987,071 | A | 1/1991 | Cech et al. |
| 5,116,742 | A | 5/1992 | Cech et al. |
| 5,223,409 | A | 6/1993 | Ladner et al. |
| 5,225,539 | A | 7/1993 | Winter |
| 5,258,498 | A | 11/1993 | Huston et al. |
| 5,272,057 | A | 12/1993 | Smulson et al. |
| 5,272,071 | A | 12/1993 | Chappel |
| 5,283,317 | A | 2/1994 | Saifer et al. |
| 5,328,470 | A | 7/1994 | Nabel et al. |
| 5,403,484 | A | 4/1995 | Ladner et al. |
| 5,413,923 | A | 5/1995 | Kucherlapati et al. |
| 5,420,526 | A | 5/1995 | Fensch |
| 5,424,286 | A | 6/1995 | Eng |
| 5,427,908 | A | 6/1995 | Dower et al. |
| 5,436,146 | A | 7/1995 | Shenk et al. |
| 5,459,039 | A | 10/1995 | Modrich et al. |
| 5,474,981 | A | 12/1995 | Leder et al. |
| 5,498,531 | A | 3/1996 | Jarrell |
| 5,516,637 | A | 5/1996 | Huang et al. |
| 5,530,101 | A | 6/1996 | Queen et al. |

(Continued)

FOREIGN PATENT DOCUMENTS

| CA | 2342376 A1 | 9/2002 |
| EP | 239400 A2 | 9/1987 |

(Continued)

OTHER PUBLICATIONS

MacCallum et al. (1996). J. Mol. Biol. 262:732-745.*

(Continued)

*Primary Examiner* — Christine J Saoud
*Assistant Examiner* — Jon M Lockard
(74) *Attorney, Agent, or Firm* — Nonna G. Akopyan; Reza Green; Richard W. Bork

(57) ABSTRACT

The invention relates to antibodies that are capable of specifically binding TREM-1 and preventing the activation of TREM-1, a protein expressed on monocytes, macrophages and neutrophils. Such antibodies find utility in the treatment of individuals with an inflammatory disease, such as rheumatoid arthritis and inflammatory bowel disease.

14 Claims, 16 Drawing Sheets

(56) References Cited

U.S. PATENT DOCUMENTS

| | | |
|---|---|---|
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,807,715 A | 9/1998 | Morrison et al. |
| 5,814,318 A | 9/1998 | Lonberg et al. |
| 5,821,047 A | 10/1998 | Garrard et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 6,420,526 B1 | 7/2002 | Ruben et al. |
| 6,504,010 B1 | 1/2003 | Wang et al. |
| 6,509,448 B2 | 1/2003 | Wang et al. |
| 6,858,204 B2 | 2/2005 | Henderson et al. |
| 6,878,687 B1 | 4/2005 | Ruben et al. |
| 8,013,116 B2 | 9/2011 | Faure et al. |
| 2002/0128444 A1 | 9/2002 | Gingras et al. |
| 2002/0172952 A1 | 11/2002 | Henderson et al. |
| 2002/0197669 A1 | 12/2002 | Bangur et al. |
| 2003/0049618 A1 | 3/2003 | Ruben et al. |
| 2003/0054363 A1 | 3/2003 | Henderson et al. |
| 2003/0077282 A1 | 4/2003 | Bigler et al. |
| 2003/0134283 A1 | 7/2003 | Peterson et al. |
| 2003/0165875 A1 | 9/2003 | Colonna et al. |
| 2003/0166068 A1 | 9/2003 | Ashida et al. |
| 2003/0170255 A1 | 9/2003 | Watanabe et al. |
| 2003/0175858 A1 | 9/2003 | Ruben et al. |
| 2003/0211510 A1 | 11/2003 | Henderson et al. |
| 2004/0236092 A1 | 11/2004 | Dziarski et al. |
| 2005/0255114 A1 | 11/2005 | Labat et al. |
| 2006/0183125 A1 | 8/2006 | Mariani et al. |
| 2009/0092582 A1 | 4/2009 | Bogin et al. |
| 2010/0310560 A1 | 12/2010 | Colonna et al. |

FOREIGN PATENT DOCUMENTS

| | | |
|---|---|---|
| EP | 264166 A1 | 4/1988 |
| EP | 439098 A2 | 7/1991 |
| EP | 519596 A1 | 12/1992 |
| EP | 592106 A1 | 4/1994 |
| EP | 1022286 A1 | 7/2000 |
| EP | 1498424 A2 | 1/2005 |
| WO | 88/09810 A1 | 12/1988 |
| WO | 89/10134 A1 | 11/1989 |
| WO | 90/02809 A1 | 3/1990 |
| WO | 90/11354 A1 | 10/1990 |
| WO | 91/01140 A1 | 2/1991 |
| WO | 91/06667 A1 | 5/1991 |
| WO | 91/09967 A1 | 7/1991 |
| WO | 91/10737 A1 | 7/1991 |
| WO | 91/10741 A1 | 7/1991 |
| WO | 92/00968 A1 | 1/1992 |
| WO | 92/01047 A1 | 1/1992 |
| WO | 92/06180 A1 | 4/1992 |
| WO | 92/18619 A1 | 10/1992 |
| WO | 92/20316 A2 | 11/1992 |
| WO | 92/22324 A1 | 12/1992 |
| WO | 92/22635 A1 | 12/1992 |
| WO | 93/04169 A1 | 3/1993 |
| WO | 93/11236 A1 | 6/1993 |
| WO | 93/14188 A1 | 7/1993 |
| WO | 93/20221 A1 | 10/1993 |
| WO | 93/21232 A1 | 10/1993 |
| WO | 94/08598 A1 | 4/1994 |
| WO | 94/10300 A1 | 5/1994 |
| WO | 9412649 A2 | 6/1994 |
| WO | 94/16101 A2 | 7/1994 |
| WO | 95/15982 A2 | 6/1995 |
| WO | 95/20401 A1 | 8/1995 |
| WO | 96/33735 A1 | 10/1996 |
| WO | 96/34096 A1 | 10/1996 |
| WO | 97/07668 A1 | 3/1997 |
| WO | 97/07669 A1 | 3/1997 |
| WO | 98/08871 | 3/1998 |
| WO | 98/16654 A1 | 4/1998 |
| WO | 98/24893 A2 | 6/1998 |
| WO | 98/39446 A2 | 9/1998 |
| WO | 98/39448 A2 | 9/1998 |
| WO | 98/46645 A2 | 10/1998 |
| WO | 98/50433 A2 | 11/1998 |
| WO | 9902686 A1 | 1/1999 |
| WO | 00/00610 A2 | 1/2000 |
| WO | 01/53312 A1 | 7/2001 |
| WO | 01/90304 A2 | 11/2001 |
| WO | 02/058721 A1 | 8/2002 |
| WO | 03/011213 A2 | 2/2003 |
| WO | 03/025138 A2 | 3/2003 |
| WO | 03/030835 A2 | 4/2003 |
| WO | 03029401 A2 | 4/2003 |
| WO | 03/037267 A2 | 5/2003 |
| WO | 03/060071 A2 | 7/2003 |
| WO | 03/061712 A1 | 7/2003 |
| WO | 03/080667 A2 | 10/2003 |
| WO | 2004/020591 A2 | 3/2004 |
| WO | 2004/081233 A1 | 9/2004 |
| WO | 2004081233 A1 | 9/2004 |
| WO | 2005005601 A2 | 1/2005 |
| WO | 2005/048823 A2 | 6/2005 |
| WO | 2005/071408 A1 | 8/2005 |
| WO | 2005/091944 | 10/2005 |
| WO | 2005/113606 A2 | 12/2005 |
| WO | 2006/028595 A2 | 3/2006 |
| WO | 2006/028714 A1 | 3/2006 |
| WO | 2006/056492 A1 | 6/2006 |
| WO | 2006/065582 A2 | 6/2006 |
| WO | 2006/078463 A2 | 7/2006 |
| WO | 2006/097537 A2 | 9/2006 |
| WO | 2006/135886 A2 | 12/2006 |
| WO | 2006135886 A2 | 12/2006 |
| WO | 2006138275 A2 | 12/2006 |
| WO | 2007/146968 A2 | 12/2007 |
| WO | 2008049113 A2 | 4/2008 |
| WO | 2008/088849 A2 | 7/2008 |
| WO | 2008088849 A2 | 7/2008 |
| WO | 2008/121563 A2 | 10/2008 |
| WO | 2009/018386 A1 | 2/2009 |
| WO | 2009/020802 A2 | 2/2009 |
| WO | 2009/030771 A1 | 3/2009 |
| WO | 2009/117033 A2 | 9/2009 |
| WO | 2009/126380 A2 | 10/2009 |
| WO | 2009/141359 A1 | 11/2009 |
| WO | 2010/006060 A2 | 1/2010 |
| WO | 2010/042747 A2 | 4/2010 |
| WO | 2010/044952 A2 | 4/2010 |
| WO | 2010/065439 A1 | 6/2010 |
| WO | 2010/084169 A2 | 7/2010 |
| WO | 2010/132370 A2 | 11/2010 |
| WO | 2010/142665 A1 | 12/2010 |
| WO | 2010141469 A2 | 12/2010 |
| WO | 2011/005481 A1 | 1/2011 |
| WO | 2011/028952 A1 | 3/2011 |
| WO | 2011/047097 A2 | 4/2011 |
| WO | 2011055968 A2 | 5/2011 |
| WO | 2011/069104 A2 | 6/2011 |
| WO | 2011/091078 A2 | 7/2011 |
| WO | 2011/137362 | 11/2011 |
| WO | 2012/064733 | 5/2012 |

(56) References Cited

FOREIGN PATENT DOCUMENTS

| WO | 2012/088290 | 6/2012 |
|---|---|---|
| WO | 2012/088302 | 6/2012 |
| WO | 2012/109624 | 8/2012 |

OTHER PUBLICATIONS

De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Echtenacher et al., "Requirement of Endogenous Tumor Necrosis Factor/Cachectin for Recovery from Experimental Peritonitis." Journal of Immunology, Dec. 1, 1990, vol. 145, No. 11, pp. 3762-3766.
Fisher et al., Treatment of Septic Shock with the Tumor Necrosis Factor Receptor: Fc Fusion Protein.: The New England Journal of Medicine, 1996, vol. 334, No. 26, pp. 1697-1702.
Gibot et al., "A Soluble Form of the Triggering Receptor Expressed on Myeloid Cells-1 Modulates the Inflammatory Response in Murine Sepsis," The Journal of Experimental Medicine, Dec. 6, 2004, Vo. 200 No. 11 pp. 1419-1426.
Griffin et al., "Abnormal Hear Rate Characteristics Preceding Neonatal Sepsis and Sepsis-Like Illness," Pediatric Research, 2003, vol. 53, No. 6, pp. 920-926.
Hiscott et al., "Characterization of a Functional NF-kB Site in the Human Interleukin 1b Promoter: Evidence for a Positive Autoregulatory Loop," Molecular and Cellular Biology, Oct. 1993, vol. 13 No. 10, pp. 6231-6240.
Hotchkiss et al., "The Pathophysiology and Treatment of Sepsis," The New England Journal of Medicine, Jan. 9, 2003, pp. 138-150.
Keane et al., "Tuberculosis Associated with infliximab, a Tumor Necrosis Factor a-Neutralizing Agent," The New England Journal of Medicine, Oct. 11, 2001, vol. 345, No. 15, pp. 1098-1104.
Kelker et al., "Crystal Structure of Human Triggering Receptor Expressed on Myeloid Cells 1 (TREM-1) at 1.47 A," J. Mol. Biol. 2004, vol. 342, pp. 1237-1248.
Lantz et al., "Characterization In Vitro of a Human Tumor Necrosis Factor-binding Protein: A Soluble Form of a Tumor Necrosis Factor Receptor," J. Clin. Invest., Nov. 1990, vol. 89, pp. 1396-1402.
Lolis et al., "Therapeutic Approaches to Innate Immunity:Severe Sepsis and Septic Shock," Nature Reviews Drug Discovery, Aug. 2003, vol. 2, pp. 635-645.
NCBI Reference Sequences (RefSeq) NP_061113 (2 pgs).
Radaev et. al., "Crystal Structure of the Human Myeloid Cell Activation Receptor TREM-1," Structure, Dec. 2003, vol. 11, pp. 1527-1535.
Riedemann et al., "Novel strategies for the treatment of sepsis," Nature Medicine, May 2003, vol. 9, No. 5, pp. 517-524.
Stone, Richard, "Search for Sepsis Drugs Goes on Despite Past Failures." Science, Apr. 15, 1994, vol. 264, pp. 365-367.
Thoma-Uszynski et al., "Induction of Direct Antimicrobial Activity Through Mammalian Toll-Like Receptors," Science, Feb. 23, 2001, vol. 291, pp. 1544-1547.
Tsuji et al., "Simultaneous Onset of Acute Inflammatory Response, Sepsis-Like Symptoms and Intestinal Mucosal Injury After Cancer Chemotherapy," Int. J. Cancer, 2003, vol. 107, pp. 303-308.
Urban et al., "NF-kB contacts DNA by a heterodimer of the p50 and p65 subunit," The EMBO Journal, 1991, vol. 10, No. 7, pp. 1817-1825.
Van Zee et al., "Tumor necrosis factor soluble receptors circulate during experimental and clinical inflammation and can protect against excessive tumor necrosis factor a in vitro and in vivo," Proc. Natl. Acad. Sci. USA, Jun. 1992, vol. 89, pp. 4845-4849.
Vincent et al., "Clinical Trials of Immunomodulatory Therapies in Severe Sepsis and Septic Shock," Clin. Infect. Dis., Apr. 15 2002, vol. 34, pp. 1084-1093.
Warren, H. Sha, M.D., "Strategies for the Treatment of Sepsis," The New England Journal of Medicine, Mar. 27, 1997, vol. 336, No. 13, pp. 952-953.
Wasmuth et al., "Patient with acute on chromic liver failure display 'sepsis-like' immune paralysis," Journal of Hepatology, 2005, vol. 42, pp. 195-201.
Zwaveling et al., "High plasma tumor necrosis factor (TNF)-a concentrations and a sepsis-like syndrome in patients undergoing hyperthermic isolated limb perfusion with recombinant TNF-a, interferson-g, and melphalan," Crit Care Med, 1996, vol. 24, No. 5, pp. 765-770.
DATABASE EMBL, Sequence from Patent WO200283856-A2, Sep. 17, 2003 "Human G-protein coupled receptor phosphorylation site peptide SEQ ID 131", retrieved from EBI Database accession No. ABJ38803.
DATABASE EMBL, Sequence information from JP2000116377-A, Oct. 10, 2000 "N-terminus of porcine trypsin", retrieved from EBI Database accession No. AAB03087.
Wheeler et al., "Treating Patients with Severe Sepsis" NEJM 1999, 340: 207-214.
Attwood. "The Babel of Bioinformatics" Science 2000; 290: 471-473.
The Merck Manuals Online Medical Library (online). Whitehouse Station, NJ: Merck Research Laboratories, 2006-2007. (Retrieved on Nov. 19, 2007). Retrieved from the Internet: <URL: http://www.merck.com/mmpe/print/sec06/ch068/ch068a.html >.
Standen et al. "Septic Shock" N. Engl. J. Med. 2000, 343: 447-448.
Redl et at, "Animal Models as the Basis of Pharmacologic Intervention in Trauma and Sepsis Patients," World J. Surg. 1996, 20: 487-492.
Mori et al., "A novel amino acid substitution at the receptor-binding site on the hemagglutinin of H3N2 influenza A viruses isolated from 6 cases with acute encephalopathy during the 1997-1998 season in Tokyo," Archives of Birology 1999, 144: 147-155.
Gencic et al., "Conservative amino acid substitution in the myelin proteolipid protein of jimpymsd mice," The Journ. of Neuroscience 1990, 10: 117-124.
Schenk et al., "Trem-1 - Expressing Intestinal Macrophages Crucially Amplify Chronic Inflammation in Experimental Colitis and Inflammatory Bowel Diseases," The Journ. of Clinical Investigation, 2007, vol. 117, No. 10, pp. 3097-3106.
Proudfoot, "Transcriptional interference and termination between duplicated ; ; globin gene constructs suggests a novel mechanism for gene regulation," Nature, (1986), 322: 562 ;.
NCBI Reference Sequences (RefSeq) NP_067381 (2 pgs); ; ;.
Canton et al., "NKp44, atriggering receptor involved in tumor cell lysis by activated human natural killer cells, is a novel member of the immunoglobulin superfamily, " J. Exp. Med. 189(5), (1999), pp. 787-796.
Carrell et al., "A Novel Procedure for the Synthesis of Libraries Containing Small Organic Molecules" Angew. Chem. Int. Ed. Engl., (1994), 33:2059 & 2061.
Cella et al., "Anovel inhibitory receptor (ILT3) expressed on monocytes, macrophages, and dendritic cells involved in antigen processing", J. Exp. Med., vol. 185(10), (1997), pp. 1743-1751.
Chen et al., "Gene therapy for brain tumors: regression of experimental gliomas by adenovirus-mediated gene transfer in vivo.", Proc. Natl. Acad. Sci. USA, (1994), 91:3054-3057.
Cho et al., "An unnatural biopolymer ", Science, (1993), 261:1303.
Chomel et al., "Bartonella henselae Prevalence in Domestic Cats in California: Risk Factors and Association between Bacteremia and Antibody Titers.", Journal of Clinical Microbiology, vol. 33(9), (Sep. 1995), pp. 2445-2450.
Cohen et al., "[42] Receptor-mediated transport of DNA into eukaryotic cells", Meth. Enzymol., (1993), 217:618-644.
Clowes et al., "Long-term biological response of injured rat carotid artery seeded with smooth muscle cells expressing retrovirally introduced human genes.", J. Clin. Invest., (1994), 93:644-651.
Cohen et al., "Emerging Technologies for Sequencing Antisense Oligonucleotides: Capillary Electrophoresis and Mass Spectrometry," Adv. Chromatogr., (1996), 36:127-162.
Colberre-Garapin et al., "A new dominant hybrid selective marker for higher eukaryotic cells", J. Mol. Biol., (1981) 150:1.

(56) References Cited

OTHER PUBLICATIONS

Cotton et al., "Reactivity of cytosine and thymine in single-base-pair mismatches with hydroxylamine and osmium tetroxide and its application to the study of mutations", Proc. Natl. Acad. Sci. USA, (1988), 85:4397.
Cotton, "Current methods of mutation detection", Mutat. Res., (1993), 285:125-144.
Cox et al., "IL-10 enhances resolution of pulmonary inflammation in vivo by promoting apoptosis of neutrophils," Am. J. Physiol. Lung Cell Mol Physiol., (1996), 271:L566-L571.
Cronin et al., "Cystic fibrosis mutation detection by hybridization to light-generated DNA probe arrays", Human Mutation, (1996), 7:244-255.
Cruikshank et al., J. Acquired Immune Deficiency Syndromes and Human Retrovirology, (1997) 14:193.
Cull et al., "Screening for receptor ligands using large libraries of peptides linked to the C terminus of the lac repressor.", Proc. Natl. Acad. Sci. USA, (1992), 89:1865-1869.
Cwirla et al., "Peptides on phage: a vast library of peptides for identifying ligands.", Proc. Natl. Acad. Sci. USA, (1990), 87:6378-6382.
Daws et al., "Cloning and Characterization of a Novel Mouse Myeloid DAP12-Associated Receptor Family, " Eur. J. Immunol. 2001, 31:783-791.
Devlin, "Random peptide libraries: a source of specific protein binding molecules ",Science, (1990), 249:404-406.
Dewitt et al., "Diversomers": an approach to nonpeptide, nonoligomeric chemical diversity, Proc. Natl. Acad. Sci. USA, (1993), 90:6909.
Dietrich et al., "Signal-regulatory protein β1 is a DAP12-associated activation receptor expressed in myeloid cells." J. Immunol. 164:9, 2000.
Doerks et al., "Protein annotation: detective work for function prediction", Trends in Genetics, vol. 14(6), (Jun. 1998), pp. 248-250.
Downey et al., "Intracellular signaling in neutropohil priming and activation," Semin Cell Bio. 6:345-356, 1995.
Echtenacher et al., "Requirement of endogenous tumor necrosis factor/cachectin for recovery from experimental peritonitis," J. Immunol. 145:3762-6, 1990.
Echtenacher et al. "Critical protective role of mast cells in a model of acute septic peritonitis", Nature, (1996), 381:75-7.
Edlund et al., "Cell-specific expression of the rat insulin gene: evidence for role of two distinct 5' flanking elements", Science, (1985) 230:912-916.
Erb et al., "Recursive deconvolution of combinatorial chemical libraries",Proc. Natl. Acad. Sci. USA, (1994), 91:11422.
Eskandari et al., "Anti-tumor necrosis factor antibody therapy fails to prevent lethality after cecal ligation and puncture of endotoxemia", J. Immunol., (1992), 148:2724-30.
Facchetti et al., "Suppurative Granulomatous Lymphadenitis; Immunohistochemical Evidence for a B-cell-Associated Granuloma," Am. J. Surg. Pathol., (1992), 16: 955-61.
Felici, "Selection of antibody ligands from a large library of oligopeptides expressed on a multivalent exposition vector ", J. Mol. Biol., (1991), 222:301-310.
Fell et al., "Genetic construction and characterization of a fusion protein consisting of a chimeric F(ab') with specificity for carcinomas and human IL-2.", J. Immunol., (1991), 146:2446-2452.
Finn et al., Synthesis and Properties of DNA-PNA Chimeric Oligomers Nucleic Acids Res., (1996), 24(17): 3357-63.
Fodor, "Multiplexed biochemical assays with biological chips", Nature, (1993), 364:555-556.
Forster et al., "CCR7 coordinates the primary immune response by establishing functional microenvironments in secondary lymphoid organ," Cell 99:23-33, 1999.
Gallop et al., "Applications of Combinatorial Technologies to Drug Discovery. 1. Background and Peptide Combinatorial Libraries", J. Med. Chem., (1994), 37:1233.
Gasparini et al., "Restriction site generating-polymerase chain reaction (RG-PCR) for the probeless detection of hidden genetic variation: application to the study of some common cystic fibrosis mutations", Mol. Cell Probes, (1992), 6:1.
Gaultier et al.,"a-DNA IV: a-anomeric and b-anomeric tetrathymidylates covalently linked to intercalating oxazolopyridocarbazole. Synthesis, physicochemical properties and poly (rA) binding" Nucleic Acids Res., (1987), 15:6625-6641.
Gelrud et al., "Interaction of Tumor Necrosis Factor-a and Granulocyte Colony-Stimulation Factor on Neutrophil Apoptosis, Receptor Expression, and Bactericidal Function" Proc. Assoc. Am. PHYSICIANS, (1996), 108:455-456.
Gentz et al., "Bioassay for trans-activation using purified human immunodeficiency virus tat-encoded protein: trans-activation requires mRNA synthesis", Proc. Natl. Acad. Sci. USA, (1989), 86:821-824.
Gibbs et al., "Detection of single DNA base differences by competitive oligonucleotide priming" Nucleic Acids Res., (1989), 17:2437-2448.
Gibot et al., "Plasma Level of Trigering Receptor Expressed on Myeloid Cells-1: Its Diagnostic Accuracy in Patients with Suspected Sepsis," (2004), pp. 9-16.
Gibot et al., "Soluble Triggering Receptor Expressed on Myeloid Cells and the Diagnosis of Pneumonia, " The New England Journal of Medicine, (2004), pp. 451-458.
Gillies et al., "High-level expression of chimeric antibodies using adapted cDNA variable region cassettes", J. Immunol. Methods, (1989), 125:191-202.
Gillies et al., "Antibody-targeted interleukin 2 stimulates T-cell killing of autologous tumor cells", Proc. Natl. Acad. Sci. USA., (1992), 89:1428-1432.
Gingras et al., "TREM-1, MDL-1, and DAP12 Expression is Associated with a Mature Stage of Myeloid Development," Molecular Immunology 38 (2001) pp. 817-824.
Glauser et al., "Septic shock: pathogenesis," Lancet 338:732-6, 1991.
Goldspiel et al., "Human Gene Therapy," Clinical Pharmacy, (1993), 12:488-505.
Gon et al. Microbiol. Immunol., (1996) 40:463-465.
Griffin et al., "DNA sequencing", Appl. Biochem. Biotechnol., (1993), 38:147-159.
Grossman & Wilson, "Retroviruses: delivery vehicle to the liver", Curr. Opin. In Genetics and Devel., (1993), 3:110-114.
Arts Rob J W et al. "Trem-1 interaction with the LPS/TLR4 receptor complex" European Cytokine Network. 2011. vol. 22(1). p. 11-14.
R&D Systems: "Human Trem-1 Antibody." Internet Citation. Retrieved Nov. 27, 2012. http://www.rndsystems.com/Products/MAB1278.
Eleanor Molloy. "Triggering Receptor Expressed on Myeloid Cells (TREM) Family and the Application of its Antagonists." Recent Patents on Anti-Infective Drug Discovery. vol. 4(1). 2009. pp. 51-56.
Nagihan Bostanci et al. "Involvement of the TREM-1/DAP12 pathway in the innate immune responses to" Molecular Immunology. vol. 49(1) pp. 387-394.
Tessarz et al. "The TREM-1-DAP12 pathway." Immunology Letters. vol. 116(2) pp. 111-116.
Mohamadzadeh et al. "Activation of triggering receptor expressed on myeloid cells-1 on human neutrophils by Marburg and ebola viruses." Journal od Virology. 2006. vol. 80(14). pp. 7235-7244.
Weintraub et al., "Anti-sense RNA as a molecular tool for genetic analysis," Reviews—Trends in Genetics, (1986), vol. 1(1), pp. 22-25.
Wells, "Additivity of Mutational Effects in Proteins", Biochemistry, vol. 29(37), (Sep. 18, 1990), pp. 8509-8517.
Wigler et al., "Transfer of purified herpes virus thymidine kinase gene to cultured mouse cells," Cell, (1977), 11: 223.
Wigler et al., "Transformation of mammalian cells with an amplifiable dominant-acting gene," Natl. Acad. Sci. USA, (1980), 77: 3567.
Wilmut et al., "Viable offspring derived from fetal and adult mammalian cells," Nature, (1997), 385: 810-813.
Wilson et al., "The structure of an antigenic determinant in a protein", Cell, vol. 37(3), (1984), pp. 767-778.
Winoto & Baltimore, "A novel, inducible and T cell-specific enhancer located a the 38' end of the T cell receptor a locus," Embo J., (1989), 8: 729-733.

(56) References Cited

OTHER PUBLICATIONS

Wu & Wu, "Receptor-mediated in vitro gene transformation by a soluble DNA carrier system," J. Biol. Chem., (1987), 262: 4429-4432.
Wu & Wu, "Delivery systems for gene therapy," Biotherapy, (1991), 3: 87-95.
Yamashita, "Inhibitory and stimulatory functions of paired Ig-like receptor (PIR family in RBL-2H3 Cells," J. Immunol. 161, (1998), pp. 4042-4047.
Zervos et al., "Mxi1, a protein that specifically interacts with Max to bind Myc-Max recognition sites," Cell, (1993), 72: 223-232.
Zijlstra et al., "Germ-line transmission of a disrupted b2-microglobulin gene produced by homologous recombination in embryonic stem cells," Nature, (1989), 342: 435-438.
Zon, "Oligonucleotide Analogues as Potential Chemotherapeutic Agents," Pharm. Res., (1988), 5: 539-549.
Zuckermann et al., "Discovery of Nanomolar Ligands for 7-Transmembrane G-Protein-Coupled Receptors from a Diverse N-(Substituted)glycine Peptoid Library," J. Med.Chem., (1994), 37: 2678.
Basic Methods in Molecular Biology, Elsevier Science Publishing Co., New York, (1986), pp. 75-78 and 84-87.
Current Protocols in Molecular Biology, John Wiley & Sons, New York, (1989), Supp 24, 6.3.1-6.3.6.
NCBL Sequence Viewer Accession No. D78812 (Jul. 20, 2006).
NCBL Sequence Viewer Accession No. AI337247 (Mar. 18, 1999).
NCBL Sequence Viewer Accession No. AW139572 (Oct. 30, 1999).
NCBL Sequence Viewer Accession No. AW274906 (Jan. 3, 2000).
NCBL Sequence Viewer Accession No. AW139573 (Oct. 30, 1999).
NCBL Sequence Viewer Accession No. AW394041 (Feb. 4, 2000).
NCBL Sequence Viewer Accession No. AI621023 (Dec. 14, 1999).
NCBL Sequence Viewer Accession No. AI186456 (Oct. 28, 1998).
NCBL Sequence Viewer Accession No. AI968134 (Aug. 25, 1999).
NCBL Sequence Viewer Accession No. AI394092 (Mar. 30, 1999).
NCBL Sequence Viewer Accession No. AI681036 (Dec. 16, 1999).
NCBL Sequence Viewer Accession No. AI962750 (Mar. 8, 2000).
NCBL Sequence Viewer Accession No. AA494171 (Aug. 19, 1997).
NCBL Sequence Viewer Accession No. AA099288 (May 11, 1997).
NCBL Sequence Viewer Accession No. AW139363 (Oct. 30, 1999).
NCBL Sequence Viewer Accession No. AW135801 (Oct. 29, 1999).
NCBL Sequence Viewer Accession No. AA101983 (May 11, 1997).
NCBL Sequence Viewer Accession No. AF196329 (May 24, 2000).
NCBL Sequence Viewer Accession No. AF213457 (May 23, 2000).
NCBL Sequence Viewer Accession No. N41388 (Jan. 24, 1996).
Sharif and Knapp, "From expression to signaling: Roles of TREM-1 and TREM-2 in innate immunity and bacterial infection," Immunobiology, vol. 213, No. 9-10, pp. 701-713 (2008).
Turnbull et al., "Cutting Edge: TREM-2 Attenuates Macrophage Activation," J. Immunol., vol. 177, pp. 3520-3524 (2006).
Adrie et al., "Postresuscitation disease after cardiac arrest: a sepsis-like syndrom?", Current Opinion in Critical Care, Jun. 2004, vol. 10, pp. 208-212.
Begum et al., "Mycobacterium bovis BCG Cell Wall-Specific Differentially Expressed Genes Identified by Differential Display and cDNA Subtraction in Human Macrophages," Infection and Immunity, Feb. 2004, pp. 937-948.
Beleharski et al., "ARole for Triggering Receptor Expressed on Myeloid Cells-1 in Host Defense During the Early-Induced and Adaptive Phases of the Immune Response," The Journal Immunology, 2003, vol. 170, pp. 3812-3818.
Bone et al., "Definitions for Sepsis and Organ Failure and Guidelines for the Use of Innovative Therapies in Sepsis," Jun. 1992, vol. 101, pp. 1644-1655.
Cohen, Jonathan, "TERM-1 in sepsis,"The Lancet, Sep. 8, 2001, vol. 358, pp. 776-778.
Cohen, Jonathan, "The immunopathogenesis of sepsis, " Nature, Dec. 19/26, 2002, vol. 420, pp. 885-891.
Collart et al., "Regulation of Tumor Necrosis Factor Alpha Transcription in Macrophages: Involvement of Four kB-Like Motifs and Constitutive and Inducible Forms of NF-kB, " Molecular and Cellular Biology, Apr. 1990, vol. 10, No. 4, pp. 1498-1506.
Colonna et al., TREM-1 (Triggering Receptor Expressed on Myeloid Cells): A New Player in Acute inflammatory Responses, Journal of Infectious Diseases, 2003, 187, suppl. 2: pp. S397-S401.
Colonna et al., "TREMS in the Immune System and Beyond." Nature Reviews Immunology, Jun. 2003, vol. 3, No. 6, pp. 445-453 (printed as pp. 1-9).
Dinarello et al., "Proinflammatory and Ant-inflammatory Cytokines as Mediators in the Pathogenesis of Septic Shock," Chest, Dec. 1997, vol. 112, No. 6, pp. 321S-329S.
Echtenacher et al., "Tumor Necrosis Factor-Dependen Adhesions as a Major Protective Mechanism Early in Septic Peritonitis in Mice." Infection and Immunity, Jun. 2001, vol. 69, No. 6, pp. 3550-3555.
Coskun et al , Endocrinology, "Fibroblast Growth Factor 21 Corrects Obesity in Mice", 2008, vol. 149, No. 12, pp. 6018-6027.
Erickson et al., Journal of Lipid Research, "Nonalcoholic Fatty Liver Disease", 2008, Volume—, Number—, pp. S412-S416.
Grundy et al., Circulation, "Definition of Metabolic Syndrome: Report of the National Heart, Lung, and Blood Institute/American Heart Association Conference on Scientific Issues Related to Definition", 2004, vol. 109, Number—, pp. 433-438.
Kharitonenkov et al., Endocrinology, "The Metabolic State of Diabetic Monkeys Is Regulated by Fibroblast Growth Factor-21", 2007, vol. 148, No. 2, pp. 774-781.
Kharitonenkov et al., Journal of Clinical Investigation, "FGF-21 As a Novel Metabolic Regulator", 2005, vol. 115, Number—, pp. 1627-1635.
Knudsen, L.B., Journal of Medicinal Chemistry, "Glucagon-Like Peptide-1: The Basis of a New Class of Treatment for Type 2 Diabetes", 2004, vol. 47, No. 17, pp. 4128-4134.
Micanovic et al., Journal of Cellular Physiology, "Different Roles of N- and C- Termini in the Functional Activity of FGF21", 2009, vol. 219, No. 2, pp. 227-234.
Nauck, M.A et al., Regulatory Peptides, "Glucagon-Like Peptide 1 and Its Derivatives in the Treatment of Diabetes", 2005, vol. 128, No. 2, pp. 135-148.
Xu et al., Diabetes, "Fibroblast Growth Factor 21 Reverses Hepatic Steatosis, Increases Energy Expenditure, and Improves Insulin Sensitivity in Diet-Induced Obese Mice", 2009, vol. 58, No. 1, pp. 250-259.
Yie et al., FEBS Letters, "FGF21 N- and C-Termini Play Different Roles in Receptor Interaction and Activation", 2009, vol. 583, No. 1, pp. 19-24.
Abravaya et al., "Detection of point mutations with a modified ligase chain reaction (Gap-LCR)" Nucleic Acids Res., (1995), 23:675-682.
Aderem et al., "Toll-Olike receptors in the induction of the innate immune response." Nature, 406:782-7.
Alexander et al., "A recombinant human receptor antagonist to interleukin 1 improves survival after lethal endotoxemia in mice", J. Exp. Med., 173:1029-32, 1991.
Ames et al., "Conversion of murine Fabs isolated from a combinatorial phage display library to full length immunoglobulins", J. Immunol. Methods, vol. 184(2), (1995), pp. 177-186.
Amman et al., "Tightly regulated tac promoter vectors useful for the expression of unfused and fused proteins in *Escherichia coli* ", Gene, (1988), 69:301-315.
Appelmelk et al., "Use of mucin and hemoglobin in experimental murine Gram-negative bacteremia enhances the immunoprotective action of antibodies reactive with the lipopolysaccharide core region", Antonie Van Leeuwenhoek, (1986), 52:537-42.
Arnon et al., "Monoclonal Antibodies for Immunotargeting of Drugs in Cancer Therapy", in Monoclonal Antibodies and Cancer Therapy, Reisfeld et al., eds., Alan R. Liss, Inc., (1985), pp. 243-256.
Baker et al., "NK cell activation: distinct stimulatory pathways counterbalancing inhibitory signals", Hum Immunol., 61:18-27. 2000.
Bakker et al., "DAP12-deficient mice fail to develop autoimmunity due to impaired antigen priming." Immunity 13:345-53. 2000.
Bakker et al., "Myeloid DAP12-associating lectin (MDL)-1 is a cell surface receptor involved in the activation of myeloid cells, "Proc. Natl. Acad. Sci. USA 96:9792, 1999.
Baldwin et al., "Analysis Results, and Future Prospective of the Therapeutic Use of the Radiolabeled Antibody in Cancer Therapy",

(56) References Cited

OTHER PUBLICATIONS in Monoclonal Antibodies for Cancer Detection and Therapy, eds. Adacemic Press, (1985, pp. 303-316.
Banerji et al., "A lymphocyte-specific cellular enhancer is located downstream of the joining region in immunoglobulin heavy chain genes", Cell, (1983), 33:729-740.
Barany,"Genetic disease detection and DNA amplification using cloned thermostable ligase", Proc. Natl. Acad. Sci. USA, (1991), 88:189.
Baldari et al., "A novel leader peptide which allows efficient secretion of a fragment of human interleukin 1b in Saccharomyces cerevisiae," Embo J., (1987), 6:229-234.
Bartel et al., Bio Techniques, (1993), 14:920-924.
Bartel et al., "Isolation of new ribozymes from a large pool of random sequences",Science, (1993), 261:1411-1418.
Bauer et. al., "Activation of NK cells and T cells by NKG2D, a receptor for stress-inducible MICA", Science, 285:727-9, 1999.
Benda et al., "Differentiated Rat Glial Cell Strain in Tissue Culture," Science, (1968), 161:370-371.
Better et al., "Escherichia coli secretion of an active chimeric antibody fragment," Science, (1988), 240:1041-1043.
Beutler et al., "Passive immunization against cachectin/tumor necrosis factor protects mice from lethal effect of endotoxin", Science, 229:869-71, 1985.
Beutler, B., "Endotoxin, toll-like receptor 4, and the afferent limb of innate immunity", Curr. Opin. Microbiol., vol. 3 (1), (2000), pp. 23-28.
Boesen et al., "Circumvention of chemotherapy-induced myelosuppression by transfer of the mdr1 gene," Biotherapy, (1994), 6:291-302.
Bolin et al., "Survey of cell lines in the American Type Culture Collection for bovine viral diarrhea virus", J. Virol. Methods, (1994), 48: 211-221.
Bone, "The pathogenesis of sepsis," Ann. Intern. Med. 115:457-69, 1991.
Bordelon-Riser et al., "Necessity for two human chromosomes for human chorionic gonadotropin production in human-mouse hybrids", Somatic Cell Genetics, (1979), 5:597-613.
Bork & Bairoch, "Go hunting in sequence databases but watch out for the traps", Trends in Genetics, (1996)vol. 12(10), pp. 425-427.
Bork, "Powers and Pitfalls in Sequence Analysis: The 70% Hurdle", Genome Research, (2000), 10:398-400.
Bouchon et al., "Cutting edge: inflammatory responses can be triggered by TREM-1, a novel receptor expressed on neutroophils and monocytes", J. Immunol., vol. 164 (10). May 15, 2000), pp. 4991-4995.
Bouchon et al., "TREM-1 amplifies inflammation and is a crucial mediator of septic shock", Nature, vol., 410(6832), (Apr. 26, 2001), pp. 1103-1107.
Bout et al., "Lung Gene Therapy: In Vivo Adenovirus-Mediated Gene Transfer to Rhesus Monkey Airway Epithelium", Human Gene Therapy, (1994), 5:3-10.
Bradley, Teratocarcinomas and Embryonic Stem Cells: A Practical Approach, Robertson, ed., IRL, Oxford, (1987), pp. 113-152.
Bradley, "Modifying the mammalian genome by gene targeting", Current Opinion in Bio Technology, (1991), 2:823-829.
Brenner, "Errors in genome annotation", Trends in Genetics, vol. 15(4), (Apr. 1999), pp. 132-133.
Brinkman et al., "Phage display of disulfide-stabilized Fv fragments", J. Immunol. Methods, (1995), 182:41-50.
Burton et al., "Human Antibodies from Combinatorial Libraries ", Advances in Immunology, (1994), 57:191-280.
Byrne & Ruddle, "Multiplex gene regulation: a two-tiered approach to transgene regulation in transgenic mice", Proc. Natl. Acad. Sci. USA, (1989), 86:5473-5477.
Calame et al., "Transcriptional controlling elements in the immunoglobulin and T cell receptor loci", Adv. Immunol., vol. 43, (1988), pp. 235-275.
Calandra et al., J. Immunol., (2000), 145:3762-6.
Calandra et al., "Protection from septic shock by neutralization of macrophage migration inhibitory factor, " Nat. Med., 6:164-70, 2000.
Campes & Tilghman, "Postnatal repression of the alpha-fetoprotein gene is enhancer independent", Genes Dev., (1989), 3:537-546.
Guatelli et al., "Isothermal, in vitro amplification of nucleic acids by a multienzyme reaction modeled after retroviral replication", Proc. Natl. Acad. Sci. USA, (1990), 87:1874-1878.
Haapala et al., "Isolation from cats of an endogenous type C virus with a novel envelope glycoprotein.", J. Virol., (1985), 53:827-833.
Hammerling et al., Moloclonal Antibodies and T-Cell Hybridomas, Elsevier, New York, (1981) pp. 563-681.
Harlow et al., Antibodies: A Laboratory Manual, 2nd ed., Cold Spring Harbor Laboratory Press, (1988).
Haselhoff et al., "Simple RNA enzymes with new and highly specific endoribonuclease activities", Nature, (1988), 334: 585-591.
Hayashi, "PCR-SSCP: A method for detection of mutations ", Genet. Anal. Tech. Appl., (1992), 9:73-79.
He et al., "Expression of O6-Methylguanine-DNA Methyltransferase in Six Human Medulloblastoma Cell Lines ", Cancer Res., (1992), 52:1144-1148.
Hebert et al., "Sequential morphologic events during apoptosis of human neutroophils. Modulation by lipoxygenase-derived eicosanoids.", J. Immunol., (1996), 157:3105-3115.
Helene, "The anti-gene strategy: control of gene expression by triplex-forming-oligonucleotides" Anticancer Drung Des., (1991), 6(6):569-84.
Helene, "Control of Gene Expression by Triple Helix-Forming Oligonucleotides. The Antigene Strategy", Ann. N. Y. Acad. Sci., (1992), 660:27-36.
Hellstrom et al., "Antibodies for Drug Delivery" in Controlled Drug Delivery, 2nd edition, Robinson et al., eds., Marcel Dekker, Inc., (1987), pp. 623-653.
Hoffman et al., "Phylogenetic perspectives in innate immunity", Science, vol. 284(5418), 1999, pp. 1313-1318.
Houghten, Bio Techniques, (1992), 13:412-421.
Hsu et al., "Detection of DNA point mutations with DNA mismatch repair enzymes", Carcinogenesis, (1994), 15:1657-1662.
Huston et al., "Protein engineering of single-chain Fv analogs and fusion proteins", Methods in Enzymology, (1991), 203-46-88.
Hyrup et al., "Peptide Nucleic Acids (PNA): Synthesis, properties and potential applications", Bioorganic & Medicinal Chemistry, 1996, 4(1): 5-23.
Inoue et al., "Synthesis and hybridization studies on two complementary nona(2'-O-methyl)ribonucleotides" Nucleic Acids Res., (1987), 15: 6131-6148.
Inoue et al., "Sequence-dependent hydrolysis of RNA using modified oligonucleotide splints and RNase H", FEBS Lett., (1987), 215: 327-330.
Iwabuchi et al., Oncogene, (1993), 8: 1693-1696.
Jespers et al., Bio Technology, (1988), 12: 899-903.
Jobling & Holmes, "Analysis of structure and function of the B Subunit of cholera toxin by the use of site-directd mutagenesis", Molecular Microbiology, vol. 5(7), pp. 1755-1767.
Katsuura et al., "CD48 expression on leukocytes in infectious diseases: flow cytometric analysis of surface antigen", Acta Paediatr Jpn., vol. 40(6), 1998, pp. 580-585.
Kaufman et al., Embo J., (1987), 6: 187-195.
Keen et al., "Rapid detection of single base mismatches as heteroduplexes on Hydrolink gels", Trends Genet., (1991), 7:5.
Kessel & Gruss, "Murine developmental control genes", Science, (1990), 249: 374-379.
Kettleborough et al., "Isolation of tumor cell-specific single-chain Fv from immunized mice using phage-antibody libraries and the reconstruction of whole antibodies from these antibody fragments", Eur. J. Immunol., vol. 24(4), 1994, pp. 952-958.
Kiem et al., Retrovirus-Mediated Gene Transduction into Canine Peripheral Blood Repopulating Cells, Blood, (1994), 83: 1467-1473.
Knappik et al., Biotechniques, (1994), 17(4): 754-761.
Kohler, "Immunoglobulin chain loss in hybridoma lines", Proc. Natl. Acad.Sci. USA, (1980), 77: (4) 2197.

(56) References Cited

OTHER PUBLICATIONS

Koller & Smithies, "Inactivating the beta 2-microglobulin locus in mouse embryonic stem cells by homologous recombination", Proc. Natl. Acad. Sci. USA (1989), 86: 8932-8935.
Kozal et al., "Extensive polymorphisms observed in HIV?1 clade B protease gene using high?density oligonucleotide arrays ", Nature Medicine, (1996), 2: 753-759.
Kozarsky & Wilson, "Gene therapy: adenovirus vectors", Current Opinion in Genetics and Development, (1993), 3: 499-503.
Krol et al., "Modulation of Eukaryotic Gene Expression by Complementary RNA or DNA Sequences" Bio/Techniques, (1988), 6: 958-976.
Kruse et al., "Characterization of a continuous human glioma cell line DBTRG-05MG: growth kinetics, karyotype, receptor expression, and tumor suppressor gene analyses", In Vitro Cell. Dev. Biol., (1992), 28A: 609-614.
Kubagawa et al., "Biochemical nature and cellular distribution of the paird immunoglobulin-like receptors, PIR-B." J. Exp. Med 189:309, 1999.
Kunkel et al., "Rapid and efficient site-specific mutagenesis without phenotypic selection", Methods Enzymol., (1987), 154: 367-82.
Kurjan & Herskowitz, "Structure of a yeast pheromone gene (MF?): A putative ?-factor precursor contains four tandem copies of mature ?-factor", Cell (1982), 30: 933-943.
Kwoh et al., "Transcription-based amplification system and detection of amplified human immunodeficiency virus type 1 with a bead-based sandwich hybridization format", Proc. Natl. Acad. Sci. USA, (1989), 86: 1173-1177.
Lakso et. al., "Targeted oncogene activation by site-specific recombination in transgenic mice", Proc. Natl. Acad. Sci. USA, (1992) 89: 6232-6236.
Lam, Nature, "A new type of synthetic peptide library for identifying ligand-binding activity", (1991), 354: 82-84.
Lam, "Mini-review. Application of combinatorial library methods in cancer research and drug discovery", Anticancer Drug Des., (1997), 12: 145.
Landegran et al., "A ligase-mediated gene detection technique", Science, (1988), 241: 1077-1080.
Lane et al., "CD40 ligand-independent B cell activation revealed by CD40 ligand-deficient T cell clones: evidence for distinct activation requirements for antibody formation and B cell proliferation", Eur. J. Immunol., (1995), 6: 1788.
Lanier et al., "NK cell receptors," Annu. Rev. Immunol., 16: 359 (1998).
Lanier, LL, "Immunoreceptor DAP12 bearing a tyrosine-based activation motif is involved in activating NK cells", Nature, vol. 391 (6668), (1998), pp. 703-707.
Lemaitre et al., "Specific antiviral activity of a poly(L-lysine)-conjugated oligodeoxyribonucleotide sequence complementary to vesicular stomatitis virus N protein mRNA initiation site", Proc. Natl. Acad. Sci. USA, (1987), 84: 648-652.
Letsinger et al., "Cholesteryl-conjugated oligonucleotides: synthesis, properties, and activity as inhibitors of replication of human immunodeficiency virus in cell culture", Proc. Natl. Acad. Sci. USA, (1989), 86: 6553-6556.
Li et al., "Targeted mutation of the DNA methyltransferase gene results in embryonic lethality," Cell, (1992), 69: 915.
Queen & Baltimore, "Immunoglobulin gene transcription is activated by downstream sequence elements," Cell, (1983), 33: 741-748.
Radany et al., "Directed establishment of rat brain cell lines with the phenotypic characteristics of type 1 astrocytes," Proc. Natl. Acad. Sci. USA, (1992) 89: 6467-6471.
Rheinwald, "Chapter 15 Serial Cultivation of Normal Human Epidermal Keratinocytes," Meth. Cell Bio., (1980), 21A: 229.
Riechmann et al., "Reshaping human antibodies for therapy," Nature, (1988), 332: 323.
Roguska et al., "Humanization of murine monoclonal antibodies through variable domain resurfacing," Proc. Natl. Acad. Sci. USA, (1994), 91: 969-973.

Rosenbaum & Reissner, "Temperature-gradient gel electrophoresis: Thermodynamic analysis of nucleic acids and proteins in purified form and in cellular extracts," Biophys. Chem., (1987), 26:235-246.
Rosenberg et al., "Inflammation," in Fundamental Immunology, 4th Ed. W. E. Paul, ed., p. 1051, 1999.
Rosenfeld et al., "Adenovirus-mediated transfer of a recombinant alpha 1-antitrypsin gene to the lung epithelium in vivo," Science, (1991), 252: 431-434.
Rosenfeld et al., "In vivo transfer of the human cystic fibrosis transmembrane conductance regulator gene to the airway epithelium," Cell, (1992), 68:143-155.
Rothe et al., "Mice lacking the tumour necrosis factor rector receptor 1 are resistant to TNF-mediated toxicity but highly susceptible to infection by Listeria monocytogenes" Nature, vol. 364, (1993), pp. 798-802.
Saiki et al., "Analysis of enzymatically amplified b-globin and HLA-DQa DNA with allele-specific oligonucleotide probes," Nature, (1986), 324: 163.
Saiki et al., "Genetic analysis of amplified DNA with immobilized sequence-specific oligonucleotide probes," Proc. Natl. Acad. Sci. USA, (1989), 86:6230.
Saleeba et al., "Chemical cleavage of mismatch to detect mutations," Methods Enzymol., (1992), 217: 286-295.
Sallusto et al., "Efficient peresentation of soluble antigen by cultured human dendritic cells is maintained by granulocyte/macrophage colony-stimulation factor plus interleukin 4 and downregulated by tumor necrosis factor alpha", J. Exp. Med., 1994, vol. 179(4), pp. 1109-1118.
Salmons & Gunzberg, "Targeting of Retroviral Vectors for Gene Therapy," Human Gene Therapy, (1993), 4: 129-141.
Sambrook et al., Molecular Cloning, A Laboratory Manual, 2nd Edition, Cold Spring Harbor Laboratory, Cold Spring Harbor, NY , (1990), Chapters 16 & 17.
Sanger, "DNA sequencing with chain-terminating inhibitors," Proc. Natl. Acad. Sci. USA, (1977), 74: 5463.
Santerre et al., "Expression of prokaryotic genes for hygromycin B and G418 resistance as dominant-selection markers in mouse L cells," Gene, (1984), 30: 147.
Sawai et al., "Direct Production of the Fab Fragment Derived From the Sperm Immobillizing Antibody Using Polymerase Chain Reaction and cDNA Expression Vectors," AJRI, (1995), 34:26-34.
Schultz et al., "Expression and secretion in yeast of a 400-kda envelope glycoprotein derived from epstein-barr virus," Gene, (1987), 54: 113-123.
Scott & Smith, "Searching for peptide ligands with an epitope library," Science, (1990), 249: 386-390.
Seed, "An LFA-3 cDNA encodes a phospholipid-linked membrane protein homologous to its receptor CD2," Nature, (1987), 329: 840.
Shu et al., "Secretion of a single-gene-encoded immunoglobulin from myeloma cells", Proc. Natl. Acad. Sci. USA, vol. 90(17), (1993), pp. 7995-7999.
Skerra et al., "Assembly of a functional immunoglobulin Fv fragment in *Escherichia coli* ", Science, vol. 240(4855), (1988), pp. 1038-1041.
Skolnick & Fetrow, "From gene to protein structure and function: novel applications of computational approaches in the genomic era", Trends in Biotech, vol. 18(1), (2000) pp. 34-39.
Smith et al., "Production of human beta interferon in insect cells infected with a baculovirus expression vector," Mol. Cell Biol., (1983), 3: 2156-2165.
Smith & Johnson, "Single-step purification of polypeptides expressed in *Escherichia coli* as fusions with glutathione S-transferase," Gene, (1988), 67: 31-40.
Smith & Zhang, "The challenges of genome sequence annotation or 'The devil is in the details'", Nature Biotechnology, vol. 15 (Nov. 1997), pp. 1222-1223.
Springer et al., "Traffic signals for lymphocyte recirculation and leukocyte emigration: The multistep paradigm," Cell, 76: 301, 1994.
Stemple & Anderson, "Isolation of a stem cell for neurons and glia from the mammalian neural crest," Cell, (1992), 71:973-985.

(56) References Cited

OTHER PUBLICATIONS

Studnicka et al., "Human-engineered monoclonal antibodies retain full specific binding activity by preserving non-CDR complementarity-modulating residues," Protein Engineering, (1994), 7(6):805-814.
Sugimoto et al., "Determination of cell surface membrane antigens common to both human neuroblastoma and leukemia-lymphoma cell lines by a panel of 38 monoclonal antibodies", J. Natl. Cancer Inst., vol. 73(1), (1984), pp. 51-57.
Szybalska & Szybalski, "Genetics of human cell lines, IV. DNA-mediated heritable transformation of a biochemical trait," Proc. Natl. Acad. Sci. USA, (1962), 48: 2026.
Thomas & Capecchi, "Site-directed mutagenesis by gene targeting in mouse embryo-derived stem cells," Cell, (1987), 51: 503.
Thorpe et al., "The Preparation and Cytotoxic Properties of Antibody-Toxin Conjugates," Immunol. Rev., (1982), 62: 119-58.
Thorpe, Antibody Carriers of Cytotoxic Agents in Cencer Therapy: A Review, in Monoclonal Antibodies 84: Biological and Clinical Applications, Pinchera et al., eds., (1985), pp. 475-506.
Tolstoshev, "Gene Therapy, Concepts, Current Trials and Future Directions," Ann. Rev. Pharmacol. Toxicol., (1993), 32: 573-596.
Tomasello et al., "Combined natural killer cell and dendritic cell functional deficiency in KASRAP/DAP12 loss-of-function mutant mice", Immunity 13: 355-64, 2000.
Tomic et al., "A rapid and simple method for introducing specific mutations into any position of DNA leaving all other positions unaltered," Nucleic Acids Res., (1990), 18(6): 1656.
Tracey et al., "Shock and tissue injury induced by recombinant human cachectin." Science 234-470-4 1986.
Traunecker et al., "Myeloma based expression system for production of large mammalian proteins," Trends Biotechnol., vol. 9, (1991), pp. 109-113.
Trowbridge et al., "Establishment and characterization of ferret cells in culture," In Vitro, (1982), 18: 952-960.
Ulevitch et al., "Recognition of Gram-negative bacteria and endotoxin by the innate immune system," Curr. Opin. Immunol, vol. 11, (1999), pp. 19-22.
Upender et al., "Megaprimer Method for In Vitro Mutagenesis Using Parallel Templates," Biotechniques, (1995), 18 (1): 29-30, 32.
Van Keuren et al., "Regional assignment of human liver-type 6-phosphofructokinase to chromosome 21q22.3 by using somatic cell hybrids and a monoclonal anti-L antibody," Hum. Genet., (1986), 74:34-40.
Wada et al., "Codon usage tabulated from the GenBank genetic sequence data," Nucleic Acid Res., (1992), 20: 2111-2118.
Wakayama et al., "Mice cloned from embryonic stem cells," Proc. Natl. Acad. Sci. USA, (1999), 96: 14984-14989.
Walsh et al., "Gene Therapy for Human Hemoglobinopathies," Proc. Soc. Exp. Biol. Med., (1993), 204: 289-300.
Wang et al., "A packaging cell line for propagation of recombinant adenovirus vectors containing two lethal gene-region deletions," Gene Therapy, (1995), 2: 775-783.
Wang et al., "HMG-1 as a late mediator of endotoxin lethality in mice", Science, vol. 285, (1999), pp. 248-251.
Lizardi et al., "Exponential amplification of recombinant-RNA hybridization probes," Nature Biotechnology, (1988), 6: 1197-1202.
Loeffler & Behr, "Gene transfer into primary and established mammalian cell lines with lipopolyamine-coated DNA," Meth. Enzymol., (1993), 217: 599-618.
Lonberg et al., "Human antibodies from transgenic mice", Int. Rev. Immunol., vol. 13(1), (1995) pp. 65-93.
Lowy et al., "Isolation of transforming DNA: Cloning the hamster aprt gene," Cell, (1980), 22: 817.
Lucklow & Summers, "High level expression of nonfused foreign genes with Autographa californica nuclear polyhedrosis virus expression vectors," Virology, (1989), 170: 31-39.
Madura et al., "N-recognin/Ubc2 interactions in the N-end rule pathway," J. Biol. Chem., (1993), 17: 5973-88.
Mag et al., "Synthesis and selective cleavage of oligodeoxyribonucleotldes containing non-chiral internucieotlde phosphoramidate linkages," Nucleic Acids Res., (1989), 17: 5973-88.
Maher, "DNA Triple-Helix Formation: An Approach to Artificial Gene Repressors?," Bioassays, (1992), 14(12): 807-15.
Malaviya et al., "Mast cell modulation of neutorphil influx and bacterial clearance at sites of infection thrugh TNF-alpha", Nature, 381, (1996), pp. 77-80.
Mastrangeli et al., "Diversity of airway epithelial cell targets for in vivo recombinant adenovirus-mediated gene transfer," J. Clin. Invest., (1993), 91: 225-234.
Maxam & Gilbert, "A new method for sequencing DNA," Proc. Natl. Acad. Sci. USA, (1977), 74: 560.
McNamara et al., "Interleukin-1 receptor antibody (IL-1rab) protection and treatment against lethal endotoxemia in mice", J. Surg. Res., 54, (1993), 316-21.
Medzhitov et al., "Innate immunity", N. Engl. J. Med., vol. 343, (2000), pp. 338-344.
Michael et al., Biotechniques, (1994), 16(3): 410-412.
Miller et al., "Use of retroviral vectors for gene transfer and expression," Meth. Enzymol., (1993), 217: 581-599.
Morgan & Anderson, "Human Gene Therapy," Ann. Rev. Biochem., (1993), 62: 191-217.
Morrison et al., "Endotoxins and disease mechanisms." Annu. Rev. Med. 38: 417-32, 1987.
Morrison, "Transfectomas provide novel chimeric antibodies," Science, (1985), 229: 1202.
Mulligan, "The basic science of gene therapy," Science, (1993), 260: 926-932.
Mulligan & Berg, "Selection for animal cells that express the *Escherichia coli* gene coding for xanthine-guanine phosphoribosyltransferase," Proc. Natl. Acad. Sci. USA, (1981), 78: 2072.
Mullinax et al., Bio Techniques, (1992), 12(6): 864-869.
Myers et al., "Detection of single base substitutions in total genomic DNA," Nature, (1985), 313: 495.
Myers et al., "Detection of single base substitutions by ribonuclease cleavage at mismatches in RNA:DNA duplexes," Science, (1985), 230: 1242.
Nakajima et al., "Human myeloid cells express and activating ILT receptor (ILTI) that associates with Fc receptor y-chain," J. Immunol. 162: 5. (1999), pp. 5-8.
Nakajima et al., "2B4: an NK cell activating receptor with unique specificity and signal transduction mechanism", Humm Immunol., vol. 61, (2000), pp. 39-43.
Nakazawa et al., "UV and skin cancer: specific p53 gene mutation in normal skin as a biologically relevant exposure measurement," Proc Natl. Acad. Sci. USA, (1994), 91: 360-364.
Naramura et al., "Mechanisms of cellular cytotoxicity mediated by a recombinant antibody-IL2 fusion protein against human melanoma cells," Immunol. Lett., (1994), 39: 91-99.
Nathan & Ding, "TREM-1: A new regulator of innate immunity in sepsis syndrome", Nature Medicine, vol. 7(5), May, 2001), pp. 530-532.
Nederman et al., "An in vitro bioassay for quantitation of human interferons by measurements of antiproliferative activity on a continuous human lymphoma cell line." Biologicals, vol. 18(1), (1990), pp. 29-34.
Ngo et al., "The Protein Folding Problem and Tertiary Structure Prediction, Chapter 14: Computational Complexity Protein Structure Prediction, and the Levinthal Paradox", (Mar. 2, 1995), pp. 492-495.
Nicoletti et al., "A rapid and simple method for measuring thymocyte apoptosis by propidium iodide staining and flow cytometry," J. Immunol. Methods, (1991), 139: 271-279.
O'Gorman et al., "Recombinase-mediated gene activation and site-specific integration in mammalian cells," Science, (1991), 251: 1351-1355.
O'Hare et al., "Transformation of mouse fibroblasts to methotrexate resistance by a recombinant plasmid expressing a prokaryotic dihydrofolate reductase," Proc. Natl. Acad. Sci. USA, (1981), 78: 1527.

(56) References Cited

OTHER PUBLICATIONS

Ohlsson et al., "Interleukin-1 receptor antagonist reduces mortality from endotoxin shock", Nature, vol. 348, (1990), pp. 550-552.
OI et al., "Chimeric Antibodies," Bio Techniques, (1986), 4: 214-221.
Oishi et al., "Inhibition of Neutrophil Apoptosis by Antioxidants in Culture Medium," Scand. J. Immunol., (1997), 45: 21-27.
Oliveira et al., "Fungal infections in marrow transplant recipients under antifungal prophylaxis with fluconazole", Brazilian Journal of Medical and Biological Research, vol. 35(7), (Jul. 2002), pp. 789-798.
Olopade et al., "Molecular Analysis of Deletions of the Short Arm of Chromosome 9 in Human Gliomas," Cancer Res., (1992), 52: 2523-2529.
Orita et al., "Detection of polymorphisms of human DNA by gel electrophoresis as single-strand conformation polymorphisms," Proc. Natl. Acad. Sci. USA, (1989), 86: 2766.
Owerbach et al., "Genetics of the large, external, transformation-sensitive (LETS) protein: assignment of a gene coding for expression of LETS to human chromosome 8," Proc. Natl. Acad. Sci. USA, (1978), 75: 5640-5644.
Padlan, "A possible procedure for reducing the immunogenicity of antibody variable domains while preserving their ligand-binding properties," Molecular Immunology, (1991), 28(4/5): 489-498.
Pajunen et al. "Assignment of the gene coding for both the beta-subunit of prolyl 4-hydroxylase and the enzyme disulfide isomerase to human chromosome region 17p11—qter," Cytogenet. Cell Genet., ( 1988), 47: 37-41 (Abstract).
Perry-O'Keefe et al., "Peptide nucleic acid pre-gel hybridization: An alternative to Southern?hybridization," Proc. Natl. Acad. Sci. USA, (1996), 93: 14670-675.
Persic et al., "An integrated vector system for the eukaryotic expression of antibodies or their fragments after selection from phage display libraries", Gene, vol. 187(1), (1997), pp. 9-18.
Peschon et al., "TNF receptor-deficient mice reveal divergent roles for p55 and p75 in several models of inflammation", J. Immunol., vol. 160, (1998), pp. 943-952.
Petersen et al., A PNA-DNA linker synthesis of N-((4,4?-dimethoxytrityloxy)ethyl)-N-(thymin-1-ylacetyl)glycine, Bioorganic Med. Chem. Lett., (1995), 5: 1119-1124.
Pfeffer et al., "mice deficient for the 55 kd tumor necrosis factor receptor are resistant to endotoxic shock, yet succumb to L. monocytogenes infection", Cell, vol. 73, (1993) pp. 457-467.
Pinkert et al., "An albumin enhancer located 10 kb upstream functions along with its promoter to direct efficient, liver-specific expression in transgenic mice," Genes Dev., (1987), 1: 268-277.
Pittelkow & Scott, "New Techniques for the In Vitro Culture of Human Skin Keratinocytes and Perspectives on Their Use for Grafting of Patients With Extensive Burns," Mayo Clinic Proc., (1986), 61: 771.
Prosser, "Detecting single-base mutations," Tibtech, (1993), 11: 238-246.
Bouchon et al, Journal of Immunology, "Cutting Edge: Inflammatory Responses Can Be Triggered by TERM-1, A Novel Receptor Expressed on Neutrophils and Monocytes", 2000, vol. 164, No. 10, pp. 4991-4995.
Bouchon et al, Nature, "TREM-1 Amplifies Inflammation and Is a Crucial Mediator of Septic Shock", 2001, vol. 410, Number , pp. 1103-1107.
J. Phua et al, European Respiratory Journal, "Soluble Triggering Receptor Expressed on Myeloid Cells-1 in Acute Respiratory Infections", 2006, vol. 28, Number , pp. 695-702.
Jun Kuai et al, Rheumatology, "TREM-1 Expression Is Increased in the Synovium of Rheumatoid Arthritis Patients and Induces the Expression of Pro-Inflammatory Cytokines", 2009, vol. 48, Number , pp. 1352-1358.
Mirjam Schenk, Journal of Clinical Investigation, "TREM-1—Expressing Intestinal Macrophages Crucially Amplify Chronic Inflammation in Experimental Colitis and Inflammatory Bowel Diseases", 2007, vol. 117, Number , pp. 3097-3106.

Yousuke Murakami et al, Arthritis and Rheumatism, "Intervention of an Inflammation Amplifier, Triggering Receptor Expressed on Myeloid Cells 1, for Treatment of Autoimmune Arthritis", 2009, vol. 60, No. 6, pp. 1615-1623.
LS Bio/LifeSpan BioSciences, Inc., Pglyrpl / pgrp antibody (Is-c579) http://www.lsbio.com/Antibodies/PGLYRP1-PGRP-Antibody-LS-C579/2801.
LS Bio/LifeSpan BioSciences, Inc,Pglyrp1 / pgrp antibody (Is-c38137) http://www.lsbio.com/Antibodies/PGLYRP1-PGRP-Antibody-LS-C38137/37645.
LS Bio/LifeSpan BioSciences, Inc.,Pglyrp1 1 pgrp antibody (Is-c578) http://www.lsbio.com/Antibodies/PGLYRP1-PGRP-Antibody-LS-C578/2800.
Ghosh Amit et al.,A Novel Antimicrobial Peptidoglycan Recognition Protein in the Cornea, Journal:Invest. Ophthalmol. Vis. Sci. Year Sep. 2009 vol. 50 No. 9 pp. 4185-4191.
Dziarski Roman et al. , Mammalian peptidoglycan recognition proteins (PGRPs) in innate immunity, Journal Innate Immunity, Year 2010, vol. 16 No. 3, pp. 168-174,.
LS Bio/LifeSpan BioSciences, Inc.,Pglyrp1 / pgrp antibody (Is-b4940), http://www.lsbio.com/Antibodies/PGLYRP1-PGRP-Antibody-LS-B4940/128350.
Abcam,Anti-PGRPS antibody [188C424] (ab13903), http://www.abcam.com/PGRPS-antibody-188C424-ab13903.html.
Kang Daiwu et al.,A peptidoglycan recognition protein in innate immunity conserved from insects to humans, Journal :Proc. Natl. Acad. Sci. USA, Year 1998, vol. 95, pp. 10078-10082.
Haselmayer Phillipp et al. TREM-1 ligand expression on platelets enhances neutrophil activation, Journal : Blood, Year 2007 vol. 110,pp. 1029-1035.
Dziarski Roman et al, Peptidoglycan recognition in innate immunity, Journal :Innate Immunity, Year Oct. 2005 vol. 11 No. 5 pp. 304-310.
Pant S.D. et al,Bovine PGLYRP1 polymorphisms and their association with resistance to Mycobacterium avium ssp. paratuberculosis, Journal :Animal Genetics, Year Aug. 20, 2010, vol. 42, pp. 354-360.
Dziarski Roman et al.The peptidoglycan recognition proteins (PGRPs), Journal :Genome Biology Year 2006, vol. 7 pp. 232.1-232.13.
Steiner Hakan , Peptidoglycan recognition proteins:On and off switches for innate immunity, Journal :Immunological Reviews , Year 2004, vol. 198 pp. 83-96.
Larin Sergey S et al .Immunotherapy with autologous tumor cells engineered to secrete Tag7/PGRP, an innate immunity recognition molecule, Journal :The Journal of Gene Medicine Year 2004;vol. 6 pp. 798-808.
Kang Daiwu et al,.A peptidoglycan recognition protein in innate immunity conserved from insects to humans, Journal: Proc. Natl. Acad. Sci. USA, Year Aug. 1998, vol. 95, pp. 10078-10082.
Guan Rongjin et al ,Crystal Structure of Human Peptidoglycan Recognition Protein S (PGRP-S) at 1.70 A Resolution, Journal :Journal of Molecular Biology.Year 2005, vol. 347,pp. 683-691.
A. Osanai et al.,Mouse Peptidoglycan Recognition Protein PGLYRP-1 Plays a Role in the Host Innate Immune Response against Listeria monocytogenes Infection, Journal: INFECTION and IMMUNITY,Year Dec. 6, 2010 vol. 79, No. 2, pp. 858-866, XP055060881.
Gimano D Amatngalim et al: Cathelicidin Peptide LL-37 Modulates TREM-1 Expression and Inflammatory Responses to Microbial Compounds,Journal : INFLAMMATION, Year,Sep. 2, 2010, vol. 34, No. 5 pp. 412-425.
Arts Rob J W et al: "TREM-1 interaction with the LPS/TLR4 receptor complex.", Journal :European Cytokine Network,Year Mar. 2011, vol. 22, No. 1.pp. 11-14.
S. Gibot et al. Modulation of the Triggering Receptor Expressed on the Myeloid Cell Type 1 Pathway in Murine Septic Shock,Journal: INFECTION and IMMUNITY,Year May 1 2006 vol. 74, No. 5,pp. 2823-2830.
Ramanathan B et al: Cloning of porcine triggering receptor expressed on myeloid cells-1 (TREM-1) and its induction by lipopolysaccharide, peptidoglycan, and *Salmonella* entérica serovar Typhimurium, infection. ( 2004).

(56) References Cited

OTHER PUBLICATIONS

Thekla Poukoulidou et al. TREM-1 expression on neutrophils and monocytes of septic patients: relation to the underlying infection and the implicated pathogen,Journal : BMC Infectious Diseases, Year Nov. 4, 2011 vol. 11, No. 1, p. 309(1-8).

Julien Royet et al: "Peptidoglycan recognition proteins: modulators of the microbiome and inflammation",Journal: Nature Reviews Immunology,Year :Dec. 2011 pp. 837-851.

Dziarski R, Peptidoglycan recognition proteins (PGRPs), Journal :Molecular Immunology, Year 2004, vol. 40 pp. 877-886.

Saha et al., PGLYRP-2 and Nod2 Are Both Required for Peptidoglycan-Induced Arthritis and Local Inflammation, Journal :Cell Host & Microbe, Year 2009,vol. 5 pp. 137-150.

Saha et al.Peptidoglycan Recognition Proteins Protect Mice from Experimental Colitis by Promoting Normal Gut Flora and Preventing Induction of Interferon-y, Journal : Cell Host and Microbe, Year 2010, vol. 8, pp. 147-162.

* cited by examiner

```
                2         3         4         5         6         7
           789012345678901234567890123456789012345678901234567890123456
humanTREM-1 ELRAATKLTEEKYELKEGQTLD     T EKFASSQKAWQIIRDGEMPKTLACTERPSKN
cynoTREM-1     TTELTEEKYEYKEGQTLE  K  A EKYANSRKAWQKM-EGKMPKILAKTERPSEN
            :*:******* ******:*****:***:*.*.****  : :*;*** ** *****:*

8         9        10        11        12        13
           789012345678901234567890123456789012345678901234567890123456
humanTREM-1 SHPVQVGRIILEDYH  GLLRVRMVNLQVEDSGLYQCVIYQPPKEPHMLFDRIRLVVTKG
cynoTREM-1 SHPVQVGRITLEDYPDHGLLQVQMTNLQVEDSGLYQCVIYQHPKESHVLFNPICLVVTKG
           ********* **** *****.*.*.**************** ***.*:**: * ******

14        15        16        17        18        19
           789012345678901234567890123456789012345678901234567890123456
humanTREM-1 FSGTPGSNENSTQNVYKIPPTTTKALCPLYTSPRTVTQAPPKSTADVSTPDSEINLTNVT
cynoTREM-1 SSGTPGSSENSTQNVYRTPSTTAKALGPRYTSPRTVTQAPPESTVVVSTPGSEINLTNVT
           ******.*******. *.**:*** * *************:**. ****.**********

20
           7890
humanTREM-1 DIIR
cynoTREM-1 DIIR
           ****
```

ANTIBODIES THAT BIND AND BLOCK TRIGGERING RECEPTOR EXPRESSED ON MYELOID CELLS-1 (TREM-1)

CROSS-REFERENCE TO RELATED APPLICATIONS

This application claims priority under 35 U.S.C. §119 of U.S. Provisional Applications 61/598,968, filed Feb. 15, 2012, 61/599,447, filed Feb. 16, 2012, 61/672,799, filed Jul. 18, 2012, 61/674,434, filed Jul. 23, 2012; this application further claims priority of European Applications 12155641.9, filed Feb. 15, 2012, Ser. No. 12/158,974.1, filed Mar. 12, 2012, Ser. No. 12/176,892.3, filed Jul. 18, 2012; the contents of all above-named applications are incorporated herein by reference.

FIELD OF THE INVENTION

The present invention relates to a method of identifying a functional TREM-1 antibody. The invention also relates to antibodies that are capable of specifically binding TREM-1 and which are capable of reducing or blocking TREM-1 activity (signalling and/or activation). Furthermore, the invention relates to uses for such antibodies, such as therapeutic and pharmaceutical uses.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Nov. 30, 2012. The Sequence Listing is made up of 39 kilobytes, and the information contained in the attached "SEQUENCE LISTING" is identical to the information in the specification as originally filed. No new matter is added.

BACKGROUND OF THE INVENTION

Triggering receptor expressed on myeloid cells-1 (TREM-1) is a receptor that is expressed on monocytes, macrophages and neutrophils. When activated, TREM-1 associates with a signalling protein, DAP12, and triggers the release of pro-inflammatory cytokines from the cells that express it (Bouchon et al, J. Immunol. 2000; 164(10): 4991-4995). TREM-1 mRNA and protein expression is known to be upregulated in the myeloid cells of individuals with sepsis, rheumatoid arthritis (RA) and inflammatory bowel disease (IBD). Increasing scientific evidence supports the theory that TREM-1 contributes to the development and progression of inflammatory diseases, as TREM-1 positive monocytes and neutrophils that are recruited to an inflamed area exacerbate inflammation (Bouchon et al. Nature 2001; 410: 1103-1107; Schenk et al, Clin Invest. 2007; 117(10): 3097-3106); Kuai et al., Rheumatology (Oxford). 2009; 48(11):1352-1358.

Antibodies that are capable of binding TREM-1 are known, including the commercially available TREM26 and TREM37 (cat. nos. 314902 and 316102, respectively, Biolegend, San Diego, Calif. 92121, USA), MAB1278 (cat. no. MAB1278, R&D Systems, Minneapolis, Minn. 55413, USA), mAb 6B1 (cat. no. HM2252, Hycult Biotech, Uden, Netherlands) and anti-TREM-1 2E2 (cat. no. HPA005563, Sigma-Aldrich, Denmark). All known TREM-1 antibodies are agonistic when immobilised; that is, they increase cytokine release from monocytes, macrophages and neutrophils. Another characteristic of the known TREM-1 antibodies is that they do not cross-react with TREM-1 from primates, such as cynomolgus monkeys or rhesus monkeys, which means that the known antibodies cannot be tested in these animals.

Thus, there is a need in the art for an antibody that is capable of binding and blocking the function of TREM-1. There is a need in the art for a TREM-1 antibody that is capable of preventing TREM-1 from forming dimers/multimers. There is a need in the art for a TREM-1 antibody that is capable of blocking TREM-1 activation and signalling. There is a need in the art for a TREM-1 antibody that is capable of interfering with the interaction between TREM-1 and its ligand. There is a need in the art for a TREM-1 antibody that is capable of blocking cytokine release from a myeloid cell. There is a need in the art for a TREM-1 antibody that has little or no agonistic activity when soluble or immobilised. There is also a need in the art for an antibody that is capable of binding both human TREM-1 and TREM-1 from one or more other species, such as a primate, in order to enable toxicology investigation as well as assess the pharmacokinetics and pharmacodynamics of the antibody in suitable animal models.

Disclosed herein are TREM-1 antibodies that are suitable for use as pharmaceuticals. Such antibodies may have a substantial impact upon the quality of life of individuals with sepsis or a chronic inflammatory disease such as rheumatoid arthritis, psoriatic arthritis and inflammatory bowel disease.

SUMMARY

The present invention relates to a method of identifying a functional TREM-1 antibody, comprising (a) culturing a first cell expressing TREM-1, a signalling protein and a reporter construct; (b) measuring the activity of the first cell when said cell is incubated with a TREM-1 modifying agent; (c) contacting the co-culture of (b) with a TREM-1 antibody; and (d) measuring that the activity of the first cell is less than or more than the activity measured in (b).

The method may be tailored to identify a blocking TREM-1 molecule, such as an antibody. The method of identifying a blocking TREM-1 antibody comprises (a) culturing a first cell expressing TREM-1, a signalling protein and a reporter construct; (b) measuring the activity of the first cell when said cell is incubated with an activating compound, such as a TREM-1 ligand, or an activated neutrophil; (c) contacting the co-culture of the first cell and the activating compound, such as a TREM-1 ligand, or an activated neutrophil with a TREM-1 antibody; and (d) measuring that the activity of the first cell is less than the activity measured in (b).

The method may be tailored to identify a stimulating TREM-1 antibody. The method of identifying a stimulating TREM-1 antibody comprises (a) culturing a first cell expressing TREM-1, a signalling protein and a reporter construct; (b) measuring the activity of the first cell; (c) contacting/incubating said cell with a TREM-1 antibody; and (d) measuring that the activity of the first cell is more than the activity of the measured in (b).

The first cell may be of haematopoetic origin. The modifying agent of (b) may be an activated neutrophil or a TREM-1 ligand. The signalling protein may be DAP10, DAP12, TCR zeta, Fc gamma RIII and an Fc receptor, or a portion thereof. The signalling protein may signal via a transcription factor such as NFAT or NFκB. The reporter gene may be a gene that is not natively expressed in said first cell and may be a gene that encodes β-galactosidase, luciferase, green fluorescent protein (GFP) or chloramphenicol transferase. The present invention also relates to stimulating TREM-1 antibodies that may be identified by means of the invented method.

The present invention relates to antibodies that are capable of specifically binding to TREM-1 and that are capable of blocking TREM-1 function. Said antibodies may be capable of preventing or reducing the dimerisation or multimerisation of TREM-1. Said antibodies may be capable of blocking the interaction between TREM-1 and its ligand, or the antibodies may be capable of blocking the TREM-1 function that is induced by a TREM-1 ligand. The TREM-1 may be human TREM-1 and/or TREM-1 from another species than a human, such as TREM-1 from another primate than a human.

Antibodies of the invention may be capable of competing with mAb 0170 for binding to human TREM-1. Antibodies of the invention may be capable of specifically binding a polypeptide comprising amino acids D38 to F48 of SEQ ID NO: 1 (human TREM-1). Antibodies of the invention may have an epitope comprising one, two, three, four, five, six, seven or all of the amino acid residues selected from the group consisting of the D38, V39, K40, C41, D42, Y43, T44 and L45 of SEQ ID NO: 1 (human TREM-1) and one, two or all of the amino acid residues selected from the group consisting of the E46, K47 and F48 of SEQ ID NO: 1 (human TREM-1), as may be determined using HX-MS. Antibodies of the invention may have an epitope comprising one, two, three or all of the amino acid residues selected from the group consisting of the D42, E46, D92 and H93 of SEQ ID NO: 1 (human TREM-1), as may be determined by measuring antibody binding to variants of TREM-1.

Antibodies of the invention may be capable of competing with mAb 0170 for binding to cynomolgus monkey TREM-1. Antibodies of the invention may be capable of capable of specifically binding a polypeptide comprising amino acids E19 to L26 of cynomolgus monkey TREM-1 (SEQ ID NO: 12), or the corresponding amino acids of SEQ ID NO: 21, as may be determined using HX-MS.

Antibodies of the invention may be used as pharmaceuticals for the treatment of individuals with one or more autoimmune diseases and/or chronic inflammation. Hence, the present invention also relates to a method of treatment of individuals with one or more autoimmune diseases and/or chronic inflammation.

BRIEF DESCRIPTION OF THE DRAWINGS

FIG. 7: Sequence coverage of HX analyzed peptides of hTREM-1 in the presence and absence of mAb 0023 or mAb 0026 (A), mAb 0024 or Biolegend Clone 26 (B), mAb 0025 (C) or RnD Biosystems' MAB1278 (D). The primary sequence is displayed above the HX analyzed peptides (shown as horizontal bars). Peptides showing similar exchange patterns both in the presence and absence of mAbs are displayed in white, whereas peptides showing reduced deuterium incorporation upon mAb binding are coloured black. Boxed sequence regions define the epitope.

FIG. 11: The human TREM-1 (residues 17 through 200 of SEQ ID NO:1) and cynomolgus monkey (residues 2-180 of SEQ ID NO:12) TREM-1 sequences are aligned. Amino acid residues that differ between the two are shown in bold type.

Figure 1:
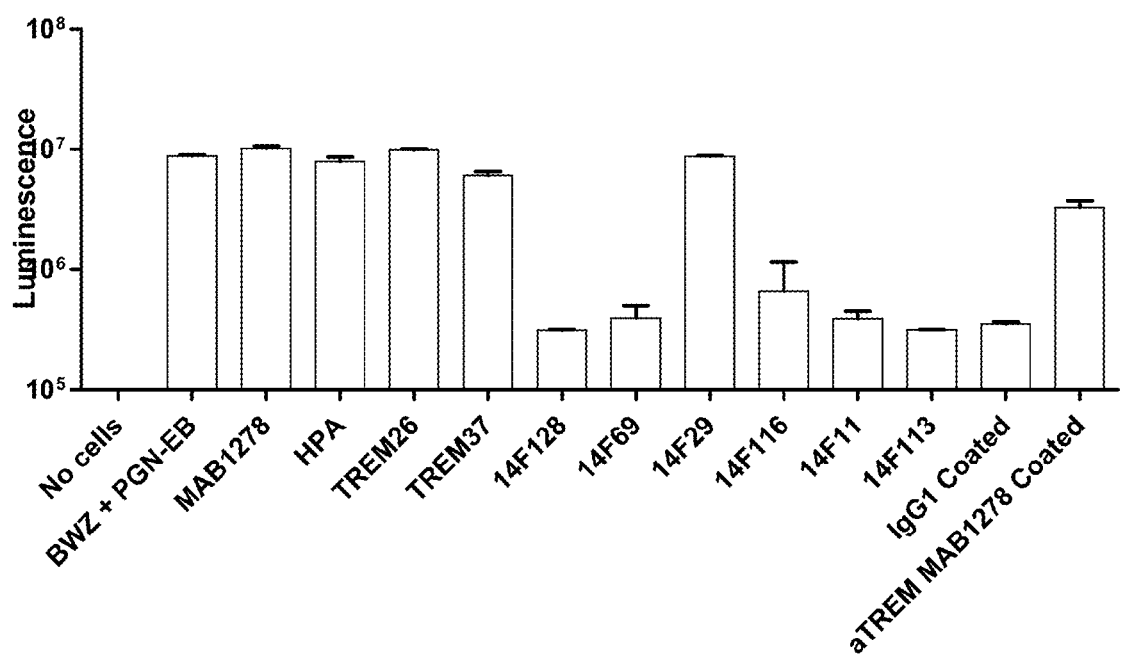
FIG. 1: Activation of the BWZ.36/hTREM-1:DAP12:NFAT-LacZ cell line (herein also referred to as the "BWZ/hTREM-1 reporter cell") is reduced by antibodies such as 14F128 and 14F113 but not by the commercially available antibodies MAB1278 MAB1278 (R&D Systems, Minneapolis, Minn. 55413, USA: Cat. No. MAB1278), anti-TREM-1 HPA (Sigma, USA: Cat. No. HPA005563), aTREM26 (Biolegend, San Diego, Calif. 92121, USA: Cat. No. 314902) and aTREM37 (Biolegend, San Diego, Calif. 92121, USA: Cat. No. 316102).
Figure 2:
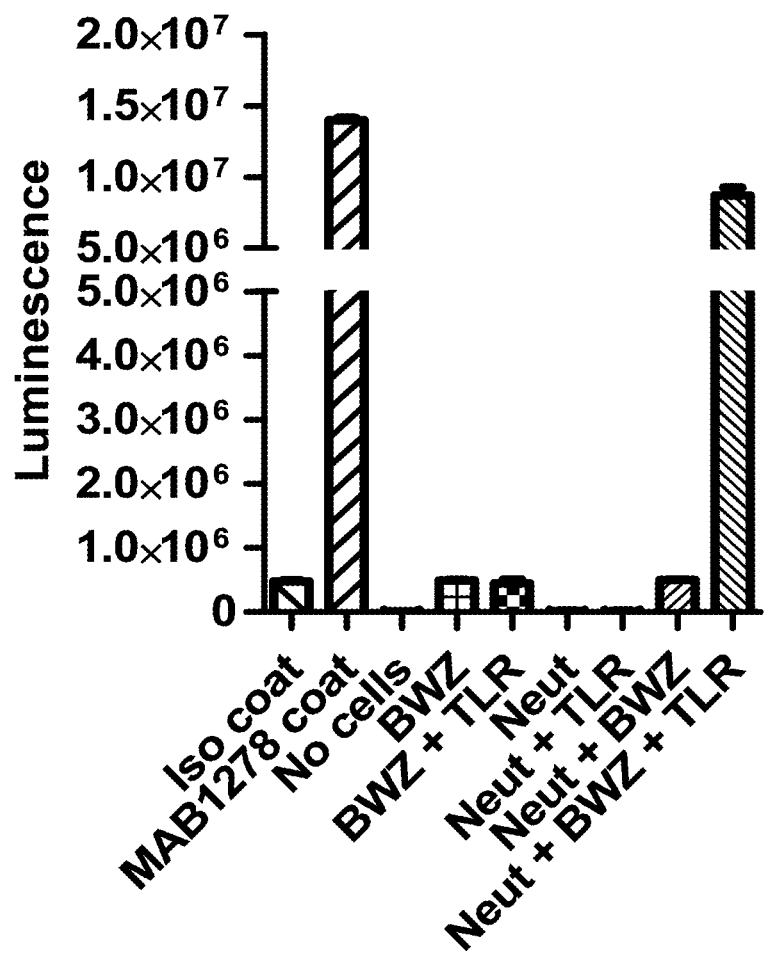
FIG. 2: The BWZ/hTREM-1 reporter cell alone or co-cultured with TLRL pre-stimulated neutrophils. TLRL activated neutrophils are able to induce a 15-fold increase in the signal (luminescence), compared to non-activated neutrophils (see the last two columns). The positive control (the platebound, agonistic MAB1278 (R&D Systems, Minneapolis, Minn. 55413, USA: Cat. no. MAB1278) gave a 32-fold induction in this experiment (see second column). Data are plotted as means±SEM (n=3).

Residues that have been shown to be within the epitope (as determined using HX-MS and surface plasmon resonance) are highlighted.

BRIEF DESCRIPTION OF THE SEQUENCES

SEQ ID NO: 1 represents the amino acid sequence of wild type (wt) human TREM-1.

SEQ ID NO: 2 represents the amino acid sequence of the variable heavy chain of the m14F69 antibody.

SEQ ID NO: 3 represents the amino acid sequence of the variable light chain of the m14F69 antibody.

SEQ ID NO: 4 represents the amino acid sequence of the heavy chain of a first humanised TREM-1 antibody (mAb 0170).

SEQ ID NO: 5 represents the amino acid sequence of the light chain of a first humanised TREM-1 antibody (mAB 0170).

SEQ ID NO: 6 represents the amino acid sequence of the heavy chain of a second humanised TREM-1 antibody (mAb 0122).

SEQ ID NO: 7 represents the amino acid sequence of the light chain of a second humanised TREM-1 antibody (mAb 0122).

SEQ ID NO: 8 represents the amino acid sequence of the heavy chain of the m14F128 antibody.

SEQ ID NO: 9 represents the amino acid sequence of the light chain of the m14F128 antibody.

SEQ ID NO: 10 represents the amino acid sequence of the heavy chain of the m14F113 antibody.

SEQ ID NO: 11 represents the amino acid sequence of the light chain of the m14F113 antibody.

SEQ ID NO: 12 represents the amino acid sequence of the extracellular domain of wild type (wt) cynomolgus monkey (c) TREM-1, when expressed in E. coli.

SEQ ID NO: 13 represents the amino acid sequence of K20A-hTREM-1-Cmyc2-His6 (construct 0222).

SEQ ID NO: 14 represents the amino acid sequence of A24T/Y28F/N30S/R32Q/P70H-cTREM-1-Cmyc2-His6 (construct 0244).

SEQ ID NO: 15 represents the amino acid sequence of A24T/Y28F/N30S/R32Q/E54K-cTREM-1-Cmyc2-His6 (construct 0245).

SEQ ID NO: 16 represents the nucleic acid sequence of a primer.

SEQ ID NO: 17 represents the nucleic acid sequence of a primer.

SEQ ID NO: 18 represents the amino acid sequence of human (h) TREM-1(1-134)-His 6.

SEQ ID NO: 19 represents the amino acid sequence of cTREM-1-Cmyc2-His6 (construct 0238).

SEQ ID NO: 20 represents the amino acid sequence of hTREM-1-Cmyc2-His6 (construct 0247).

SEQ ID NO: 21 represents the amino acid sequence of full length cTREM-1.

SEQ ID NO: 22 represents the amino acid sequence of full length murine (m) TREM-1.

SEQ ID NO: 23 represents the amino acid sequence of full length hPGLYRP1.

DESCRIPTION

TREM-1 is a transmembrane protein that consists of 234 amino acids, including a single extracellular immunoglobulin domain and a short cytoplasmic tail with no apparent signaling motif. When activated, TREM-1 associates with the ITAM-containing signaling adaptor protein, DAP12. Downstream signalling may include activation of the NFAT transcription factor, causing an upregulation of pro-inflammatory cytokine production.

The present invention relates to antibodies that are capable of specifically binding and blocking the function of TREM-1. Antibodies of the invention may block TREM-1 function by reducing/blocking TREM-1 activation and downstream signalling.

Antibodies according to the invention may block TREM-1 by means of one of one or a combination of several different mechanisms, blocking TREM-1 directly or indirectly. For example, antibodies of the invention may prevent the natural ligand of TREM-1, peptidoglycan recognition protein 1 (PGLYRP1), from creating a functional complex with TREM-1 and/or antibodies of the invention may block TREM-1 by preventing individual TREM-1 molecules from forming dimers or multimers. TREM-1 dimerisation or multimerisation may be reduced or prevented by TREM-1 antibodies that are capable of binding to a portion of TREM-1 that would otherwise reside in the interface of a TREM-1 dimer, thus preventing individual TREM-1 molecules from associating with one another. TREM-1 dimerisation or multimerisation may be reduced or prevented by TREM-1 antibodies that interfere with the interaction of TREM-1 with its ligand. Antibodies according to the current invention may block PGLYRP1-induced activation of TREM-1. PGLYRP1, a highly conserved, 196 amino acid long protein consisting of a signal peptide and a peptidoglycan binding domain, is expressed in neutrophils and released upon their activation. Antibodies according to the current invention may downregulate pro-inflammatory cytokine release from myeloid cells. Antibodies according to the current invention may block the release of TNFalpha, MIP-1beta, MCP-1, IL-1beta, GM.CSF, IL-6 and/or IL-8 from macrophages, neutrophils, synovial tissue cells and/or a reporter cell, as disclosed herein.

Antibodies of the invention may be capable of binding both human TREM-1 and TREM-1 from another species than a human being. The term "TREM-1", as used herein, thus encompasses any naturally occurring form of TREM-1 which may be derived from any suitable organism. For example, TREM-1 for use as described herein may be vertebrate TREM-1, such as mammalian TREM-1, such as TREM-1 from a primate (such as a human, a chimpanzee, a cynomolgus monkey or a rhesus monkey); a rodent (such as a mouse or a rat), a lagomorph (such as a rabbit), or an artiodactyl (such a cow, sheep, pig or camel). Preferably, the TREM-1 is SEQ ID NO: 1 (human TREM-1). The TREM-1 may be a mature form of TREM-1 such as a TREM-1 protein that has undergone post-translational processing within a suitable cell. Such a mature TREM-1 protein may, for example, be glycosylated. The TREM-1 may be a full length TREM-1 protein.

Antibodies of the invention may be monoclonal antibodies, in the sense that they are directly or indirectly derived from a single clone of a B lymphocyte. TREM-1 antibodies may be produced, screened and purified using, for example, the methods described in the Examples. In brief, a suitable mouse such as a TREM-1 or TREM-1/TREM-3 knock-out (KO) mouse may be immunised with TREM-1, a cell expressing TREM-1 or a combination of both.

Antibodies of the invention may be polyclonal in the sense of being a mixture of monoclonal antibodies according to the current invention.

Primary screening of hybridoma supernatants may be performed using direct ELISA or FMAT and secondary screening may be performed using flow cytometry. Positive hybridoma supernatants may then be screened in a reporter gene assay.

Antibodies may be recombinantly expressed in prokaryotic or eukaryotic cells. The prokaryotic cell may be E. coli. The eukaryotic cell may be a yeast, insect or mammalian cell, such as a cell derived from an organism that is a primate (such as a human, a chimpanzee, a cynomolgus monkey or a rhesus monkey), a rodent (such as a mouse or a rat), a lagomorph (such as a rabbit) or an artiodactyl (such a cow, sheep, pig or camel). Suitable mammalian cell lines include, but are not limited to, HEK293 cells, CHO cells and HELA cells. TREM-1 antibodies may also be produced by means of other methods known to the person skilled in the art, such as a phage display or a yeast display.

Once produced, antibodies may be screened for binding to, for example, full length TREM-1 or mutants thereof using the methods described in the Examples.

One embodiment of the current invention is a method of identifying a functional TREM-1 antibody. Antibodies that are capable of specifically binding TREM-1 and that have any effect upon TREM-1 activation and downstream signalling are herein referred to as "functional TREM-1 antibodies". A "functional" TREM-1 antibody herein refers to an antibody that is capable of blocking or stimulating TREM-1. The method of identifying a functional TREM-1 antibody comprises (a) culturing a first cell expressing TREM-1, a signalling protein and a reporter construct; (b) measuring the activity of the first cell when said cell is incubated with a TREM-1 modifying agent; (c) contacting the co-culture of (b) with a TREM-1 antibody; and (d) measuring that the activity of the first cell is less than or more than the activity measured in (b).

The "first cell" of (a) may be a cell of haematopoetic origin, such as a myeloid cell, such as a T-cell. The signalling protein of (a) may be any signalling protein that is capable of forming a complex with TREM-1. Suitable signalling proteins include DAP10, DAP12, TCR zeta, Fc gamma RIII and an Fc receptor, or part thereof. The reporter construct of (a) may be any construct that is capable of being activated via the signalling protein and generating a recognisable signal. Suitable reporter constructs comprise a transcription factor and a reporter gene. The signalling protein may signal via a transcription factor selected from the group consisting of the NFAT and NFkB. The reporter gene is a gene that is not natively expressed in said first cell and may be a gene that encodes β-galactosidase, luciferase, green fluorescent protein (GFP) or chloramphenicol transferase. Said first cell may be transfected with a transcription factor and a reporter gene using methods that are well known in the art.

The "BWZ/hTREM-1 reporter cell" described in the Examples is one example of a "first cell".

The modifying agent of (b) may be a TREM-1 ligand or an activated neutrophil. The "TREM-1 antibody" of (c) may be a TREM-1 specific hybridoma supernatant or a purified antibody. The activity measured in (d) is the signal produced by the reporter construct. An example of such signalling is the luminescence caused by NFAT-driven LacZ (R-lactamase luciferase) production.

The method may be tailored to identify a blocking TREM-1 antibody. The method of identifying a blocking TREM-1 antibody comprises (a) culturing a first cell expressing TREM-1, a signalling protein and a reporter construct; (b) measuring the activity of the first cell when said cell is incubated with an activated neutrophil; (c) contacting the co-culture of the first cell and the activated neutrophil with a TREM-1 antibody; and (d) measuring that the activity of the first cell is less than the activity measured in (b).

The method may also be tailored to identify a stimulating TREM-1 antibody. The method of identifying a stimulating TREM-1 antibody comprises (a) culturing a first cell expressing TREM-1, a signalling protein and a reporter construct; (b) measuring the activity of the first cell; (c) contacting/incubating said cell with a TREM-1 antibody; and (d) measuring that the activity of the first cell is more than the activity of the measured in (b).

The present invention relates to blocking TREM-1 antibodies that may be identified by means of the method, herein disclosed, of identifying a blocking antibody. When tested using the method described above and in the Examples, an antibody according to the current invention may, at a concentration of less than 100 μg/ml—such as less than 90 μg/ml, such as less than 80 μg/ml, such as less than 70 μg/ml, such as less than 60 μg/ml, such as less than 50 μg/ml, such as less than 40 μg/ml, such as less than 30 μg/ml, such as less than 20 μg/ml, such as less than 10 μg/ml, such as less than 5 μg/ml, such as less than 1 μg/ml—be capable of reducing the activity of said first cell by 50%, such as 60%, such as 70%, such as 80%, such as 90%, such as 95%, such as 100%. An antibody according to the invention may be capable of completely extinguishing the activity of the first cell. When tested using the method described above and in the Examples, an antibody according to the current invention may, at a concentration of less than 1 μg/ml—such as less than 0.9 μg/ml, such as less than 0.8 μg/ml, such as less than 0.7 μg/ml, such as less than 0.6 μg/ml, such as less than 0.5 μg/ml, such as less than 0.4 μg/ml, such as less than 0.3 μg/ml, such as less than 0.2 μg/ml—be capable of extinguishing the activity of the first cell.

The present invention also relates to blocking TREM-1 antibodies that may be identified by other means than the method herein disclosed.

The term "antibody" herein refers to a protein, derived from a germline immunoglobulin sequence, which is capable of specifically binding to an antigen (TREM-1) or a portion thereof. The term includes full length antibodies of any class or isotype (that is, IgA, IgE, IgG, IgM and/or IgY) and any single chain or fragment thereof. An antibody that specifically binds to an antigen, or portion thereof, may bind exclusively to that antigen, or portion thereof, or it may bind to a limited number of homologous antigens, or portions thereof. Full-length antibodies usually comprise at least four polypeptide chains: two heavy (H) chains and two light (L) chains that are interconnected by disulfide bonds. One immunoglobulin subclass of particular pharmaceutical interest is the IgG family. In humans, the IgG class may be sub-divided into 4 subclasses: IgG1, IgG2, IgG3 and IgG4, based on the sequence of their heavy chain constant regions. The light chains can be divided into two types, kappa and lambda, based on differences in their sequence composition. IgG molecules are composed of two heavy chains, interlinked by two or more disulfide bonds, and two light chains, each attached to a heavy chain by a disulfide bond. A heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The hypervariable regions of the heavy and light chains form a [binding] domain that is capable of interacting with an antigen, whilst the constant region of an antibody may mediate binding of the immunoglobulin to host tissues or factors, including but not limited to various cells of the immune system (effector cells), Fc receptors and the first component (Clq) of the classical complement system.

Antibodies of the current invention may be isolated. The term "isolated antibody" refers to an antibody that has been separated and/or recovered from (an) other component(s) in the environment in which it was produced and/or that has been purified from a mixture of components present in the environment in which it was produced.

Certain antigen-binding fragments of antibodies may be suitable in the context of the current invention, as it has been shown that the antigen-binding function of an antibody can be performed by fragments of a full-length antibody. The term "antigen-binding fragment" of an antibody refers to one or more fragment(s) of an antibody that retain the ability to specifically bind to an antigen, such as TREM-1, as described herein. Examples of antigen-binding fragments include Fab, Fab', F(ab)2, F(ab')2, F(ab)S, Fv (typically the VL and VH domains of a single arm of an antibody), single-chain Fv (scFv; see e.g. Bird et al., Science 1988; 242:42 S-426; and Huston et al. PNAS 1988; 85:5879-5883), dsFv, Fd (typically the VH and CH1 domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al., Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 2S:1126-1136; WO2005040219, and published U.S. Patent Applications 20050238646 and 20020161201. These antibody fragments may be obtained using conventional techniques known to those of skill in the art, and the fragments may be screened for utility in the same manner as intact antibodies.

An antibody of the invention may be a human antibody or a humanised antibody. The term "human antibody", as used herein, is intended to include antibodies having variable regions in which at least a portion of a framework region and/or at least a portion of a CDR region are derived from human germline immunoglobulin sequences. (For example, a human antibody may have variable regions in which both the framework and CDR regions are derived from human germline immunoglobulin sequences.) Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivative" refers to any modified form of the human antibody, such as a conjugate of the antibody and another agent or antibody.

The term "humanised antibody", as used herein, refers to a human/non-human chimeric antibody that contains one or more sequences (CDR regions or parts thereof) that are derived from a non-human immunoglobulin. A humanised antibody is, thus, a human immunoglobulin (recipient antibody) in which at least residues from a hyper-variable region of the recipient are replaced by residues from a hyper-variable region of an antibody from a non-human species (donor antibody) such as from a mouse, rat, rabbit or non-human primate, which have the desired specificity, affinity, sequence composition and functionality. In some instances, FR residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. C. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introdution (backmutation) of the amino acid residue from the donor antibody has beneficial impact on the properties of the humanised antibody. In addition to donor antibody derived backmutations, the humanised antibody can be engineered by introduction of germline residues in the CDR or framework regions, elimination of immunogenic epitopes, site-directed mutagenesis, affinity maturation, etc.

Furthermore, humanised antibodies may comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and another agent or antibody.

The term "chimeric antibody", as used herein, refers to an antibody whose light and heavy chain genes have been constructed, typically by genetic engineering, from immunoglobulin variable and constant region genes that originate from different species. For example, the variable segments of genes from a mouse monoclonal antibody may be joined to human constant segments.

The fragment crystallisable region ("Fc region"/"Fc domain") of an antibody is the N-terminal region of an antibody, which comprises the constant CH2 and CH3 domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprises one or more, and perhaps all of the following mutations that will result in decreased affinity to certain Fc receptors (L234A, L235E, and G237A) and in reduced C1q-mediated complement fixation (A330S and P331S), respectively (residue numbering according to the EU index).

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CH1 is modified such that the number of cysteine residues in the hinge region is altered, e.g., increased or decreased. This approach is described further for instance in U.S. Pat. No. 5,677,425 by Bodmer et al.

The constant region may be modified to stabilize the antibody, e.g., to reduce the risk of a bivalent antibody separating into two monovalent VH-VL fragments. For example, in an IgG4 constant region, residue S228 (residue numbering according to the EU index) may be mutated to a proline (P) residue to stabilise inter heavy chain disulphide bridge formation at the hinge (see, e.g., Angal et al., Mol Immunol. 1995; 30: 105-8).

Antibodies or fragments thereof may also be defined in terms of their complementarity-determining regions (CDRs). The term "complementarity-determining region" or "hypervariable region", when used herein, refers to the regions of an antibody in which amino acid residues involved in antigen binding are situated. The region of hypervariability or CDRs can be identified as the regions with the highest variability in amino acid alignments of antibody variable domains. Databases can be used for CDR identification such as the Kabat database, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196: 901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

The m14F69 antibody has a variable heavy chain sequence as shown in SEQ ID NO: 2 and a variable light chain sequence as shown in SEQ ID NO: 3. An antibody of the invention may comprise this variable heavy chain sequence and/or this variable light chain sequence. The m14F69 antibody has the CDR sequences shown at amino acids 31 to 35, 50 to 68 and 101 to 110 of SEQ ID NO: 2 and amino acids 24 to 38, 54 to 60 and 93 to 101 of SEQ ID NO: 3. An antibody of the invention may comprise 1, 2, 3, 4, 5 or all 6 of these CDR sequences. An antibody of the invention may comprise amino acids 101 to 110 of SEQ ID NO: 2.

The heavy chain of an antibody according to the invention may comprise a CDR1 sequence of amino acids 31 to 35 (TYAMH) of SEQ ID NO: 2, wherein one of these amino acids may be substituted by a different amino acid.

The heavy chain of an antibody according to the invention may comprise a CDR2 sequence of amino acids 50 to 68 (RIRTKSSNYATYYADSVKD) of SEQ ID NO: 2, wherein one, two or three of these amino acids may be substituted by a different amino acid.

The heavy chain of an antibody according to the invention may comprise a CDR3 sequence of amino acids 101 to 110 (DMGQRRQFAY) of SEQ ID NO: 2, wherein one, two or three of these amino acids may be substituted by a different amino acid.

The light chain of an antibody according to the invention may comprise a CDR1 sequence of amino acids 24 to 38 (RASESVDTFDYSFLH) of SEQ ID NO: 3, wherein one, two or three of these amino acids may be substituted with a different amino acid.

The light chain of an antibody according to the invention may comprise a CDR2 sequence of amino acids 54 to 60 (RASNLES) of SEQ ID NO: 3, wherein one or two of these amino acids may be substituted with a different amino acid.

The light chain of an antibody according to the invention may comprise a CDR3 sequence of amino acids 93 to 101 (QQSNEDPYT) of SEQ ID NO: 3, wherein one or two of these amino acids may be substituted with a different amino acid.

The mAb 0170 antibody has a heavy chain sequence as shown in SEQ ID NO: 4 and a light chain sequence as shown in SEQ ID NO: 5. An antibody of the invention may comprise this heavy chain sequence and/or this light chain sequence. The mAb 0170 antibody has the CDR sequences shown at amino acids 31 to 35, 50 to 68 and 101 to 110 of SEQ ID NO: 4 and amino acids 24 to 38, 54 to 60 and 93 to 101 of SEQ ID NO: 5. An antibody of the invention may comprise 1, 2, 3, 4, 5 or all 6 of these CDR sequences.

The mAb 0122 antibody has a heavy chain sequence as shown in SEQ ID NO: 6 and a light chain sequence as shown in SEQ ID NO: 7. An antibody of the invention may comprise this heavy chain sequence and/or this light chain sequence. The mAb 0122 antibody has the CDR sequences shown at amino acids 31 to 35, 50 to 68 and 101 to 110 of SEQ ID NO: 6 and amino acids 24 to 38, 54 to 60 and 93 to 101 of SEQ ID NO: 7. An antibody of the invention may comprise 1, 2, 3, 4, 5 or all 6 of these CDR sequences.

The heavy chain of an antibody according to the invention may comprise a CDRH1 sequence of amino acids 31 to 35 (TYAMH) of SEQ ID NO: 4 or SEQ ID NO: 6, wherein one of these amino acids may be substituted by a different amino acid residue.

The heavy chain of an antibody according to the invention may comprise a CDRH2 sequence of amino acids 50 to 68 (RIRTKSSNYATYYAASVKG) of SEQ ID NO: 4 or SEQ ID NO: 6, wherein one, two or three of these amino acids may be substituted by a different amino acid.

The heavy chain of an antibody according to the invention may comprise a CDRH3 sequence of amino acids 101 to 110 (DMGIRRQFAY) of SEQ ID NO: 4, wherein one, two or three of these amino acids may be substituted by a different amino acid.

The heavy chain of an antibody according to the invention may comprise a CDRH3 sequence of amino acids 101 to 110 (DMGQRRQFAY) of SEQ ID NO: 6, wherein one, two or three of these amino acids may be substituted by a different amino acid.

The light chain of an antibody according to the invention may comprise a CDRL1 sequence of amino acids 24 to 38 (RASESVDTFDYSFLH) of SEQ ID NO: 5 or SEQ ID NO: 7, wherein one, two or three of these amino acids may be substituted with a different amino acid.

The light chain of an antibody according to the invention may comprise a CDRL2 sequence of amino acids 54 to 60 (RASNLES) of SEQ ID NO: 5 or SEQ ID NO: 7, wherein one or two of these amino acids may be substituted with a different amino acid.

The light chain of an antibody according to the invention may comprise a CDRL3 sequence of amino acids 93 to 101 (QQSNEDPYT) of SEQ ID NO: 5 or SEQ ID NO: 7, wherein one or two of these amino acids may be substituted with a different amino acid.

The m14F128 antibody has a heavy chain as shown in SEQ ID NO: 8 and a light chain as shown in SEQ ID NO: 9. An antibody of the invention may comprise this variable heavy chain sequence and/or this variable light chain sequence. The m14F128 antibody has the CDR sequences shown at amino acids 31 to 35, 50 to 68 and 101 to 110 of SEQ ID NO: 8 and amino acids 24 to 38, 54 to 60 and 93 to 101 of SEQ ID NO: 9. An antibody of the invention may comprise 1, 2, 3, 4, 5 or all 6 of these CDR sequences.

The m14F113 antibody has a heavy chain as shown in SEQ ID NO: 10 and a light chain as shown in SEQ ID NO: 11. An antibody of the invention may comprise this variable heavy chain sequence and/or this variable light chain sequence. The m14F113 antibody has the CDR sequences shown at amino acids 31 to 35, 50 to 68 and 101 to 110 of SEQ ID NO: 10 and amino acids 24 to 38, 54 to 60 and 93 to 101 of SEQ ID NO: 11. An antibody of the invention may comprise 1, 2, 3, 4, 5 or all 6 of these CDR sequences. An antibody of the invention may comprise amino acids 101 to 110 of SEQ ID NO: 10.

The term "antigen" (Ag) refers to the molecular entity used for immunization of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunization process, or other process, e.g. phage display, used for generating the Ab.

The term "epitope", as used herein, is defined in the context of a molecular interaction between an "antigen binding polypeptide", such as an antibody (Ab), and its corresponding antigen (Ag). Generally, "epitope" refers to the area or region on an Ag to which an Ab specifically binds, i.e. the area or region in physical contact with the Ab. Physical contact may be defined through various criteria (e.g. a distance cut-off of 2-6 Å, such as 3 Å, such as 4 Å, such as 5 Å; or solvent accessibility) for atoms in the Ab and Ag molecules. A protein epitope may comprise amino acid residues in the Ag that are directly involved in binding to a Ab (also called the immunodominant component of the epitope) and other amino acid residues, which are not directly involved in binding, such as amino acid residues of the Ag which are effectively blocked by the Ab, i.e. amino acid residues within the "solvent-excluded surface" and/or the "footprint" of the Ab.

The term epitope herein comprises both types of binding region in any particular region of TREM-1 that specifically binds to a TREM-1 antibody. TREM-1 may comprise a number of different epitopes, which may include, without limitation, conformational epitopes which consist of one or more non-contiguous amino acids located near each other in the mature TREM-1 conformation and post-translational epitopes which consist, either in whole or part, of molecular structures covalently attached to TREM-1, such as carbohydrate groups.

The epitope for a given antibody (Ab)/antigen (Ag) pair can be described and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

At its most detailed level, the epitope for the interaction between the Ag and the Ab can be described by the spatial coordinates defining the atomic contacts present in the Ag-Ab interaction, as well as information about their relative contributions to the binding thermodynamics. At a less detailed level, the epitope can be characterized by the spatial coordinates defining the atomic contacts between the Ag and Ab. At an even less detailed level the epitope can be characterized by the amino acid residues that it comprises as defined by a specific criteria such as the distance between or solvent accessibility of atoms in the Ab:Ag complex. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as TREM-1 residues characterized by having a heavy atom (i.e. a non-hydrogen atom) within a distance of, eg., 4 Å from a heavy atom in the Ab.

From the fact that descriptions and definitions of epitopes, dependant on the epitope mapping method used, are obtained at different levels of detail, it follows that comparison of epitopes for different Abs on the same Ag can similarly be conducted at different levels of detail.

Epitopes described on the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue are shared by the epitopes.

Epitopes may also be defined indirectly, by means of comparing the binding kinetics of antibodies to wild type human TREM-1 with those of human TREM-1 variants that have alanine mutations in anticipated epitopes. Decreased affinity or abrogated binding of an antibody to variants of human TREM-1 in which an amino acid residue has been replaced with an alanine residue indicates that the mutated amino acid contributes to the interaction between said antibody and wild type human TREM-1. This approach provides a negative identification of the epitope. The method is compromised in effectively defining the epitope by the fact that protein misfolding or unfolding would give similar results as abrogation of interaction. The analysis can be complemented by comparative gain of function mutational analyses of an orthologous target protein (eg., cynomolgus monkey TREM-1), if a cross-reactive antibody exists. The comparison will define the epitope differences between the antibody that does not cross-react with, eg., cynomolgus monkey TREM-1 and the cross-reactive antibody.

Indirect identification of the epitope can also be provided by means of measuring antibody (or antibody fragment) binding to variants of the wild type antigen (TREM-1). If an antibody or fragment thereof binds, eg., human but not cynomolgus monkey TREM-1 and if said antibody or fragment thereof is capable of binding a partly humanised variant of cynomolgus monkey TREM-1 then this regained binding indicates that the substituted amino acid residue(s) is/are important for the interaction of the antibody with the antigen. In the same way, increased affinity for humanized variants of cynomolgus monkey TREM-1, of an anti-human TREM-1 antibody (or its Fab fragment) that has a weaker binding to cynomolgus monkey TREM-1 compared to human TREM-1, can provide information on the identity of residues composing the binding epitope.

The effect of the same mutations on any given cross-reactive antibody makes it possible to discriminate between possible protein misfolding (abrogated binding to both antibodies) and loss of interaction in human TREM-1 (binding to one of the antibodies and abrogated binding to the other antibody), whilst unambiguously providing information on the epitope differences between the antibody that does not cross-react and the cross reactive antibody on an amino acid level.

Antibodies of the current invention may be capable of binding variants of human TREM-1. Antibodies of the invention may be capable of binding K20A-hTREM-1-Cmyc2-His6 (SEQ ID NO: 13), as determined using, eg., surface plasmon resonance.

Antibodies of the current invention may be capable of binding variants of cynomolgus monkey TREM-1. Antibodies of the invention may be capable of binding A24T/Y28F/N30S/R32Q/P70H-cTREM-1-Cmyc2-His6 (SEQ ID NO: 14), as determined using, eg., surface plasmon resonance. Antibodies of the invention may be capable of binding A24T/Y28F/N30S/R32Q/E54K-cTREM-1-Cmyc2-His6 (SEQ ID NO: 15), as determined using, eg., surface plasmon resonance.

An antibody of the invention may be capable of specifically binding TREM-1, wherein said antibody is capable of specifically binding (i) at least one amino acid residue selected from the group consisting of the A21, T22, K23, L24, T25, E26, and (ii) at least one amino acid residue selected from the group consisting of the A49, S50, S51, Q52, K53, A54, W55, Q56, I57, I58, R59, D60, G61, E62, M63, P64, K65, T66, L67, A68, C69, T70, E71, R72, P73, S74, K75, N76, S77, H78, P79, V80, Q81, V82, G83, R84, I85 and (iii) at least one amino acid residue selected from the group consisting of the C113, V114, I115, Y116, Q117, P118 and P119 of human TREM-1.

An antibody of the invention may be capable of specifically binding a polypeptide comprising amino acids D38 to F48 of SEQ ID NO: 1 (human TREM-1), as determined using, eg., HX-MS.

An antibody of the invention may have an epitope comprising one, two, three, four, five, six, seven or all of the amino acid residues D38, V39, K40, C41, D42, Y43, T44 and L45 of SEQ ID NO: 1 (human TREM-1) and one, two or all of the amino acid residues selected from the group consisting of the E46, K47 and F48 of SEQ ID NO: 1 (human TREM-1), as determined using, eg., HX-MS.

An antibody of the invention may have an epitope comprising one, two, three or all of the amino acid residues selected from the group consisting of the D42, E46, D92 and H93 of SEQ ID NO: 1 (human TREM-1), as determined using variants of TREM-1 and surface plasmon resonance.

An antibody of the invention may have an epitope comprising at least the amino acid residues E46 and/or D92 of SEQ ID NO: 1 (human TREM-1), as determined using variants of TREM-1 and surface plasmon resonance.

An antibody of the invention may further comprise one, two or all of the amino acid residues selected from the group consisting of the L31, I86 and V101 of SEQ ID NO: 1 (human TREM-1).

An antibody of the invention may be capable of specifically binding a polypeptide comprising amino acid residues E19 to L26 of cynomolgus monkey TREM-1 (SEQ ID NO: 12), or the corresponding amino acids of SEQ ID NO: 21, as determined using, eg., HX-MS.

An antibody of the invention may be capable of specifically binding human TREM-1, wherein the epitope of said antibody comprises one, two, three, four, five, six, seven, eight, nine or all of the amino acid residues selected from the group consisting of the V39, K40, C41, D42, Y43, L45, E46, K47, F48 and A49 of SEQ ID NO: 1.

An antibody of the invention may be capable of specifically binding human TREM-1, wherein the epitope of said antibody comprises the D42 of SEQ ID NO: 1. An antibody of the invention may be capable of specifically binding human TREM-1, wherein the epitope of said antibody comprises the E46 of SEQ ID NO: 1. The epitope of said antibody may comprise the V39, C41, D42, Y43, L45 of SEQ ID NO: 1. The epitope of said antibody may comprise the E46, K47 and A49 of SEQ ID NO: 1. The epitope of said antibody may further comprise the F48 of SEQ ID NO: 1.

The definition of the term "paratope" is derived from the above definition of "epitope" by reversing the perspective. Thus, the term "paratope" refers to the area or region on the Ab to which an Ag specifically binds, i.e. with which it makes physical contact to the Ag.

In the context of an X-ray derived crystal structure, defined by spatial coordinates of a complex between an Ab, such as a Fab fragment, and its Ag, the term paratope is herein, unless otherwise specified or contradicted by context, specifically defined as Ag residues characterized by having a heavy atom (i.e. a non-hydrogen atom) within a distance of 4 Å from a heavy atom in TREM-1.

The epitope and paratope for a given antibody (Ab)/antigen (Ag) pair may be identified by routine methods. For example, the general location of an epitope may be determined by assessing the ability of an antibody to bind to different fragments or variant TREM-1 polypeptides. The specific amino acids within TREM-1 that make contact with an antibody (epitope) and the specific amino acids in an antibody that make contact with TREM-1 (paratope) may also be determined using routine methods. For example, the antibody and target molecule may be combined and the Ab:Ag complex may be crystallised. The crystal structure of the complex may be determined and used to identify specific sites of interaction between the antibody and its target.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques such as surface plasmon resonance (SPR), ELISA or flow cytometry.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope. Competing antibodies, i.e. antibodies belonging to the same "bin" may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes.

An antibody of the invention may compete with mAb 0170 for binding to human TREM-1. An antibody of the invention may compete with mAb 0170 for binding to cynomolgus monkey TREM-1. In other words, an antibody of the invention may belong to the same "bin" as mAb 0170.

The term "binding affinity" herein refers to a measurement of the strength of a non-covalent interaction between two molecules, e.g. an antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the equilibrium dissociation constant ($K_D$). In turn, $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D = k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

An antibody of the invention may bind human TREM-1 with an affinity (KD) that is $1 \times 10^{-7}$M or less, $1 \times 10^{-8}$M or less, or $1 \times 10^{-9}$M or less, or $1 \times 10^{-10}$M or less, $1 \times 10^{-11}$M or less, $1 \times 10^{-12}$M or less or $1 \times 10^{-13}$M or less, as determined using surface plasmon resonance. An antibody of the invention may bind cynomolgus monkey TREM-1 with an affinity (KD) that is $1 \times 10^{-7}$M or less, $1 \times 10^{-8}$M or less, or $1 \times 10^{-9}$M or less, or $1 \times 10^{-10}$M or less, $1 \times 10^{-11}$M or less, $1 \times 10^{-12}$M or less or $1 \times 10^{-13}$M or less, as determined using surface plasmon resonance.

The term "binding specificity" herein refers to the interaction of a molecule such as an antibody, or fragment thereof, with a single exclusive antigen, or with a limited number of highly homologous antigens (or epitopes). In contrast, antibodies that are capable of specifically binding to TREM-1 are not capable of binding dissimilar molecules. Antibodies according to the invention may not be capable of binding Nkp44.

The specificity of an interaction and the value of an equilibrium binding constant can be determined directly by well-known methods. Standard assays to evaluate the ability of ligands (such as antibodies) to bind their targets are known in the art and include, for example, ELISAs, Western blots, RIAs, and flow cytometry analysis. The binding kinetics and binding affinity of the antibody also can be assessed by standard assays known in the art, such as SPR.

A competitive binding assay can be conducted in which the binding of the antibody to the target is compared to the binding of the target by another ligand of that target, such as another antibody.

In another aspect, the present invention provides compositions and formulations comprising molecules of the invention, such as the TREM-1 antibodies, polynucleotides, vectors and cells described herein. For example, the invention provides a pharmaceutical composition that comprises one or more TREM-1 antibodies of the invention, formulated together with a pharmaceutically acceptable carrier.

Accordingly, one object of the invention is to provide a pharmaceutical formulation comprising such a TREM-1 antibody which is present in a concentration from 0.25 mg/ml to 250 mg/ml, such as a concentration of from 10 to 200 mg/ml, and wherein said formulation has a pH from 2.0 to 10.0, such as a pH of from 4.0 to 8.0. The formulation may further comprise one or more of a buffer system, a preservative, a tonicity agent, a chelating agent, a stabilizer and/or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, 19$^{th}$ edition, 1995.

In one embodiment, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

The TREM-1 antibodies of the present invention and pharmaceutical compositions comprising such antibodies may be used for the treatment of inflammatory diseases such as the following: inflammatory bowel disease (IBD), Crohns disease (CD), ulcerative colitis (UC), irritable bowel syndrome, rheumatoid arthritis (RA), psoriasis, psoriatic arthritis, systemic lupus erythematosus (SLE), lupus nephritis, type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atoptic dermatitis, vitiligo, graft versus host disease, Sjogrens's syndrome, autoimmune nephritis, Goodpasture's syndrome, chronic inflammatory demyelinating polyneuropathy, allergy, asthma and other autoimmune diseases that are a result of either acute or chronic inflammation.

TREM-1 antibodies of the invention may be suitable for use in the treatment of individuals with inflammatory bowel disease. Inflammatory Bowel Disease (IBD) is a disease that may affect any part of the gastrointestinal tract from mouth to anus, causing a wide variety of symptoms. IBD primarily causes abdominal pain, diarrhea (which may be bloody), vomiting or weight loss, but may also cause complications outside of the gastrointestinal tract such as skin rashes, arthritis, inflammation of the eye, fatigue and lack of concentration. Patients with IBD can be divided into two major classes, those with ulcerative colitis (UC) and those with Crohn's disease (CD). CD generally involves the ileum and colon, it can affect any region of the intestine but is often discontinuous (focused areas of disease spread throughout the intestine). UC always involves the rectum (colonic) and is more continuous. In CD, the inflammation is transmural, resulting in abscesses, fistulas and strictures, whereas in UC, the inflammation is typically confined to the mucosa. There is no known pharmaceutical or surgical cure for Crohn's disease, whereas some patients with UC can be cured by surgical removal of the colon. Treatment options are restricted to controlling symptoms, maintaining remission and preventing relapse. Efficacy in inflammatory bowel disease in the clinic may be measured as a reduction in the Crohn's Disease Activity Index (CDAI) score for CD which is scoring scale based on laboratory tests and a quality of life questionnaire. In animal models, efficacy is mostly measured by increase in weight and also a disease activity index (DAI), which is a combination of stool consistency, weight and blood in stool.

TREM-1 antibodies of the invention may be suitable for use in the treatment of individuals with rheumatoid arthritis. Rheumatoid arthritis (RA) is a systemic disease that affects nearly if not all of the body and is one of the most common forms of arthritis. It is characterized by inflammation of the joint, which causes pain, stiffness, warmth, redness and swelling. This inflammation is a consequence of inflammatory cells invading the joints, and these inflammatory cells release enzymes that may digest bone and cartilage. As a result, this inflammation can lead to severe bone and cartilage damage and to joint deterioration and severe pain, among other physiologic effects. The involved joint can lose its shape and alignment, resulting in pain and loss of movement.

There are several animal models for rheumatoid arthritis known in the art. For example, in the collagen-induced arthritis (CIA) model, mice develop an inflammatory arthritis that resembles human rheumatoid arthritis. Since CIA shares similar immunological and pathological features with RA, this makes it a suitable model for screening potential human anti-inflammatory compounds. Efficacy in this model is measured by decrease in joint swelling. Efficacy in RA in the clinic is measured by the ability to reduce symptoms in patients which is measured as a combination of joint swelling, erythrocyte sedimentation rate, C-reactive protein levels and levels of serum factors, such as anti-citrullinated protein antibodies.

TREM-1 antibodies of the invention may be suitable for use in the treatment of individuals with psoriasis. Psoriasis is a T-cell mediated inflammatory disorder of the skin that can cause considerable discomfort. It is a disease for which there is currently no cure and it affects people of all ages. Although individuals with mild psoriasis can often control their disease with topical agents, more than one million patients worldwide require ultraviolet light treatments or systemic immunosuppressive therapy. Unfortunately, the inconvenience and risks of ultraviolet radiation and the toxicities of many therapies limit their long-term use. Moreover, patients usually have recurrence of psoriasis, and in some cases rebound shortly after stopping immunosuppressive therapy. A recently developed model of psoriasis based on the transfer of CD4+ T cells mimics many aspects of human psoriasis and therefore can be used to identify compounds suitable for use in treatment of psoriasis (Davenport et al., Internat. Immunopharmacol 2:653-672, 2002). Efficacy in this model is a measured by reduction in skin pathology using a scoring system. Similarly, efficacy in patients is measured by a decrease in skin pathology.

TREM-1 antibodies of the invention may be suitable for use in the treatment of individuals with psoriatic arthritis. Psoriatic arthritis (PA) is a type of inflammatory arthritis that occurs in a subset of patients with psoriasis. In these patients, the skin pathology/symptoms are accompanied by a joint swelling similar to that seen in rheumatoid arthritis. It features patchy, raised, red areas of skin inflammation with scaling. Psoriasis often affects the tips of the elbows and knees, the scalp, the navel and around the genital areas or anus. Approximately 10% of patients who have psoriasis also develop an associated inflammation of their joints.

The term "treatment", as used herein, refers to the medical therapy of any human or other animal subject in need thereof. Said subject is expected to have undergone physical examination by a medical or veterinary medical practitioner, who has given a tentative or definitive diagnosis which would indicate that the use of said treatment is beneficial to the health of said human or other animal subject. The timing and purpose of said treatment may vary from one individual to another, according to many factors, such as the status quo of the subject's health. Thus, said treatment may be prophylactic, palliative, symptomatic and/or curative.

In terms of the present invention, prophylactic, palliative, symptomatic and/or curative treatments may represent separate aspects of the invention.

An antibody of the invention may be administered parenterally, such as intravenously, such as intramuscularly, such as subcutaneously. Alternatively, an antibody of the invention may be administered via a non-parenteral route, such as perorally or topically. An antibody of the invention may be administered prophylactically. An antibody of the invention may be administered therapeutically (on demand).

EXEMPLARY EMBODIMENTS

1. A method of identifying a functional TREM-1 antibody, comprising (a) culturing a first cell expressing TREM-1, a signalling protein and a reporter construct; (b) measuring the activity of the first cell when said cell is incubated with a TREM-1 modifying agent; (c) contacting the culture of (b) with a TREM-1 antibody; and (d) measuring that the activity of the first cell is less than or more than the activity measured in (b).
2. A method of identifying a blocking TREM-1 antibody, comprising (a) culturing a first cell expressing TREM-1, a signalling protein and a reporter construct; (b) measuring the activity of the first cell when said cell is incubated with an activated neutrophil; (c) contacting the culture of the first cell and the activated neutrophil with a TREM-1 antibody; and (d) measuring that the activity of the first cell is less than the activity measured in (b).
3. The method of any one of embodiments 1-2, wherein the modifying agent of (b) is an activated neutrophil or a TREM-1 ligand.
4. A method of identifying a stimulating TREM-1 antibody, comprising (a) culturing a first cell expressing TREM-1, a signalling protein and a reporter construct; (b) measuring the activity of the first cell; (c) contacting/incubating said cell with a TREM-1 antibody; and (d) measuring that the activity of the first cell is more than the activity measured in (b).
5. The method of any one of embodiments 1-4, wherein the first cell is of haematopoetic origin.
6. The method according to embodiment 5, wherein the cell of haematopoetic origin is a myeloid cell.
7. The method according to embodiment 5, wherein the cell of haematopoetic origin is a T-cell.
8. The method according to any one of embodiments 1-7, wherein the signalling protein is DAP10.
9. The method according to any one of embodiments 1-7, wherein the signalling protein is DAP12.
10. The method according to any one of embodiments 1-7, wherein the signalling protein is TCR zeta.
11. The method according to any one of embodiments 1-7, wherein the signalling protein is Fc gamma RIII.
12. The method according to any one of embodiments 1-7, wherein the signalling protein is a Fc receptor.
13. The method according to any one of embodiments 1-6, wherein the reporter construct comprises a transcription factor and a reporter gene.
14. The method according to embodiment 13, wherein said transcription factor is NFAT.
15. The method according to embodiment 14, wherein said transcription factor is NFkB.
16. The method according to any one of embodiments 13-15, wherein said reporter gene encodes β-galactosidase.
17. The method according to any one of embodiments 13-15, wherein said reporter gene encodes luciferase.
18. The method according to any one of embodiments 13-15, wherein said reporter gene encodes green fluorescent protein (GFP).
19. The method according to any one of embodiments 13-15, wherein said reporter gene is a gene that encodes chloramphenicol transferase.
20. A method of identifying a blocking TREM-1 antibody, comprising (a) culturing a T-cell expressing TREM-1, DAP12 and a gene that encodes luciferase; (b) measuring the luminescence of the T-cell when it is incubated with an activated neutrophil; (c) contacting the co-culture of (b) with a TREM-1 antibody; and (d) measuring that the luminescence of the T-cell is less than the activity measured in (b).
21. The method according to embodiment 7, wherein said cell is a BWZ.36/hTREM-1:DAP12:NFAT-LacZ T-cell line.
22. The antibody identified by the method of any one of embodiments 1-3 and 5-21.
23. An antibody that is capable of specifically binding to TREM-1 and that is capable of blocking TREM-1 function.
24. The antibody according to any one of embodiments 22-23, wherein said antibody is capable of preventing or reducing the dimerisation/multimerisation of TREM-1.
25. The antibody according to any one of embodiments 22-24, wherein said antibody is capable of blocking the interaction between TREM-1 and its ligand.
26. The antibody according to any one of embodiments 22-25, wherein said antibody is capable of blocking PGLYRP1-induced TREM-1 function.
27. The antibody according to any one of embodiments 22-26, wherein the TREM-1 is human TREM-1.
28. The antibody according to embodiment 27, wherein said antibody is also capable of specifically binding to and blocking the function of TREM-1 from another species than a human.
29. The antibody according to embodiment 28, wherein the TREM-1 from another species is cynomolgus monkey TREM-1.
30. The antibody according to embodiment 28, wherein the TREM-1 from another species is rhesus monkey TREM-1.
31. The antibody according to any one of embodiments 22-30, which is capable of specifically binding K20A-hTREM-1-Cmyc2-His6 (SEQ ID NO: 13).
32. The antibody according to any one of embodiments 22-31, which is capable of specifically binding A24T/Y28F/N30S/R32Q/P70H-cTREM-1-Cmyc2-His6 (SEQ ID NO: 14).
33. The antibody according to any one of embodiments 22-32, which is capable of specifically binding A24T/Y28F/N30S/R32Q/E54K-cTREM-1-Cmyc2-His6 (SEQ ID NO: 15).
34. The antibody according to any one of embodiments 22-33, which competes with mAb 0170 for binding to human TREM-1.
35. The antibody according to any one of embodiments 22-34, which competes with mAb 0170 for binding to cynomolgus monkey TREM-1.
36. The antibody according to any one of embodiments 22-35, which is capable of specifically binding a polypeptide comprising amino acids D38 to F48 of SEQ ID NO: 1 (human TREM-1), as determined using, eg., HX-MS.
37. The antibody according to any one of embodiments 22-36, which has an epitope comprising one, two, three, four, five, six, seven or all of the amino acid residues selected from the group consisting of the D38, V39, K40, C41, D42, Y43, T44 and L45 of SEQ ID NO: 1 (human TREM-1) and one, two or all of the amino acid residues selected from the group consisting of the E46, K47 and F48 of SEQ ID NO: 1 (human TREM-1), as determined using, eg., HX-MS.
38. The antibody according to any one of embodiments 22-37, which is capable of specifically binding a polypeptide comprising amino acid residues E38 to L45 of cynomolgus monkey TREM-1, as determined using, eg., HX-MS.
39. The antibody according to any one of embodiments 22-38 which has an epitope comprising at least the amino acid residues selected from the group consisting of the D42, E46, D92 and H93 of SEQ ID NO: 1 (human TREM-1), as determined using surface plasmon resonance.

40. The antibody according to any one of embodiments 22-39 which has an epitope comprising at least the amino acid residues E46 and/or D92 of SEQ ID NO: 1 (human TREM-1), as determined using surface plasmon resonance.

41. The antibody according to any one of embodiments 22-40, wherein said antibody is capable of specifically binding (i) at least one amino acid residue selected from the group consisting of the A21, T22, K23, L24, T25, E26, and (ii) at least one amino acid residue selected from the group consisting of the A49, S50, S51, Q52, K53, A54, W55, Q56, I57, I58, R59, D60, G61, E62, M63, P64, K65, T66, L67, A68, C69, T70, E71, R72, P73, S74, K75, N76, S77, H78, P79, V80, Q81, V82, G83, R84, I85 and (iii) at least one amino acid residue selected from the group consisting of the C113, V114, I115, Y116, Q117, P118 and P119 of human TREM-1.

42. The antibody according to any one of embodiments 22-40, wherein said antibody is capable of specifically binding (i) at least one amino acid residue selected from the group consisting of the V39, K40, C41, D42, Y43, T44, L45, E46, K47, F48, A49, S50, S51, Q52, K53, A54, W55, Q56, and (ii) at least one amino acid residue selected from the group consisting of the T70, E71, R72, P73, S74, K75, N76, S77, H78, P79, V80, Q81, V82, G83, R84, I85 and (iii) at least one amino acid residue selected from the group consisting of the and C113, V114, I115, Y116, Q117, P118, P119.

43. The antibody according to any one of embodiments 22-42, the heavy chain of which comprises a CDRH3 sequence corresponding to amino acid residues 101 to 110 (DMGIRRQFAY) of SEQ ID NO: 4, wherein one, two or three of said amino acid residues may be substituted by a different amino acid.

44. The antibody according to any one of embodiments 22-42, the heavy chain of which comprises a CDRH3 sequence corresponding to amino acid residues 101 to 110 (DMGQRRQFAY) of SEQ ID NO: 6, wherein one, two or three amino acid residues may be substituted by a different amino acid.

45. The antibody according to any one of embodiments 43-44, further comprising a CDRH1 sequence corresponding to amino acid residues 31 to 35 (TYAMH) of SEQ ID NO: 4 or SEQ ID NO: 6, wherein one of these amino acid residues may be substituted by a different amino acid residue; and/or a CDRH2 sequence corresponding to amino acids 50 to 68 (RIRTKSSNYATYYAASVKG) of SEQ ID NO: 4 or SEQ ID NO: 6, wherein one, two or three of said amino acids may be substituted by a different amino acid residue.

46. The antibody according to any one of embodiments 43-45, the light chain of which comprises: a CDRL1 sequence corresponding to amino acid residues 24 to 38 (RASESVDTFDYSFLH) of SEQ ID NO: 5 or SEQ ID NO: 7, wherein one, two or three of these amino acid residues may be substituted with a different amino acid; and/or a CDRL2 sequence corresponding to amino acid residues 54 to 60 (RASNLES) of SEQ ID NO: 5 or SEQ ID NO: 7, wherein one or two of these amino acid residues may be substituted with a different amino acid; and/or a CDRL3 sequence corresponding to amino acid residues 93 to 101 (QQSNEDPYT) of SEQ ID NO: 5 or SEQ ID NO: 7, wherein one or two of these amino acid residues may be substituted with a different amino acid.

47. The antibody according to any one of embodiments 43-46, comprising SEQ ID NO: 4 or SEQ ID NO: 6 and/or SEQ ID NO: 5 or SEQ ID NO: 7.

48. The antibody according to any one of embodiments 22-47, which binds human TREM-1 with a binding affinity (KD) that is $1 \times 10^{-7}$M or less, $1 \times 10^{-8}$M or less, or $1 \times 10^{-9}$M or less, or $1 \times 10^{-10}$M or less, $1 \times 10^{-11}$M or less, $1 \times 10^{-12}$M or less or $1 \times 10^{-13}$M or less, as determined using surface plasmon resonance.

49. The antibody according to embodiment 48, wherein said binding affinity (KD) is $1 \times 10^{-10}$M or less.

50. The antibody according to any one of embodiments 22-49, which binds cynomolgus monkey TREM-1 with a binding affinity (KD) that is $1 \times 10^{-7}$M or less, $1 \times 10^{-8}$M or less, or $1 \times 10^{-9}$M or less, or $1 \times 10^{-10}$M or less, $1 \times 10^{-11}$M or less, $1 \times 10^{-12}$M or less or $1 \times 10^{-13}$M or less, as determined using surface plasmon resonance.

51. The antibody according to embodiments 50, wherein said binding affinity is $1 \times 10^{-9}$M or less.

52. The antibody according to any one of embodiments 22-51, which is an IgG.

53. The antibody according to any one of embodiments 22-52 for use as a medicament.

54. The antibody according to any one of embodiments 22-53 for the treatment of an autoimmune disease and/or chronic inflammation.

55. The antibody according to any one of embodiments 22-52 for the manufacture of a medicament for the treatment of an autoimmune disease and/or a chronic inflammation.

56. A method of treating an autoimmune disease and/or chronic inflammation comprising administering an antibody according to any one of embodiments 22-52 to a subject in need thereof.

57. The use according to any one of embodiments 53-55 or the method according to embodiment 56, wherein said autoimmune disease is rheumatoid arthritis.

58. The use according to any one of embodiments 53-55 or the method according to embodiment 56, wherein said autoimmune disease is Crohn's disease.

59. The use according to any one of embodiments 53-55 or the method according to embodiment 56, wherein said autoimmune disease is ulcerative colitis.

60. The use according to any one of embodiments 53-55 or the method according to embodiment 56, wherein said autoimmune disease is psoriatic arthritis.

The present invention is further illustrated by the following examples which should not be construed as further limiting. The contents of all figures and all references, patents and published patent applications cited throughout this application are expressly incorporated herein by reference.

EXAMPLES

Example 1

Generation of a BWZ.36 humanTREM-1:DAP12 Stable Cell Line

The BWZ.36/hTREM-1:DAP12:NFAT-LacZ cell line (herein also referred to as the "BWZ/hTREM-1 reporter cell") was derived from BW5147 T cells (*Mus musculus* thymus lymphoma cell line, ATCC TIB-47, LGC Standards, Middelsex, UK) and contains a LacZ reporter construct regulated by four copies of the NFAT promoter element (see Karttunen, J. & Shastri, N. (1991) Proc. Natl. Acad. Sci. USA 88, 3972-3976 and Fiering, S., Northrop, J. P., Nolan, G. P., Matilla, P., Crabtree, G. R. & Herzenberg, L. A. (1990) Genes Dev. 4, 1823-1834). TREM/DAP12/pMX-IRES vector (encoding 786 by of TREM-1 from a SmaI site to BamHI site using TREM-1 cDNA (Gene Bank Ref. ID: NM_018643.2, Sino Biological Inc., Beijing, China) as template and oligo 5' TAGTAGGGATCCGCTGGTGCACAGGAAGG (SEQ ID NO: 16) and 5' TAGTAGGCGGCCGCTTCGTGGGC- CTAGGGTAC (SEQ ID NO: 17) as primers cloned into pIREShyg vector GenBank Accession #U89672 (Cat. no. 6061-1, Clontech Laboratories, CA, USA) was transfected in PLAT-E packaging cell line (provided by W. Yokoyama, Washington University; alternatively, Cat. no. RV-101, Cell Biolabs Inc, Bio-Mediator KY, Vantaa, Finland) using Superfect transfection reagent (Cat. no. 301305, Qiagen Nordic, Denmark). PLAT-E supernatants containing TREM/DAP12/pMX-IRES viral particles were used to infect BWZ.36 cells as follows: $2\times10^5$ BWZ.36 cells were cultured in 6 well plates and the medium was replaced with 1.5 ml of supernatant containing the viral particles+8 mg/ml of polybrene. After 6-8 hours, 1.5 ml of normal medium was added to the plate and the cells were incubated for an additional 24 hours. BWZ.36 cell lines stably expressing TREM-1 were stained with anti TREM-1 monoclonal antibody (clone 21C7) and isolated by cell sorting.

Example 2

Cultivation of a BWZ.36 humanTREM-1:DAP12 Stable Cell Line

BWZ/hTREM-1 reporter cell were cultured in RPMI 1640 w/o phenol red (Cat#11835, Gibco, Carlsbad Calif., USA), supplemented with 10% FCS (Cat#16140-071, Gibco, N.Y., USA), 1% Pen/Strep (Cat#15070-06, Gibco), 1 mM Sodium Pyruvate (Cat #11360, Gibco), 5 µM-2ME (Cat#31350-010, Gibco) and 2 mM L-Glutamine (Cat #25030, Gibco). No special plates or coating was required. 10 ml Versene (Cat #15040, Gibco) was added to detach the cells which then were transferred to tubes, centrifuged 1200 rpm 5 min and washed in fresh RPMI 1640 w/o phenol red. These cell were then ready to use in an assay or re-culture for further propagation.

Example 3

Immunisation of Mice and Identification of mAbs

In order to generate antibodies that bind human TREM-1, both wild type Balb/C mice and TREM-1 knock-out (KO) mice (C57BL/6 background) were immunised with either human (h) TREM-1 (SEQ ID NO:1), cells expressing hTREM-1 (BWZ.36 cells), or a combination of both. Primary screening was done either by means of direct ELISA on hTREM-1 protein or by means of FMAT, using BWZ.36 cells expressing hTREM-1. Secondary screening was done by flow cytometry on HEK293 cells expressing hTREM-1. Positive hybridoma supernatants were then screened in the BWZ/hTREM-1 reporter assay described in Example 4.

The highest number of blocking antibodies was obtained from KO mice immunised with hTREM-1 protein six times at two weeks intervals, followed by a booster injection. In total, over 200 hTREM-1 antibodies were isolated, of which approximately 70 were subsequently found to have a blocking effect.

Figure 4:
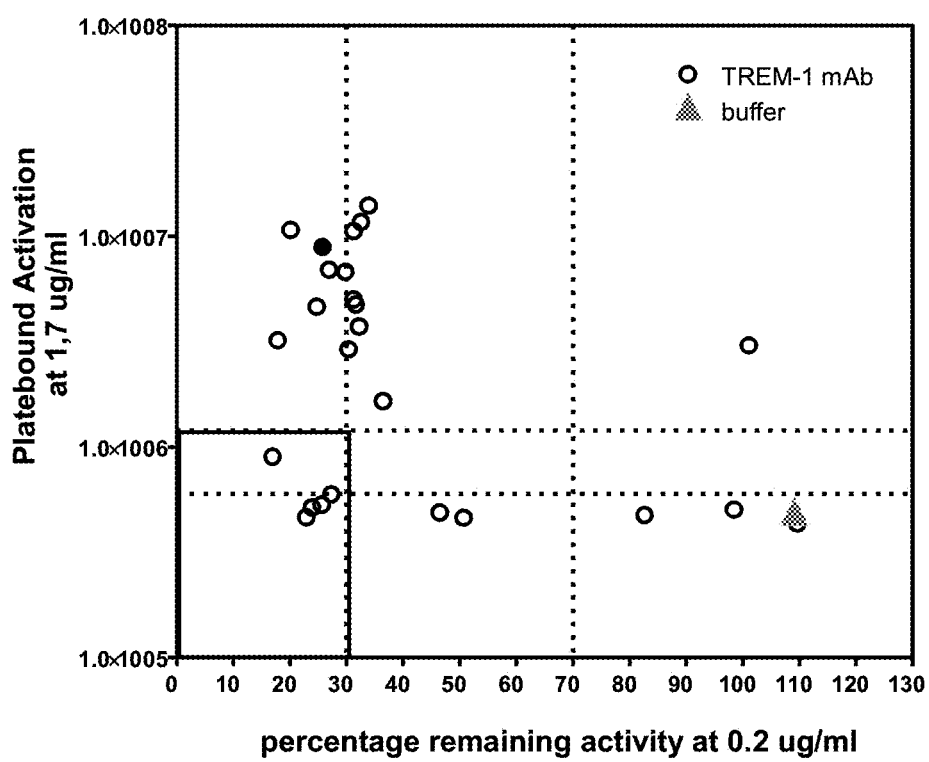
FIG. 4: Activity in the BWZ/hTREM-1 reporter assay. On the x-axis, TREM-1 blocking activity is shown as the activity that remained when 0.2 µg/ml antibody was added to the BWZ/hTREM-1 reporter cell, which had been pre-activated with PGN-stimulated neutrophils. When TREM-1 antibodies were platebound, some (including all of the commercially available TREM-1 antibodies) were able to crossbind TREM-1 and thereby activate TREM-1. This activity is shown on the y-axis. Thus, the antibodies shown as dots in the box in the lower left-hand corner all show different properties compared to known antibodies, being advantageously blocking and not agonistic.
Figure 5:
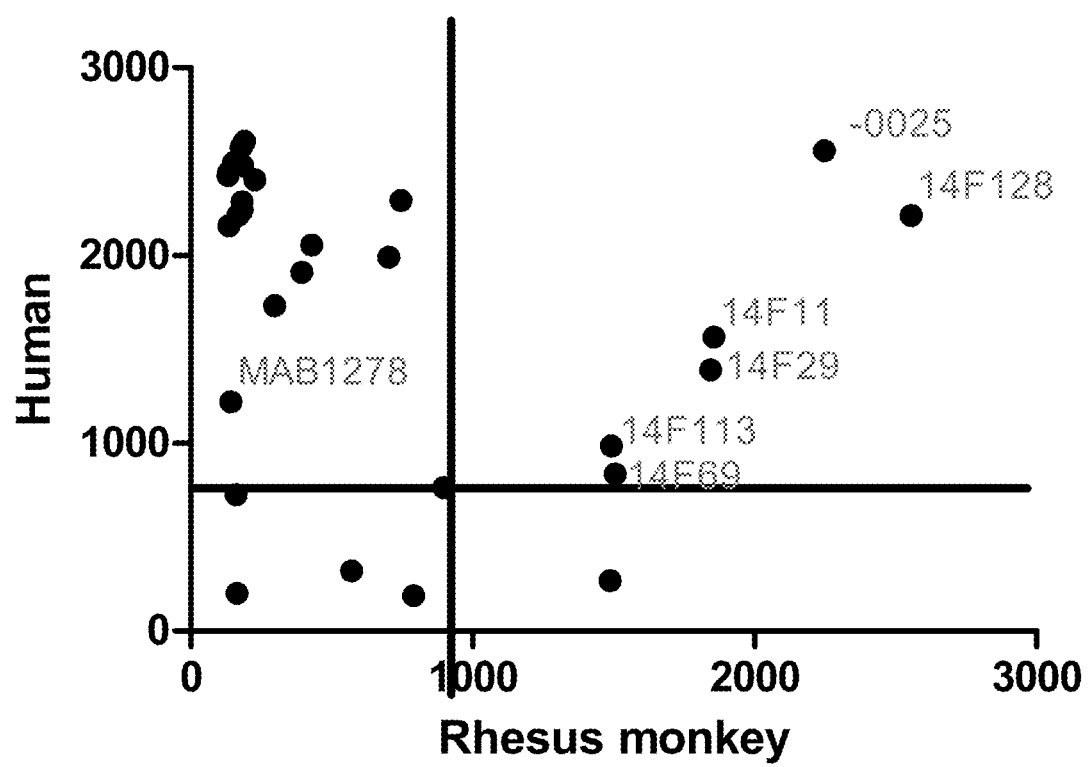
FIG. 5: Binding of human TREM-1 antibodies to PBMCs from a rhesus monkey. In the upper left corner, it is shown that most of the antibodies only bound human TREM-1 (each black dot represents one antibody). Some antibodies, such as mAbs 0025 and 14F128, 14F11, 14F29, 14F113 and 14F69, were able to bind to both human TREM-1 and rhesus monkey TREM-1, showing cross-reactivity.
Figure 6A:
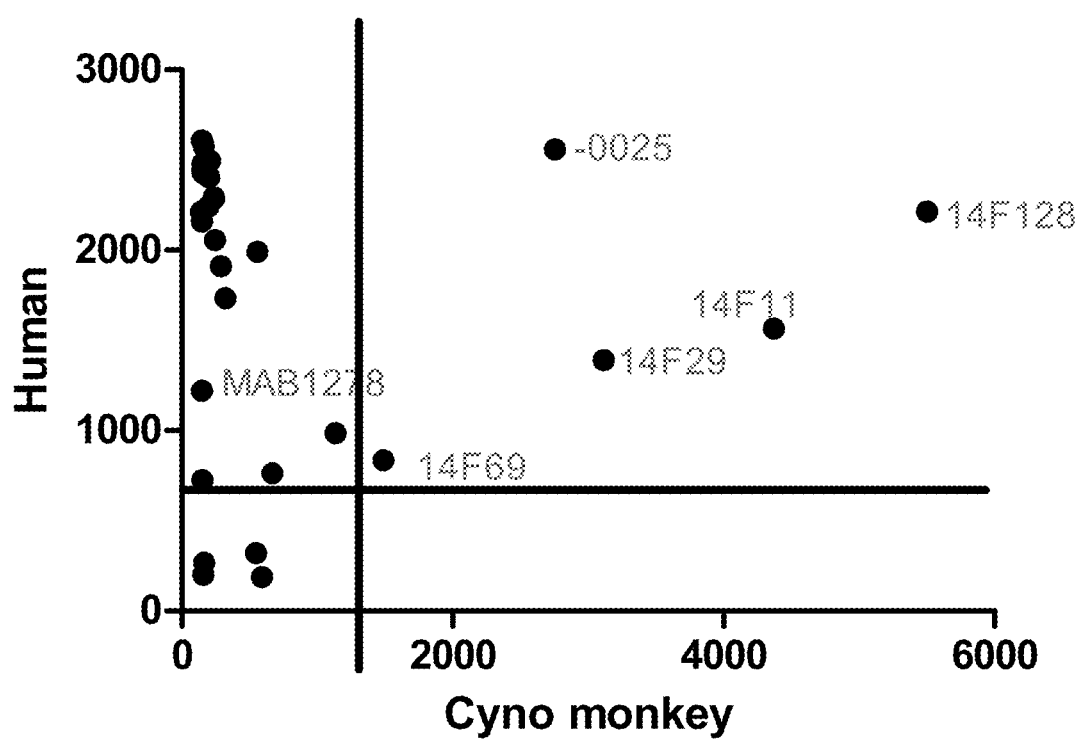
FIG. 6A: In the upper left corner, it is shown that most antibodies only bound human TREM-1 (each black dot represents one antibody). Some antibodies, such as mAb 0025 and 14F128, 14F11, 14F29, were able to bind both human and cynomolgus monkey TREM-1, showing cross-reactivity. Some antibodies, such as 14F69 (mAb 0044), are able to bind cynomolgus monkey PBMCs (FIG. 6B) and human PBMCs (FIG. 6C) equally well.
Figure 6B:
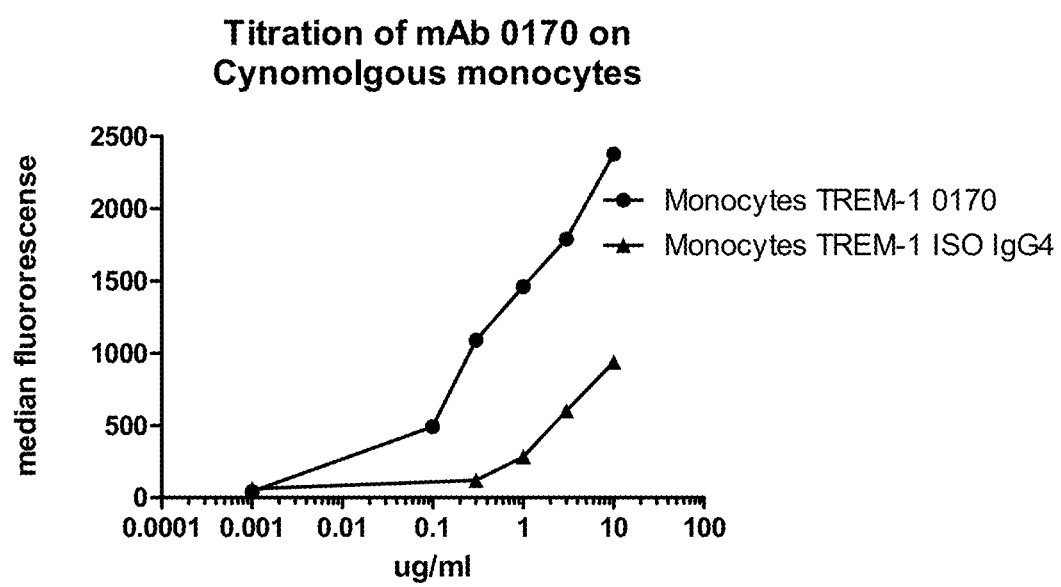
FIG. 6: Binding of anti-human TREM-1 antibodies to PBMCs from a cynomolgus monkey.
Figure 6C:
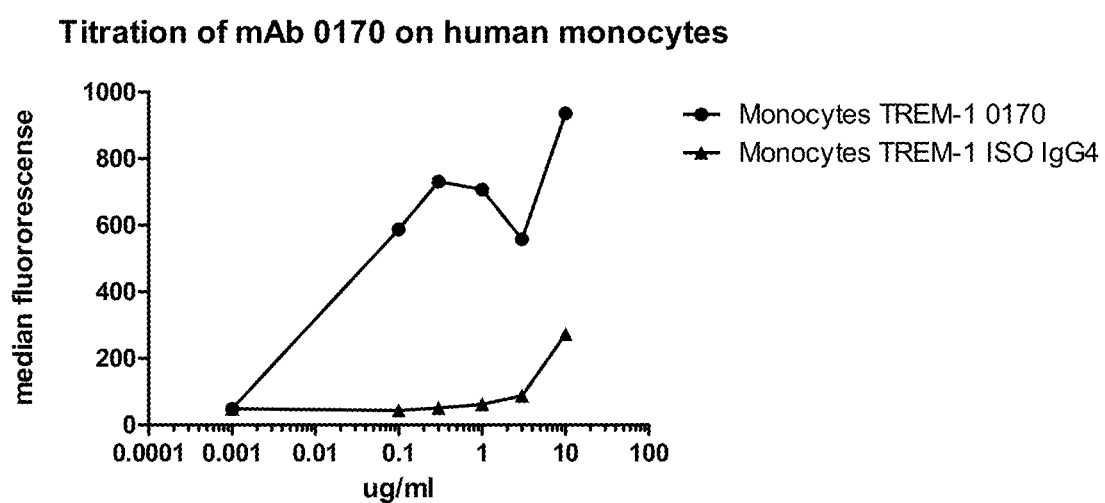

All TREM-1 specific hybridoma supernatants were tested in the BWZ/hTREM-1 reporter assay first as supernatants and later as purified antibodies, in full titration from 5000 ng/ml down to 7 ng/ml, both as soluble and as platebound antibodies. Blood from a range of different donors was used as a source of fresh neutrophils. As an example, FIG. 4 shows antibodies from one fusion where the activity in the reporter assay as blocking activity is on the x-axis and the agonistic activity when the antibody is plate-bound is on the y-axis.

Example 4

Identification of PGLYRP1 as a Neutrophil-Expressed TREM-1 Ligand

Figure 3:
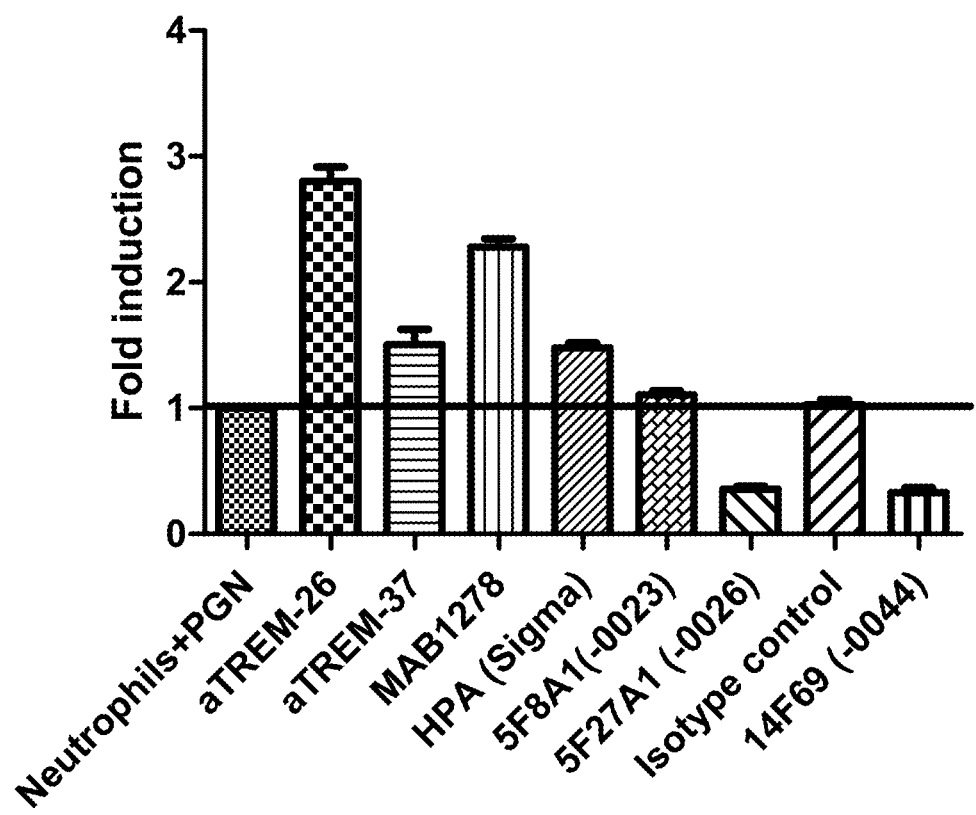
FIG. 3: A normalised reporter assay, in which TREM-1 is stimulated by PGN-activated neutrophils, shows that the commercially available antibodies TREM-26 (cat. no. 314902, Biolegend, San Diego, Calif. 92121, USA), TREM-37 (cat. no. 316102, Biolegend, San Diego, Calif. 92121, USA), MAB1278 (cat. no. MAB1278, R&D Systems, Minneapolis, Minn. 55413, USA), and anti-TREM-1 HPA (cat. no. HPA005563, Sigma, St Louis, Mo., USA) are agonistic antibodies that enhance the TREM-1 dependent luminescence signal in the reporter assay (giving a signal higher than 1). The antibody identified as 5F27A1 and 14F69 are shown to be the best blocker (giving a signal less than 0.5). Data plotted as mean±SEM (n=3). Isotype control MAB002 (cat. no. MAB002, R&D Systems, Minneapolis, Minn. 55413, USA). All antibodies have been used at 1 µg/ml.

PGLYRP1 was identified as a TREM-1 ligand through the use of immunoprecipitation coupled with mass spectroscopy (IP-MS). Soluble TREM-1 tetramer was used as an affinity "bait" molecule to identify a ligand. Briefly, TREM-1-tetramer-Fc (SEQ ID NO: 2) and separately CD83-Fc (SEQ ID NO: 5) were each incubated at final concentrations of 100 µg/ml with 270 million human neutrophils, purified by dextran sedimentation as described above, in 1 mL PBS at 4° C., 90 minutes with mild shaking. After pelleting these cells, the cells were resuspended in 1 mL PBS buffer with the inclusion of the crosslinker 3,3'-Dithiobis[sulfosuccinimidylpropionate] (DTSSP) (Thermo Scientific: 21578, Rockford, Ill., USA), at a concentration of 2 mM and incubated 30 minutes at room temperature. Cells were washed 3× with 1 mL PBS followed by lysis in 1 mL RIPA buffer (Thermo Scientific, 89901, Rockford, Ill., USA). The lysate was centrifuged at 15,000×g for 10 minutes at 4° C. to remove insoluble materials. Neutrophil proteins cross-linked to Fc coupled probes were immunoprecipitated from the supernatant using Protein A Mag Sepharose™ beads (GE Healthcare Life Sciences, 28-9670-56, Piscataway, N.J., USA). Briefly, 50 µL of beads were first washed with 200 µL PBS, then resuspended in 1 mL of cell lysate, incubated 60 minutes at 4° C., magnetically captured, and sequentially washed 2× with 200 µl RIPA buffer then 3× with 200 µL PBS. Upon removing PBS from the final magnetic capture, proteins were eluted from the magnetic beads using 200 µL buffer containing 8 M Urea, 100 mM Tris (pH 8.0), and 15 mM TCEP (Thermo Scientific, 77720, Rockford, Ill., USA) and incubated at room temperature for 30 minutes, beads were captured and supernatant was transferred to a Microcon Ultracel YM-30 filter (Millipore, 42410, Billerica, Mass., USA). Samples were spun at 14,000×g, 20° C., 30-60 minutes until no liquid remained on the top of the filter membrane. The retained proteins were then alkylated with 100 µL 50 mM IAA (iodoacetamide) in 8 M Urea for 30 minutes in dark at room temperature. The filter was washed 2× with 100 µL 50 mM $NH_4HCO_3$ and then transferred to a new collection tube. 1 µg trypsin (Promega, V5111, Madison, Wis.) in 60 µL 50 mM $NH_4HCO_3$ was added followed by incubation at 37° C. overnight. The tryptic digest was collected by centrifugation at 14,000×g for 30 minutes followed by washing the filter with 50 µL 50 mM $NH_4HCO_3$. 10 µL of the digest was analyzed by LC/MS/MS using an LTQ-Orbitrap-XL mass spectrometer (Thermo Scientific, Waltham, Mass., USA). The data was searched against IPI human database (v3.81) using SEQUEST-Sorcerer engine (4.0.4 build) (SageN, Milpitas, Calif., USA) and then post processed with Scaffold 3 (Proteome Software, Portland, Oreg., USA) to filter protein IDs with a false discovery rate of 1%. After negative control subtraction, PGLYRP1 was found to be a high-confidence protein specifically associated with hTREM-1 tetramer. The immunoprecipitation in the neutrophils showed that out of the 148 identified proteins, 72 proteins were immunoprecipitated by the control construct (CD83) alone, 73 of the proteins were identical for TREM-1 and CD83, whereas only three were TREM-1 specific (FIG. 3). The experiment was subsequently repeated using neutrophils from a different donor and PGLYRP1 was again identified as specifically interacting with hTREM-1.

Example 5

Refolding and Purification of Human PGLYRP1 Expressed from *E. Coli*

Human PGLYRP1 was expressed as inclusion bodies in *Escherichia coli* BL21 (DE3) cells. Bacteria were harvested by centrifugation, resuspended in 50 mM Tris-HCl pH8.0, 500 mM NaCl, 5 mM EDTA, 0.5% Triton X-100 and disrupted by sonication. The insoluble pellet was washed three times with 50 mM Tris, pH 8.0, 1% TritonX-100, 2 M urea and once with 50 mM Tris pH 8.0, then solubilized in 50 mM Tris-HCl, 6M guanidine hydrochloride, pH7.4, 1 mM DTT (final protein concentration 20 mg/ml). For in vitro folding, solubilized human PGLYRP1 inclusion bodies were diluted into 50 mM Tris, pH 8.0, 2 mM EDTA, 5 mM cysteamine, 0.5 mM cystamine, 0.4 M arginine (final protein concentration 1 mg/ml). After overnight at 4° C., the folding mixture was cleared by centrifugation/filtration and then diluted 12 fold into 10 mM MES pH 3.5 to lower the conductivity and pH (final pH ~5.8, conductivity ~6 mS/cm). The diluted folding mixture was then applied to a Hitrap SP HP 5 ml column (17-1151-01 GE Healthcare, Uppsala, Sweden), followed by a 5 column volume wash with 50 mM MES pH 5.8. The bound human PGLYRP1 was then eluted with a 0-60% linear gradient of 50 mM MES pH 5.8, 1 M NaCl in 20 column volume. The fractions containing refolded human PGLYRP1 were pooled and concentrated to less than 4 ml by Amicon ultra 15 centrifugal units ((UFC800324 3,000 kDa MWCO, Millipore, Hellerup, Denmark). A Hiload 26/60 Superdex 75 318 ml column ((17-1070-01 GE Healthcare, Uppsala, Sweden) was then used to polish and buffer-exchange the proteins to Phosphate Buffered Saline (PBS). Majority of refolded human PGLYRP1 proteins was in monomer form. After concentrating, the final protein concentration was determined by measuring 280 nm absorbance with a NANODROP UV spectrometer. Protein purity was assessed by sodium dodecyl sulfate polyacrylamide gel electrophoresis (SDS-PAGE).

Example 6

Creation of a TREM-1 Responsive Reporter Assay

The TREM-1 reporter cell line was generated by transfecting the BWZ.36 cell line with a NFAT-LacZ reporter construct, as well as hTREM-1 and DAP12 (as described in Example 1). Neutrophils of healthy donors were purified by means of Dextran sedimentation. Blood was stratified on FicollPaque (17-0840-03, GE Healthcare, Piscataway, N.J., USA) gradient with a rate of 3 parts of Ficoll and 4 parts of blood in a 50 ml tube, then centrifuged at 400×g for 30 minutes at 22° C., without brake. The intermediate PBMC band was gently removed by aspiration. The neutrophils stratified on the packed RBC were aspirated and transferred to a 50 ml polypropylene tube. The neutrohils and contaminating RBCs were diluted to 40 ml with 1×PBS and followed by addition of 10 ml 4% DEXTRAN 500 (Sigma, 31392, St Louis, Mo., USA) in PBS solution. After mixing by gentle inversion, the tubes were left at 22° C. for 20-30 min. A granulocyte rich supernatant was then transferred into a fresh tube and centrifuged at 250×g, 5 min, 22° C.; the supernatant was aspirated and discarded. Contaminating RBCs were removed with an osmotic lysis, briefly, the cell pellet was resuspended in 7.5 ml of 0.2% NaCl; gently mixed for 55-60 seconds and 17.5 ml of a 1.2% NaCl. solution was added. The volume was then brought to 50 ml with PBS and spun at 250×g for 5 min, the pellet was resuspended in 7.5 ml of 0.2% NaCl to repeat the lysis a second time. The final granulocyte pellet was resuspended in RPMI/10% FBS. These neutrophils were stimulated with PGN (InVivogen, tlrl-pgnsa, SanDiego, Calif., USA) overnight to generate activated neutrophils able to stimulate TREM-1. The BWZ/hTREM-1 reporter cells were then added to the PGN activated neutrophil cultures in a 1:3 ratio of reporter cell:neutrophils. Instead of activated neutrophils, a TREM-1 ligand complex consisting of PGLYRP1 (SEQ ID NO: 23) and PGN could be used to stimulate TREM-1. The assay was run in Poly-D-Lysine coated Black cell culture plates (no. 356640 from BD Biosciences, San Jose, Calif., USA). TREM-1 activation was read out after 24 hours of culture using the BetaGlo reagent (E4720 from Promega, Madison, Wis., USA) and luminescence measured using a TopCount Luminescence counter from Perkin Elmer. As positive control TREM-1 could be activated by a plate-bound TREM-1 antibody (R&D MAB1278, Minneapolis, Minn., USA) able to agonise TREM-1. Plates were coated with isotype control or TREM-1 antibody MAB1278 (3 ug/ml in PBS, 100 ul/well) in the fridge O/N or for 2 hr at 37° C., 5% CO2 before the BWZ/hTREM-1 reporter cells were added. After 6-24 hours incubation TREM-1 activation could be read using the BetaGlo reagent (E4720 from Promega, Madison, Wis., USA) and luminescence measured using a TopCount Luminescence counter from Perkin Elmer. This BWZ.36/hTREM-1:DAP12:NFAT-LacZ cell line (the "BWZ/hTREM-1 reporter cell") showed to be highly responsive to antibody-mediated cross linking of TREM-1, giving a ~40-fold induction of the NFAT-driven LacZ production when stimulated with 1-10 μg/ml plate bound commercially available anti-TREM-1 antibody, as compared to the isotype control (FIG. 1). When stimulated with a toll-like receptor cocktail (tlrl-kit2hm, Invivogen, Sigma-Aldrich Denmark) alone (BWZ+TLR) no increase in signal was observed. Furthermore, unactivated neutrophils could not stimulate TREM-1, whereas TLR agonist cocktail (tlrl-kit2hm, Invivogen, Sigma-Aldrich Denmark) activated netrophils could stimulate the BWZ/hTREM-1 reporter cell.

Table 1, below, shows that TREM-1 antibodies disclosed herein are able to block the ligand-induced TREM-1 activation in such BWZ/hTREM-1 reporter cell assay.

TABLE 1

| Antibody | Luminescence ×10E6 |
| --- | --- |
| BWZ + activated neutrophils | 8.8 |
| MAB1278 | 10 |
| HPA | 7.9 |
| TREM26 | 9.9 |
| TREM37 | 6.1 |
| 14F128 | 0.3 |
| 14F69 | 0.4 |
| 14F116 | 0.7 |
| 14F11 | 0.4 |
| 14F113 | 0.3 |

None of the tested commercial available antibodies: MAB1278 (cat. no. MAB1278, R&D Systems, Minneapolis, Minn. 55413, USA), anti-TREM-1 HPA (cat. no. HPA005563, Sigma, St Louis, Mo., USA), TREM26 (cat. no. 314902, Biolegend, San Diego, Calif. 92121, USA) and TREM37 (cat. no. 316102, Biolegend, San Diego, Calif. 92121, USA) were able to block the TREM-1 signal.

Example 7

Epitope Mapping Using HX-MS

Materials
Protein batches used were:
hTREM-1: human recombinant TREM-1, non-glycosylated, produced in *E. coli*. (cat. no. PRO-457, ProSpec-Tany TechnoGene Ltd., Rehovot, Israel).

TABLE 2

| mAbs used | |
| --- | --- |
| Antibody | Supplier |
| mAb 0023 | — |
| mAb 0024 | — |
| mAb 0025 | — |
| mAb 0026 | — |
| MAB1278 | RnD Systems |
| TREM26 | BioLegend |

All proteins were buffer exchanged to PBS pH 7.4 before experiments.

Methods: HX-MS Experiments
Instrumentation and Data Recording

The HX experiments were automated by a Leap robot (H/D-x PAL; Leap Technologies Inc.) operated by the Leap-Shell software (Leap Technologies Inc.), which performed initiation of the deuterium exchange reaction, reaction time control, quench reaction, injection onto the UPLC system and digestion time control. The Leap robot was equipped with two temperature controlled stacks maintained at 20° C. for buffer storage and HX reactions and maintained at 2° C. for storage of protein and quench solution, respectively. The Leap robot furthermore contained a cooled Trio VS unit (Leap Technologies Inc.) holding the pre- and analytical columns as well as the pepsin column, the LC tubing and switching valves at 1° C. The switching valves of the Trio VS unit have been upgraded from HPLC to Microbore UHPLC switch valves (Cheminert, VICI AG). For the inline pepsin digestion, 100 µL quenched sample containing 200 pmol hTREM-1 was loaded and passed over the Poroszyme® Immobilised Pepsin Cartridge (2.1×30 mm (Applied Biosystems)) using a isocratic flow rate of 200 µL/min (0.1% formic acid:$CH_3CN$ 95:5). The resulting peptides were trapped and desalted on a VanGuard pre-column BEH C18 1.7 µm (2.1×5 mm (Waters Inc.)). Subsequently, the valves were switched to place the pre-column inline with the analytical column, UPLC-BEH C18 1.7 µm (2.1×100 mm (Waters Inc.)), and the peptides separated using a 9 min gradient of 15-35% B delivered at 200 µl/min from an AQUITY UPLC system (Waters Inc.). The mobile phases consisted of A: 0.1% formic acid and B: 0.1% formic acid in $CH_3CN$. The ESI MS data, and the separate data dependent MS/MS acquisitions (CID) and elevated energy ($MS^E$) experiments were acquired in positive ion mode using a Q-TOF Premier MS (Waters Inc.). Leucine-enkephalin was used as the lock mass ($[M+H]^+$ ion at m/z 556.2771) and data was collected in continuum mode (For further description of the set-up, see Andersen and Faber, Int. J. Mass Spec., 302, 139-148 (2011)).

Data Analysis

Peptic peptides were identified in separate experiments using standard CID MS/MS or $MS^E$ methods (Waters Inc.). $MS^E$ data were processed using BiopharmaLynx 1.2 (version 017). CID data-dependent MS/MS acquisition was analyzed using the MassLynx software and in-house MASCOT database.

HX-MS raw data files were subjected to continuous lock mass-correction. Data analysis, i.e., centroid determination of deuterated peptides and plotting of in-exchange curves, was performed using prototype custom software (HDX browser, Waters Inc.) and HX-Express ((Version Beta); Weis et al., J. Am. Soc. Mass Spectrom. 17, 1700 (2006)). All data were also visually evaluated to ensure only resolved peptide isotopic envelopes were subjected to analysis.

Epitope Mapping Experiment

Amide hydrogen/deuterium exchange (HX) was initiated by a 6-8 fold dilution of hTREM-1 in the presence or absence of mAb into the corresponding deuterated buffer (i.e. PBS prepared in $D_2O$, 96% $D_2O$ final, pH 7.4 (uncorrected value)). All HX reactions were carried out at 20° C. and contained 4 µM hTREM-1 in the absence or presence of 4 µM mAb thus giving a 2 fold molar excess of mAb binding sites. At appropriate time intervals ranging from 10 sec to 10000 sec, 50 µl aliquots of the HX reaction were quenched by 50 µl ice-cold quenching buffer (1.35M TCEP) resulting in a final pH of 2.5 (uncorrected value).

Results and Discussion

This experiment maps the epitopes of mAbs 0023, 0024, 0025, 0026 and the commercial mAbs MAB1278 (RnD Systems) and Clone26 (Biolegend) on hTREM-1. The HX time-course of 43 peptides, covering 94% of the primary sequence of hTREM-1, were monitored in the absence or presence of the eight different mAbs for 10 to 10000 sec.

Exchange protection observed in the early time-points, e.g. <300 sec, relate to surface exposed amide protons and thus also relate to protein interfaces. In contrast, effects observed late in the time course are related to slow exchanging amide hydrogens and thus related to the structural core of the protein. Therefore, epitope effects appear in the early time points whereas structural stabilization effects will manifest as exchange reduction in late time points (Garcia, Pantazatos and Villareal, Assay and Drug Dev. Tech. 2, 81 (2004); Mandell, Falick and Komives, Proc. Natl. Acad. Sci. USA, 95, 14705 (1998)).

The observed exchange pattern in the early timepoints in the presence or absence of a given mAb can be divided into two different groups: One group of peptides display an exchange pattern that is unaffected by mAb binding. In contrast, another group of peptides in hTREM-1 show protection from exchange upon mAb binding. For example at 100 sec exchange with $D_2O$, approx than 2 amides are protected from exchange in the region Y111-F126 of mAb 0023. Regions displaying such protection effects are assigned to the epitope region.

Epitope Mapping of mAbs 0023 and 0026 mAbs 0023 and 0026 both induce identical alterations in the exchange profile of hTREM-1 and will be described together here. The regions displaying protection upon 0023/0026 binding encompass peptides covering residues T22-L96 and Y111-D127. However, by comparing the relative amounts of exchange protection within each peptide upon binding mAb 0023/0026 and the lack of epitope effects in peptides T25-F48, R84-Q112 and peptides starting at P118, the epitope can be narrowed to residues A21-E26, A49-I85 and C113-P119. Although distant in sequence, these regions are close in the 3D structure of hTREM-1.

Epitope Mapping of mAb 0024 and Biolegend Clone 26 mAb 0024 and Clone26 from Biolegend both induce identical alterations in the exchange profile of hTREM-1 and will be described together here. The regions displaying protection upon mAb 0024 binding encompass peptides covering residues V101-Q112. By comparing the relative amounts of exchange protection within each peptide upon binding mAb 0024 and the lack of epitope effects in surrounding peptides, the epitope can be narrowed to residues Q104-Q112 (FIG. 7B).

Epitope Mapping of NNC mAb 0025

Figure 8:
FIG. 8: Structural mapping of the epitope of mAb 0025 on hTREM-1. The structure of hTREM-1 (pdb 1Q8M) is represented with one part of the dimer as black C-alpha wire. The other part of the hTREM-1 dimer is shown in grey ribbon with the 0025 epitope displayed in black.

The regions displaying protection upon 0025 binding encompass peptides covering residues D38-M63, T70-L96 and Y111-D127 (FIG. 7C). However, by comparing the relative amounts of exchange protection within each peptide upon binding 0254-0025 and the lack of epitope effects in peptides in surrounding regions, the epitope can be narrowed to residues V39-Q56, T70-I85 and C113-P119. Although distant in sequence, these regions are close in the 3D structure of hTREM-1 (FIG. 8).

Epitope Mapping of MAB1278

The regions displaying protection upon MAB1278 binding encompass peptides covering residues T70-L96 and V101-Q112 (FIG. 7D). However, by comparing the relative amounts of exchange protection within each peptide upon binding MAB1278 and the lack of epitope effects in peptides in surrounding regions, the epitope can be narrowed to residues T70-I85 and Q104-Q112. Although distant in sequence, these regions are close in the 3D structure of hTREM-1.

The structural position of the epitopes of mAbs 0023/0026 and mAb 0025 are shown in FIG. 7A. The epitope of mAbs 0023 and 0026 seems to reside primarily in β-sheets in the dimer interface of the hTREM-1 crystal structure dimer. The antagonism of these mAbs could be a result of preventing hTREM-1 dimerisation and thus signalling.

Example 8

Determination of the Interaction Interface Between TREM-1 and mAb 0170

Epitopes were mapped on both recombinant human and cynomolgus monkey TREM-1 (hTREM-1 and cTREM-1, respectively). The hTREM-1 construct used in this example comprises the residues M1-H140 (SEQ ID NO: 18) and the cTREM-1 construct comprises the residues M1-R180 of (SEQ ID NO: 12) with six histidine residues added to the C-terminus and using the amino acid numbering from wild-type hTREM-1. Throughout this example the amino acids of cTREM-1 are numbered according to the analogous residue in hTREM-1, as illustrated in FIG. 11. The numbering used in this example can be converted to the numbering in SEQ ID NO: 12 by subtracting 19 if the residue number is 58 or less and by subtracting 20 if the residue number is 60 or greater. As an example, the residue number E46 on cTREM-1 in this example corresponds to residue (46−19=27) E27 in SEQ ID NO: 12. The residue number on L96 on cTREM-1 in this example corresponds to residue (96−20=76) L76 in SEQ ID NO: 12.

Solutions of TREM-1, alone or in the presence of mAb 0170, were diluted 25-fold in 97% deuterated hepes buffer (20 mM hepes, 150 mM sodium chloride, pH 7.4). Non-deuterated controls were prepared by diluting into protiated hepes buffer. The hydrogen exchange experiments were performed on a waters HDX nanoAcquity ultra-high performance liquid chromatography (UPLC) system (Waters Corporation, Milford, Mass., USA) which included the HD-x PAL auto sampler (LEAP Technologies Inc., Carrboro, N.C., USA) for automated sample preparation. The LC tubing, pre- and analytical columns and switching valves were located in a chamber cooled to 0.3° C. The trypsin digestion column was stored at 15° C. Hydrogen exchange reactions were performed at 20° C. Mass analysis was performed online using a Waters SYNAPT G2 HDMS mass spectrometer.

A volume containing 100 pmol of human or cynomolgus TREM-1 (1.54-1.98 µl) with or without 120 pmol mAb 0170 was diluted into deuterated hepes buffer to a final volume of 50 µl. At the appropriate time intervals the entire volume was transferred to and quenched in 50 µl 1.35 mM Tris(2-carboxy-ethyl)phosphine adjusted to pH 2.4 and held at 3° C. 99 µl of the quenched solution was immediately injected and passed over a Porozyme immobilised pepsin column (2.1 mm×30 mm) (Applied Biosystems, Life Technologies Corporation, Carlsbad, Calif., USA) and trapped on a Waters VanGuard BEH C18 1.7 µm (2.1 mm×5 mm) column at 100 µl/min flowrate using a 5% (vol/vol) methanol and 0.1% formic acid mobile fase. The peptides were separated on a Waters UPLC BEH C18 1.7 µm (1.0 mm×100 mm) column using a 10-40% acetonitrile gradient containing 0.1% formic acid at a 40 µl/min flow-rate.

The mass spectrometer was operated in positive ion mode with ion mobility separation enabled. The electrospray conditions were 3.2 kV capillary, 25 V sample cone, and 4 V extraction cone offsets, 850 ml/min flow of nitrogen desolvation gas heated to 350° C. and 50 ml/min cone gas flow. The source block was heated to 120° C. Lock-mass correction data was acquired using the 1+ ion of Leucine-enkephalin (m/z 556.2771) as reference compound and applied during data analysis. For peptide identification $MS^E$-type experiments using trap collision offsets of 6 V (low-energy) and 50 V (elevated energy) were performed. Deuterated samples were analysed using the 6 V low energy trap collision offset only. For further details see Andersen, M. D., Faber, J. H., *Int. J. Mass Spectrom.* (2011), 302, 139-148.

The $MS^E$-data was analysed using Waters ProteinLynx Global Server 2.5 and peptides of hTREM-1 were identified that covered 80% of the protein sequence (Table 3) and peptides of cTREM-1 were identified that covered 100% of the protein sequence (Table 4). The HX-MS data files were analysed using Waters DynamX 1.0 that automatically applies lock-mass correction and determines the degree of deuterium incorporation in each peptide. In addition, all data was manually inspected to ensure correct peak assignment and calculation of deuterium incorporation.

Results

A list of the peptides and their exchange patterns is provided in Table 3.

When mAb 0170 bound hTREM-1, protection from exchange was observed in peptides covering the sequence from A21 to L96 and the epitope was consequently determined to be within this region. When taking into account peptides that show no protection from exchange upon binding of mAb 0170, the epitope could be narrowed to the regions D38-F48. The region from R84-L96 showed little to no exchange in the presence or the absence of mAb 0170 and it was not possible to conclude whether this region was part of the mAb 0170 binding epitope. The peptide K47-A68 didn't show protection from exchange upon binding of mAb 0170, but the peptide T44-C69 was protected when mAb 0170 was bound. The first two residues of a peptide back-exchanges quickly and exchange information for those residues is lost. It was concluded that at least one of the residues E46, K47, and F48 was important for the binding of mAb 0170.

TABLE 3

Results from HXMS epitope mapping of mAb 0170 on human TREM-1

| Peptide | mAb 0170 |
|---------|----------|
| A21-L37 | N |
| A21-D38 | N |
| A21-V39 | N |

TABLE 3-continued

Results from HXMS epitope mapping
of mAb 0170 on human TREM-1

| Peptide | mAb 0170 |
|---|---|
| A21-C69 | EX |
| T22-D38 | N |
| D38-Q56 | EX |
| D38-M63 | EX |
| D38-L67 | EX |
| D38-A68 | EX |
| D38-C69 | EX |
| V39-A68 | EX |
| V39-C69 | EX |
| D42-C69 | EX |
| T44-C69 | EX |
| K47-A68 | N |
| A49-C69 | N |
| I57-A68 | N |
| I57-C69 | N |
| I57-L87 | N |
| L67-L87 | N |
| A68-E88 | N |
| A68-L96 | N |
| C69-L87 | N |
| C69-L96 | N |
| T70-L87 | N |
| T70-E88 | N |
| T70-L96 | N |
| R84-L96 | LE |
| E88-L96 | LE |
| Q104-L110 | N |
| Y111-M124 | N |
| Y111-F126 | N |
| Y111-D127 | N |
| C113-F126 | N |
| V114-F126 | N |
| V114-D127 | N |
| I115-F126 | N |
| I115-D127 | N |

EX: Epitope region indicated by hydrogen exchange protection upon antibody binding.
(Exhange difference (EX) > 0.8 deuterons)
W: Weak exchange due to structural effects (0.1 < EX < 0.8).
N: No protection from exchange upon antibody binding. (EX < 0.1)
LE: Low intrinsic exchange mAb 0170 Epitope on cTREM-1

A list of the peptides and their exchange patterns is given in Table 4.

When mAb 0170 bound to cTREM-1, protection from exchange was observed in peptides covering the sequence from E38 to A68 and the epitope was consequently determined to be within this region. When taking into account peptides that show no protection from exchange upon binding of mAb 0170, the epitope could be narrowed to the regions E38-L45. This epitope corresponded well with the mAb 0170 epitope on hTREM-1 but was truncated by three residues. The peptide C44-T69 in hTREM-1 was protected upon binding of mAb 0170, but the peptides A44-L67 and A44-A68 that cover the corresponding sequence in cTREM-1 were not protected. Thus, whereas at least one of the residues E46, K47, and F48 in hTREM-1 contributed to the binding epitope the corresponding residues E46, K47, and Y48 were not involved in binding of mAb 0170 to cTREM-1.

TABLE 4

HXMS epitope mapping of mAb 0170 on cynomolgus TREM-1

| Peptide | mAb0170 |
|---|---|
| T21-L37 | W |
| L24-L37 | W |
| T25-L37 | W |

TABLE 4-continued

HXMS epitope mapping of mAb 0170 on cynomolgus TREM-1

| Peptide | mAb0170 |
|---|---|
| T25-E38 | W |
| E38-L67 | EX |
| E38-A68 | EX |
| V39-L67 | EX |
| V39-A68 | EX |
| K40-L67 | EX |
| A44-L67 | W |
| A44-A68 | W |
| E46-L67 | N |
| K47-L67 | N |
| A68-L87 | W |
| A68-L96 | W |
| A68-Q97 | W |
| K69-L87 | W |
| K69-L96 | W |
| V82-L96 | W |
| E88-L96 | LE |
| E88-Q97 | LE |
| Q97-L103 | N |
| Q104-L110 | N |
| Y111-C130 | W |
| Y111-L131 | W |
| V114-L131 | W |
| I115-C130 | W |
| I115-L131 | W |
| L131-T180 | W |
| L131-V182 | W |
| V132-T180 | W |
| V132-V182 | W |
| Y152-T180 | W |
| V181-E189 | N |
| V181-H206 | W |
| I190-H206 | N |
| T193-H206 | N |
| V195-H206 | N |
| T196-H206 | N |
| D197-H206 | N |

EX: Epitope region indicated by hydrogen exchange protection upon antibody binding.
(Exhange difference (EX) > 0.8 deuterons)
W: Weak exchange due to structural effects (0.1 < EX < 0.8).
N: No protection from exchange upon antibody binding. (EX < 0.1)
LE: Low intrinsic exchange

Example 9

Study of Interaction Kinetics for Anti TREM-1 Antibodies to Human and Cynomolgus TREM-1 by Surface Plasmon Resonance (SPR)

Binding studies were performed on a ProteOn Analyzer (BioRad) that measures molecular interactions in real time through surface plasmon resonance. Experiments were run at 25° C. and the samples were stored at 15° C. in the sample compartment. The signal (RU, response units) reported by the ProteOn is directly correlated to the mass on the individual sensor chip surfaces in six parallel flow cells. Anti-human Fc monoclonal or anti-murine Fc polyclonal antibody from Biacore human or mouse Fc capture kits were immobilized in horizontal direction onto flow cells of a GLM sensor chip according to the manufacturer's instructions. The final immobilization level of capture antibody was approximately 2600-6000 RU in different experiments. Capture of purified monoclonal mouse or recombinant expressed anti-hTREM-1 antibodies was conducted by diluting the antibodies to 5-10 nM into running buffer (10 mM Hepes 0.15 M NaCl, 5 mM EDTA, 0.05% surfactant P20, pH 7.4) and injected in vertical direction at 30 µl/min for 60 s, creating reference interspots adjacent to all flow cells with only anti-Fc antibody immobilized. This typically resulted in final capture levels of test antibodies of approximately 100-300 RU and Rmax values of analyte of 30-90 RU. Binding of hTREM-1 or cTREM-1 proteins was conducted by injecting analyte (antigen) over all flow cells in horizontal direction to allow for comparative analyses of binding to different captured anti-TREM-1 antibodies relative to binding to the reference interspot. hTREM-1 or cTREM-1 proteins was diluted serially 1:3 to 1.2-100 nM or into running buffer, injected at 100 µl/min for 250 s and allowed to dissociate for 600 s. The GLM surface was regenerated after each injection cycle of analyte via two 18 s injections of 10 mM Glycine, pH 1.7 and 50 mM NaOH at 100 µl/min. This regeneration step removed the anti-TREM-1 antibody and any bound TREM-1 protein from the immobilized capture antibody surface, and allowed for the subsequent binding of the next interaction sample pair. The regeneration procedure did not remove the directly immobilized anti-Fc capture antibody from the chip surface.

Binding affinity between antibodies and the antigen was quantified by determination of the equilibrium dissociation constant ($K_D$) determined by measurement of the kinetics of complex formation and dissociation. The rate constants corresponding to the association and the dissociation of a monovalent complex such as $k_a$ (association rate) and $k_d$ (dissociation rate) were retrieved by fitting data to 1:1 Langmuir model using the ProteOn evaluation software for data analysis. $K_D$ is related to $k_a$ and $k_d$ through the equation $K_D = k_d/k_a$. Binding curves were processed by double referencing (subtraction of reference surface signals as well as blank buffer injections over captured anti-TREM-1 antibodies) prior to data analysis. This allowed correction for instrument noise, bulk shift and drift during sample injections.

TABLE 5

Results from measurements of binding constants ka (association rate), kd (dissociation rate) and KD (equilibrium dissociation constant) for the interaction of human TREM-1 to different anti-TREM-1 monoclonal antibodies.

| mAb | Clone | Origin | ka (1/(Ms) | kd (1/s) | KD (M) |
|---|---|---|---|---|---|
| mAb 0023 | 5F8A1 | Hybridoma | 1.0E+05 | 2.2E−04 | 2.1E−09 |
| mAb 0024 | 5F28A1 | Hybridoma | 7.8E+04 | 3.6E−04 | 4.6E−09 |
| mAb 0025 | 5F19A1 | Hybridoma | 8.8E+05 | 8.5E−04 | 9.7E−10 |
| mAb 0026 | 5F27A1 | Hybridoma | 6.2E+04 | 9.7E−05 | 1.5E−09 |
| mAb 0030 | 5F17A1B2 | Hybridoma | 1.2E+05 | 4.2E−04 | 3.6E−09 |
| mAb 0031 | 13F6A1 | Hybridoma | 1.2E+06 | 3.7E−03 | 3.1E−09 |
| mAb 0032 | 13F10A1 | Hybridoma | 1.1E+06 | 2.1E−03 | 1.9E−09 |
| mAb 0033 | 9F11A1 | Hybridoma | 7.8E+04 | 1.1E−03 | 1.5E−08 |
| mAb 0034 | 14F17A1 | Hybridoma | 1.9E+05 | 1.9E−04 | 1.0E−09 |
| mAb 0039 | 5F8A1 on mIgG2aa | Recombinant | 8.9E+04 | 1.6E−04 | 1.8E−09 |
| mAb 0040 | 5F8A1 on mIgG1 | Recombinant | 9.3E+04 | 2.0E−04 | 2.2E−09 |
| mAb 0041 | 5F27 on mIgG2aa | Recombinant | 7.9E+04 | 1.8E−04 | 2.3E−09 |
| mAb 0042 | 5F27A1 on mIgG1 | Recombinant | 8.5E+04 | 2.5E−04 | 2.9E−09 |
| mAb 0044 | 14F69A1 | Hybridoma | 1.5E+06 | 2.9E−04 | 2.0E−10 |
| mAb 0045 | 13F14A1 | Hybridoma | 1.3E+06 | 3.2E−03 | 2.5E−09 |
| mAb 0046 | 14F70A1 | Hybridoma | 9.3E+05 | 1.9E−04 | 2.1E−10 |
| mAb 0048 | 14F11A1B1 | Hybridoma | 1.7E+06 | 3.9E−03 | 2.4E−09 |
| mAb 0049 | 14F86A1 | Hybridoma | 8.8E+05 | 1.3E−03 | 1.5E−09 |
| mAb 0051 | 5F24 HC645/LC647 | Recombinant | 6.8E+05 | 3.0E−03 | 4.5E−09 |
| mAb 0054 | 14F128A1 | Hybridoma | 1.6E+06 | 3.8E−03 | 2.4E−09 |
| mAb 0059 | 14F113/14F69 | Recombinant | 1.7E+06 | 5.2E−04 | 3.2E−10 |
| mAb 0063 | 14F116A1B1 | Hybridoma | 1.0E+06 | 1.4E−03 | 1.4E−09 |
| mAb 0064 | 14F20A1B1 | Hybridoma | 8.9E+05 | 1.3E−03 | 1.5E−09 |
| mAb 0067 | 14F11A1B1 | Recombinant | 2.2E+06 | 3.9E−03 | 2.0E−09 |
| mAb 0068 | 14F128/14F11 | Recombinant | 2.7E+06 | 3.9E−03 | 1.7E−09 |
| mAb 0070 | 14F113/14F69 | Recombinant | 2.1E+06 | 4.3E−04 | 2.5E−10 |
| mAb 0078 | 14F106A2 | Hybridoma | 9.8E+05 | 1.4E−03 | 1.5E−09 |
| mAb 0079 | 14F29A1B1 | Hybridoma | 2.6E+05 | 1.2E−03 | 4.6E−09 |
| mAb 0080 | 14F17A1B1 | Hybridoma | 2.7E+05 | 1.9E−04 | 7.1E−10 |
| mAb 0083 | 14F116A1B1 | Recombinant | 1.0E+06 | 1.7E−03 | 1.7E−09 |
| mAb 0090 | 14F113 fully humanized | Recombinant | 2.1E+06 | 1.5E−03 | 7.7E−10 |
| mAb 0115 | 14F113HC/14F128LC mixed and humanized | Recombinant | 1.8E+06 | 2.4E−02 | 1.6E−08 |
| mAb 0120 | 14F113/14F69 hz variant HC A78L | Recombinant | 2.2E+06 | 1.5E−03 | 6.7E−10 |
| mAb 0121 | 14F113/14F69 hz variant HC T93V | Recombinant | 2.8E+06 | 1.7E−03 | 6.3E−10 |
| mAb 0122 | 14F113/14F69 hz variant LC M4L | Recombinant | 2.5E+06 | 1.4E−03 | 6.0E−10 |
| mAb 0124 | 14F113/14F69 hz variant LC G68R | Recombinant | 2.0E+06 | 1.2E−03 | 6.1E−10 |
| mAb 0170 | 14F113/14F69 hz variant LC Q98I | Recombinant | 2.9E+06 | 5.4E−04 | 1.9E−10 |

TABLE 6

Results from measurements of binding constants ka (association rate), kd (dissociation rate) and KD (equilibrium dissociation constant) for the interaction of cynomolgus TREM-1 to different anti-TREM-1 monoclonal antibodies.

| mAb | Clone | Origin | ka (1/(Ms) | kd (1/s) | KD (M) |
|---|---|---|---|---|---|
| mAb 0048 | 14F11A1B1 | Hybridoma | 1.4E+05 | 1.7E−04 | 1.2E−09 |
| mAb 0059 | 14F113A1B1C1 | Recombinant | 1.8E+05 | 1.2E−04 | 6.7E−10 |
| mAb 0067 | 14F11A1B1 | Recombinant | 3.8E+05 | 1.7E−03 | 4.7E−09 |
| mAb 0068 | 14F128/14F11 | Recombinant | 2.8E+05 | 3.4E−03 | 1.2E−08 |
| mAb 0083 | 14F116A1B1 | Recombinant | No binding | No binding | No binding |

TABLE 6-continued

Results from measurements of binding constants ka (association rate), kd (dissociation rate) and KD (equilibrium dissociation constant) for the interaction of cynomolgus TREM-1 to different anti-TREM-1 monoclonal antibodies.

| mAb | Clone | Origin | ka (1/(Ms) | kd (1/s) | KD (M) |
|---|---|---|---|---|---|
| mAb 0090 | 14F113 fully humanized | Recombinant | 1.4E+05 | 3.0E−04 | 2.1E−09 |
| mAb 0121 | 14F113 hz variant HC T93V | Recombinant | 1.3E+05 | 1.3E−04 | 9.4E−10 |
| mAb 0122 | 14F113 hz variant LC M4L | Recombinant | 1.7E+05 | 1.6E−04 | 9.7E−10 |
| mAb 0124 | 14F113 hz variant LC G68R | Recombinant | 1.7E+05 | 2.0E−04 | 1.1E−09 |
| mAb 0170 | 14F113 hz variant LC Q98I | Recombinant | 2.5E+05 | 8.9E−04 | 3.6E−09 |

Example 10

Humanisation of the Blocking TREM-1 mAb 14F69

The variable regions of two lead antibodies were obtained from cloning of hybridomas 14F128A1 and 14F113A1B1C1. Both antibodies were cloned using the SMARTER-RACE technique (Clontech). The humanization effort was performed as an iterative loop where CDR grafted antibodies were first affinity evaluated and then re-engineered to include more backmutations until an acceptable affinity was retained, using hybridoma purified antibodies as a benchmark. The CDR grafted antibodies were designed in silico and ordered from a commercial vendor (www.genscript.com). Subsequent re-engineering of antibodies was performed using site directed mutagenesis (Stratagene). All antibodies were expressed in HEK293-6E cells in preparation for affinity testing. Below is a description of the main considerations for selection of appropriate human germline and test of backmutations. All numbering of variable regions used in this example refers to the Kabat numbering scheme.

>m14F128A1_H (CDRs marked with bold and underligned) (SEQ ID NO 8)>

>m14F128A1_L (CDRs marked with bold) (SEQ ID NO 9)

>m14F113A1B1C1_H (CDRs marked with bold) (SEQ ID NO 10)

>m14F113A1B1C1_L (CDRs marked with bold) (SEQ ID NO 11)

From an analysis of the sequences, the CDRs for m14F128A1 according to Kabats definition are:

```
>CDR_H1
TYAMH

>CDR_H2
RIRTKS[N/S]NYATYY[V/A]DSVKD

>CDR_H3
DMG[I/A]RRQFAY

>CDR_L1
RASESVD[S/T]F[G/D][I/Y]SF[M/L]H

>CDR_L2
RASNLES

>CDR_L3
QQSNEDPYT
```

With the differences between m14F128A1 and m14F113A1B1C1 given as [m14F128A1/m14F113A1B1C1].

A 3D model of m14F128A1 was build using standard techniques in MOE [available from www.chemcomp.com] and all residues within 4.5 Å of the effective CDR regions (VH: 31-35B, 50-58, 95-102; VL: 24-34, 50-56, 89-97) were defined as mask residues. Mask residues are all potentially important for sustaining the binding in the CDRs.

The mask residues included positions 1-2,4,27-37, 47, 49-59, 69, 71, 73, 78, 92-103 for the heavy chain and positions 1-5,7,23-36, 46, 48-56, 58, 62, 67-71, 88-98 for the light chain.

Using germline searches of m14F128A1 and manual inspection, VH3_73 and JH4 were identified as being an appropriate human germline combination for the heavy chain and VKIV_B3 and JK2 were identified as the appropriate human germline combination for the light chain.

```
>VH3_13/JH4
EVQLVESGGGLVQPGGSLKLSCAASGFTFSGSAMHWVRQASGKGLEWVGR

IRSKANSYATAYAASVKGRFTISRDDSKNTAYLQMNSLKTEDTAVYYCT

R/YFDYWGQGTLVTVSS

>VKIV_B3/JK2
DIVMTQSPDSLAVSLGERATINCKSSQSVLYSSNNKNYLAWYQQKPGQPP

KLLIYWASTRESGVPDRFSGSGSGTDFTLTISSLQAEDVAVYYCQQYYST

P/YTFGQGTKLEIKR
```

Humanisation was then performed with the following rules:

Residues outside the mask were taken as human.

Residues inside the mask and inside the Kabat CDR were taken as murine.

Residues inside the mask and outside the Kabat CDR with mouse/germline consensus were taken as the consensus sequence.

Residues inside the mask and outside the Kabat CDR with mouse/germline difference were subject to potential back mutations.

Grafting the effective CDR regions of m14F128A1 into the germlines formed the basic humanisation construct of m14F128A1, hz14F128A1.

```
>hz14F128A1_H
EVQLVESGGGLVQPGGSLKLSCAASGFTFSTYAMHWVRQASGKGLEWVGR

IRTKSNNYATYYAASVKGRFTISRDDSKNTAYLQMNSLKTEDTAVYYCTR

DMGIRRQFAYWGQGTLVTVSS
```

```
>hz14F128A1_L
DIVMTQSPDSLAVSLGERATINCRASESVDSFGISFMHWYQQKPGQPPKL

LIYRASNLESGVPDRFSGSGSGTDFTLTISSLQAEDVAVYYCQQSNEDPY

TFGQGTKLEIK

>CDR_H1
TYAMH

>CDR_H2
RIRTKSNNYATYYAASVKG

>CDR_H3
DMGIRRQFAY

>CDR_L1
RASESVDSFGISFMH

>CDR_L2
RASNLES

>CDR_L3
QQSNEDPYT
```

The only differences compared to the murine CDRs were in CDR_H2 (shown in bold). Any discrepancy between m14F128A1 and hz14F128A1 in a mask residue will create a potential backmutation and the list includes:
  hz14F128A1_H: S30N, G49A, A78L, V93T
  hz14F128A1_L: M4L, M58I, G68R Furthermore, the close homology of m14F128A1 and m14F113A1B1C1 was used to suggest residues that could impact the affinity of hz14F128A1.
  hz14F128A1_H: N53S, 198O
  hz14F128A1_L: S27D_T, G29D, I30Y, M33L In order to investigate all potentially humanised mAbs all combinations of the above mutants were produced and tested.

The final humanised anti hTREM1 antibody (mAb 0170) derived from hybridoma 14F113 contains one LC framework-backmutation (M4L) and one HC CDR3 mutation (Q98I). The mutation in HC CDR3 was introduced based on an affinity-synergy-study with a highly homologous antibody named 14F128. The rationale for including both mutations is described below.

Affinity-Synergy Study of Antibody 14F128 and 14F113

The hybridoma antibodies 14F128 and 14F113 are highly homologous and derived from the same somatic recombination event. The two antibodies compete in hTREM1 binding with 14F113 having the highest affinity. In total the CDR grafted versions of the two antibodies differ in their CDR compositions by only six amino acids (four in LC CDR, and two in HC CDR). The six mutations, when comparing 14F113 to 14F128, are LC T27$_d$S, D29G, Y30I, L33M and HC S54N, Q98I. Although CDR grafted 14F128 had an affinity inferior to CDR grafted 14F113 it was investigated if a beneficial affinity effect from one or more of the six mutations was suppressed by the overall effect when all six mutations were present. All six mutations (except HC S54N) were therefore individually introduced in the CDR grafted 14F113 antibody and the antibodies were ranked by affinity. Two mutations (LC L33M and HC Q098I) were individually capable of improving the affinity of CDR grafted 14F113. A mutation of the HC at position Q98I gave rise to a particularly good affinity of the resultant antibody (mAb 0170).

Framework Backmutation Affinity Analysis

The mouse version of the 14F113 antibody had seven mutations that were potentially necessary to include as backmutations during humanisation. The potential backmutations in the HC and LC were S30N, G49A, A78L and T93V M4L, V58I, G68R, respectively. The seven backmutations were introduced individually in CDR grafted 14F113 and then ranked by affinity. Although several of the mutations were capable of improving affinity, only LC mutation M4L was selected for mAb 0170. The decision to include mutations was balanced against expression titer (HEK293 6E), affinity, and the total number of mutations.

Example 11

Study of Interaction Kinetics for TREM-1 Antibodies to hTREM-1 by Surface Plasmon Resonance (SPR): Comparison Between mAb 0170 and Commercially Available TREM-1 Antibodies Binding studies were performed on a ProteOn Analyzer (BioRad) that measures molecular interactions in real time through surface plasmon resonance. Experiments were run at 25° C. and the samples were stored at 15° C. in the sample compartment. The signal (RU, response units) reported by the ProteOn is directly correlated to the mass on the individual sensor chip surfaces in six parallel flow cells. Commercially available antibodies included were Biolegend #314907, Biolegend #316102 (Biolegend, USA), Hycult Biotech HM2252 (Hycult Biotech, Netherlands), R&D #MAB1278 (R&D systems, United Kingdom), SC98Z12 (Santa Cruz Biotechnology, USA), Sigma #WH0054210 m4, Sigma #SAB1405121 (Sigma-Aldrich Danmark A/S)

Anti-human Fc monoclonal or anti-murine Fc polyclonal antibody from Biacore human or mouse Fc capture kits were immobilized in horizontal direction onto flow cells of a GLM sensor chip according to the manufacturer's instructions. The final immobilization level of capture antibody was approximately 2600-6000 RU in different experiments. Capture of purified monoclonal mouse or recombinant expressed humanized anti-hTREM-1 antibodies was conducted by diluting the antibodies to 5-10 nM into running buffer (10 mM Hepes 0.15 M NaCl, 5 mM EDTA, 0.05% surfactant P20, pH 7.4) and injected in vertical direction at 30 µl/min for 60 s, creating reference interspots adjacent to all flow cells with only anti-Fc antibody immobilized. This typically resulted in final capture levels of test antibodies of approximately 100-300 RU and Rmax values of analyte of 30-90 RU. Binding of hTREM-1 or cTREM-1 proteins was conducted by injecting analyte over all flow cells in horizontal direction to allow for comparative analyses of binding to different captured anti-TREM-1 antibodies relative to binding to the reference interspot. hTREM-1 or cTREM-1 proteins was diluted serially 1:3 to 1.2-100 nM or into running buffer, injected at 100 µl/min for 210 s and allowed to dissociate for 600 s. The GLM surface was regenerated after each injection cycle of analyte via two injections of 10 mM Glycine, pH 1.7 and 50 mM NaOH at 100 µl/min. This regeneration step removed the anti-TREM-1 antibody and any bound TREM-1 protein from the immobilized capture antibody surface, and allowed for the subsequent binding of the next interaction sample pair. The regeneration procedure did not remove the directly immobilized anti-Fc capture antibody from the chip surface.

Binding affinity between antibodies and the antigen was quantified by determination of the equilibrium dissociation constant ($K_D$) determined by measurement of the kinetics of complex formation and dissociation. The rate constants corresponding to the association and the dissociation of a monovalent complex such as $k_a$ (association rate) and $k_d$ (dissociation rate) were retrieved by fitting data to 1:1 Langmuir model using the ProteOn evaluation software 3.1.0.6 for data analysis. $K_D$ is related to $k_a$ and $k_d$ through the equation $K_D = k_d/k_a$.

Binding curves were processed by double referencing (subtraction of reference surface signals as well as blank buffer injections over captured anti-TREM-1 antibodies) prior to data analysis. This allowed correction for instrument noise, bulk shift and drift during sample injections.

TABLE 7

Results from measurements of KD (equilibrium dissociation constant) for the interaction of human and cynomolgus TREM-1 to different anti-TREM-1 monoclonal antibodies.

| Antibody | human TREM-1 KD (M) | cyno TREM-1 KD (M) |
|---|---|---|
| mAb 0170 | 2E-10 | 3E-09 |
| Biolegend #314907 | 9E-10 | 4E-09 |
| Biolegend #316102 | 8E-10 | No binding |
| Hycult Biotech HM2252 | 3E-09 | No binding |
| R&D #MAB1278 | 8E-09 | No binding |
| SC98Z12 | 3E-08 | No binding |
| Sigma #WH0054210m4 | 2E-08 | No binding |
| Sigma #SAB1405121 | No binding | No binding |

Example 12

Competition Binding Studies of Anti-Human TREM-1 Monoclonal Antibodies by Surface Plasmon Resonance SPR binding competition studies were performed with monoclonal mouse or recombinant expressed humanised anti-hTREM-1 antibodies in order to discriminate between different binding sites (epitopes). Commercially available antibodies included were Biolegend #314907 (Biolegend, USA) and SC98Z12 (Santa Cruz Biotechnology, USA). Anti hTREM-1 monoclonal antibodies that compete for the same or an overlapping binding site (epitope) on the antigen are not able to bind simultaneously to the antigen and are therefore assigned to the same "bin". Anti-TREM-1 monoclonal antibodies that do not compete for the same or overlapping binding site on the antigen are able to bind simultaneously and are thus assigned to different "bins". Experiments were performed with soluble, human TREM-1 extracellular domain as antigen.

All studies were run at 25° C., and the samples were stored at 15° C. in the sample compartment. Individual anti-TREM-1 monoclonal antibodies and an unrelated control monoclonal antibody were immobilised onto separate flow cells of a GLC sensor chip using a 1:1 mixture of 0.4 M EDAC [1-ethyl-3-(3-dimethylaminopropyl) carbodiimide hydrochloride] and 0.1 M Sulfo-NHS [N-hydroxysulfosuccinimide]. Each antibody was diluted in 10 mM sodium acetate pH 5.0 to a concentration of 25 or 10 (SC98Z12 (80394)) μg/ml, and was immobilised to an individual flow cell at 30 μl/min for 240 s. The antibodies were immobilised to flow cells L1-L6 (including control). After immobilisation of the antibody, the active sites on the flow cell were blocked with 1 M ethanolamine. Immobilisations were performed with activation and deactivation in a horizontal direction creating interspot reference points without immobilised protein. The final immobilisation level of test antibodies ranged from approximately 1100 to 1300 RU in one experiment, except for one antibody (SC98Z12) where only 390 RU was immobilised. Recombinant human TREM-1 was diluted to 100 nM into running buffer (10 mM Hepes 0.15 M NaCl, 5 mM EDTA, 0.05% surfactant P20, pH 7.4). The antigen was injected over immobilised antibodies in horizontal direction at 30 μl/min for 300 s, allowing control of potential unspecific binding both to interspot references and immobilised control antibodies resulting in 150-600 RU captured TREM-1, except for to one antibody (SC98Z12) with low immobilisation level where only 4 RU was captured.

Each antibody (the same ones that had been immobilised) was injected over parallel flow cells in a horizontal direction to allow for comparative analysis of binding to hTREM-1 captured by the primary antibodies relative to binding to both the interspot references and the immobilised control antibodies. Each competing antibody was diluted to 100 nM and injected at 100 μl/min for 250 s. The GLC chip was regenerated after each injection cycle of analyte via two 18 s injections of 1M Formic acid pH 3.5, 3M MgCl2 and 50 mM NaOH at 100 μl/min. This regeneration step removed the TREM-1 antigen and any bound secondary antibody from the immobilised antibody surface, and allowed for the subsequent binding of the next test sample. The regeneration procedure did not remove the directly immobilised anti-TREM-1 test antibody (primary antibody) from the chip surface. Data analysis was performed with the ProteOn Manager™ 3.1.0.6 Software. Capture levels were assessed to ensure that the regeneration step provided a consistent binding surface throughout the sequence of injections. No significant non-specific binding of human TREM-1 neither to the interspot control surfaces nor to immobilised control antibody was observed. Binding curves were processed by subtraction of interspot control surface signals. This allowed correction for instrument noise and bulk shift during sample injections.

The competition results were reported as either positive or negative binding (Table 8). Positive (+) binding indicates that the competing antibody was capable of binding the hTREM-1 simultaneously with the primary antibody (i.e. they do not compete), and the primary and competing antibodies were consequently assigned to different epitope bins. Negative binding indicates that the competing antibody was unable to bind the hTREM-1 simultaneously with the primary antibody (i.e. they do compete), and the primary and competing antibodies were thus assigned to the same epitope bin. The response values in these experiments were significant and allowed for an unambiguous determination of epitope bins of the anti-TREM-1 monoclonal antibodies.

TABLE 8

Ability to bind (+) or to compete (−) for antibodies tested in SPR competition assay. SC98Z12 did not give high enough capture of TREM-1 to evaluate as primary antibody (*).

| | Primary | | | |
|---|---|---|---|---|
| Secondary | Biolegend #314907 | SC98Z12 | mAb 0048 | mAb 0170 |
| Biolegend #314907 | − | * | + | + |
| SC98Z12 | − | * | + | + |
| mAb 0048 | + | * | − | − |
| mAb 0170 | + | * | − | − |

MAb 0170 and mAb 0048 (purified from hybridoma 14F11, which is identical to 14F128) were shown to compete for binding to human TREM-1. Biolegend #314907 and SC98Z12 did not compete with any of these for human TREM-1 binding but competed with each other. These findings conclude that the first two (mAb 0048 and mAb 0170) belong to the same bin (Bin1) while Biolegend #314907 and SC98Z12 belong to another bin (Bin2).

Example 13

Kinetic Analysis of the Interaction Between Fab 0011 and Fab 0170 Binding to Mutated Versions of Human and Cynomolgus TREM-1

Interaction studies were performed by SPR to define differences in the epitopes for 0011 and 0170 anti-human TREM-1 antibodies on human TREM-1. By comparing binding kinetics to human TREM-1 variants with introduced Alanine mutations in known epitopes, as well as partly "humanised" variants of cynomolgus TREM-1, the latter since only mAb 0170 cross reacts with cynomolgus TREM-1, amino acid residues unique for respective epitope were identified.

The hTREM-1 extracellular domain alanine mutant constructs and partly humanised cynomolgus mutant constructs used in this study are summarised in Table 9. All constructs used were variants either of SEQ ID NO:19 (cynomolgus TREM-1 variants) or SEQ ID NO: 20 (human TREM-1 variants) and included a C-terminal-cmyc$^2$-His$^6$ tag for capture in SPR binding kinetics assay. Unless otherwise stated, sequences referred to in this example are numbered according to FIG. 11.

TABLE 9

| TREM-1 variant | Protein | Mutations |
|---|---|---|
| 0221 | human TREM-1 Ala mut 1 | D38A |
| 0222 | human TREM-1 Ala mut 2 | K40A |
| 0223 | human TREM-1 Ala mut 3 | D42A |
| 0224 | human TREM-1 Ala mut 4 | T44A |
| 0225 | human TREM-1 Ala mut 5 | E46A |
| 0226 | human TREM-1 Ala mut 6 | K47A |
| 0227 | human TREM-1 Ala mut 7 | S50A |
| 0228 | human TREM-1 Ala mut 8 | R84A |
| 0229 | human TREM-1 Ala mut 9 | Y90A |
| 0230 | human TREM-1 Ala mut 10 | H91A |
| 0231 | human TREM-1 Ala mut 11 | D92A |
| 0232 | human TREM-1 Ala mut 12 | H93A |
| 0233 | human TREM-1 Ala mut 13 | R97A |
| 0234 | human TREM-1 Ala mut 14 | R99A |
| 0235 | human TREM-1 Ala mut 15 | D127A |
| 0236 | human TREM-1 Ala mut 16 | R128A |
| 0237 | human TREM-1 Ala mut 17 | R130A |
| 0238 | cynomolgus TREM-1 wt | — |
| 0239 | cynomolgus TREM-1 "partly humanised" | A44T, Y48F, N50S, R52Q, E75K, P91H |
| 0240 | cynomolgus TREM-1 "partly humanised with back mutation 1" | A44A, Y48F, N50S, R52Q, E75K, P91H |
| 0241 | cynomolgus TREM-1 "partly humanised with back mutation 2" | A44T, Y48Y, N50S, R52Q, E75K, P91H |
| 0242 | cynomolgus TREM-1 "partly humanised with back mutation 3" | A44T, Y48F, N50N, R52Q, E75K, P91H |
| 0243 | cynomolgus TREM-1 "partly humanised with back mutation 4" | A44T, Y48F, N50S, R52R, E75K, P91H |
| 0244 (SEQ ID NO: 14) | cynomolgus TREM-1 "partly humanised with back mutation 5" | A44T, Y48F, N50S, R52Q, E75E, P91H |
| 0245 (SEQ ID NO: 15) | cynomolgus TREM-1 "partly humanised with back mutation 6" | A44T, Y48F, N50S, R52Q, E75K, P91P |
| 0247 | human TREM-1 wt | — |

Binding studies were performed on a ProteOn Analyzer that measures molecular interactions in real time through surface plasmon resonance. Experiments were run at 25° C. and the samples were stored at 15° C. in the sample compartment. The signal (RU, response units) reported by the ProteOn is directly correlated to the mass on the individual sensor chip surfaces in six parallel flow cells. Anti-His monoclonal antibody was immobilised onto 6 parallel flow cells of a GLM sensor chip using a 1:1 mixture of 0.4 M EDAC [1-ethyl-3-(3-dimethylaminopropyl)carbodiimide hydrochloride] and 0.1 M Sulfo-NHS [N-hydroxysulfosuccinimide]. Antibody was diluted in 10 mM sodium acetate pH 5.0 to a concentration of 25 µg/ml, and was immobilised onto individual flow cells at 30 µl/min for 240 s. After immobilisation of the antibody, the active sites on the flow cells were blocked with 1 M ethanolamine. Immobilisation was performed with all steps in horizontal direction. The final immobilisation level of capture antibody was approximately 8000 RU in one experiment. Cell culture medium from HEK 293 cells expressing wild type or different mutated variants of human or cynomolgus TREM-1 ECD was diluted 40-60 times in running buffer (10 mM HEPES, 150 mM NaCl, 3 mM EDTA, 0.05% surfactant P20, pH 7.4). TREM-1 proteins were injected over immobilised anti-His capture antibody in the vertical direction at 30 µl/min for 60 s. This resulted in 50-250 RU captured TREM-1 and created interspot references with only immobilised capture antibodies but no captured TREM-1 in the horizontal direction. Each Fab was injected over parallel flow cells in the horizontal direction to allow for kinetic analysis of binding to TREM-1 variants captured by anti-His antibody. Prior to injection each Fab was diluted to 0, 5.5 (in one experiment), 16.7 and 50 nM in running buffer, and injected at 100 µl/min for 250 s (association time). The dissociation time following these injections was monitored for 10 minutes. The GLM chip was regenerated after each interaction cycle of TREM-1 and Fab via two 18 s injections of 10 mM Glycine and 50 mM NaOH at 100 µl/min. This regeneration step removed the TREM-1 variants and any bound Fab from the anti-His antibody surface, and allowed for the subsequent binding of the next interaction pair. The regeneration procedure did not remove the directly immobilised anti-His capture antibody from the chip surface.

In order to obtain kinetic data, such as ka (association rate), kd (dissociation rate) and KD (equilibrium dissociation constant), data analysis was performed using the ProteOn Manager™ 3.1.0.6 Software. Capture and binding levels of samples run in duplicates or triplicates were assessed to ensure that the regeneration step provided a consistent binding surface throughout the sequence of injections. No significant unspecific binding to interspot references with only immobilised capture antibody was observed. Binding curves were processed by subtraction of interspot control surface signals, as well as injection of running buffer. This allowed correction for instrument noise and bulk shift during sample injections. The affinity of 0170 Fab and 0011 Fab to different TREM-1 ECD variants where compared to the affinity to wild type human or cynomolgus TREM-1 ECD.

The level of binding 10 s after end of injection of Fab, normalised to level of captured TREM-1 variant, was also assessed in order to identify mutated versions with abrogated or very low binding. A decrease in affinity combined with significantly lower normalised binding level can indicate a disrupted folding due to introduced mutations. It should however be noted that changes in kinetics will also affect this value. Each binding curve was therefore visually inspected for conclusion (data not shown).

Results for human TREM-1 with alanine single mutations (Table 10) show that two positions (E46 and D92) were unique in that they decreased binding more than two-fold to 0170 Fab.

TABLE 10

Affinity of 0170 Fab and 0011 Fab to human TREM-1 with alanine mutations relative to human TREM-1 wt. Binding level of 0170 Fab and 0011 Fab 10 s after end of association, expressed as degree of theoretical maximum binding level.

| | | KD relative to 0247 | | Normalised binding (% Rmax theor) | |
|---|---|---|---|---|---|
| Construct | Mutation | 0170 Fab | 0011 Fab | 0170 Fab | 0011 Fab |
| 0247 | — | 1 | 1 | 44 | 41 |
| 0221 | D38A | 0.7 | 15.0 | 29 | 5 |
| 0222 | K40A | 0.9 | No binding | 43 | 1 |
| 0223 | D42A | 132.9 | 26.9 | 13 | 3 |
| 0224 | T44A | 1.2 | 1.8 | 46 | 40 |
| 0225 | E46A | 2.7 | 0.9 | 44 | 44 |
| 0226 | K47A | 1.0 | 1.1 | 40 | 38 |
| 0227 | S50A | 0.7 | 0.9 | 45 | 41 |
| 0228 | R84A | 0.5 | 1.3 | 15 | 8 |
| 0229 | Y90A | 0.5 | 2.9 | 40 | 31 |
| 0230 | H91A | 0.9 | 2.5 | 41 | 33 |
| 0231 | D92A | 9.2 | 1.1 | 34 | 41 |
| 0232 | H93A | 36.4 | 5.2 | 22 | 29 |
| 0233 | R97A | 1.1 | 6.2 | 36 | 22 |
| 0234 | R99A | 0.8 | 1.0 | 15 | 11 |
| 0235 | D127A | 1.1 | 0.8 | 43 | 41 |
| 0236 | R128A | 0.9 | 1.2 | 39 | 35 |
| 0237 | R130A | 1.0 | 0.8 | 35 | 34 | mAb-0170 was, in contrast to mAb-0011, able to bind cynomolgus TREM-1. Humanisation of cynomolgus TREM-1 in the selected area did not result in regained affinity of 0177 compared to human TREM-1 (0247) indicating that other residues or combinations of residues are important for the differences in affinity for human and cynomolgus TREM-1.

0243 shows no binding to 0170 Fab or 0011 Fab. For this construct it cannot be excluded that mutations have affected the overall structure and therefore not be concluded if Q52 is involved in binding of the studied Fabs to human TREM-1.

TABLE 11

Affinity of 0170 Fab and 0011 Fab to wt cynomolgus TREM-1 ECD, partly humanised cynomolgus TREM-1 ECD variants and wt human TREM-1 ECD. Binding level of 0170 Fab and 0011 Fab 10 s after end of association, expressed as degree of theoretical maximum binding level.

| | KD (M) | | Normalised binding (% Rmax theor) | |
|---|---|---|---|---|
| Construct | 0170 Fab | 0011 Fab | 0170 Fab | 0011 Fab |
| wt cTREM-1 | 1E−09 | No binding | 39 | 0 |
| 0239 | 2E−09 | >1 uM | 19 | 1 |
| 0240 | 2E−09 | >1 uM | 28 | 0 |
| 0241 | 2E−09 | >1 uM | 26 | 2 |
| 0242 | 1E−09 | >1 uM | 21 | 1 |
| 0243 | No binding | No binding | 5 | 1 |
| 0244 | 1E−09 | No binding | 7 | 0 |
| 0245 | 1E−09 | No binding | 34 | 0 |
| 0247 | 2E−10 | 1E−09 | 45 | 42 |

Figure 9:
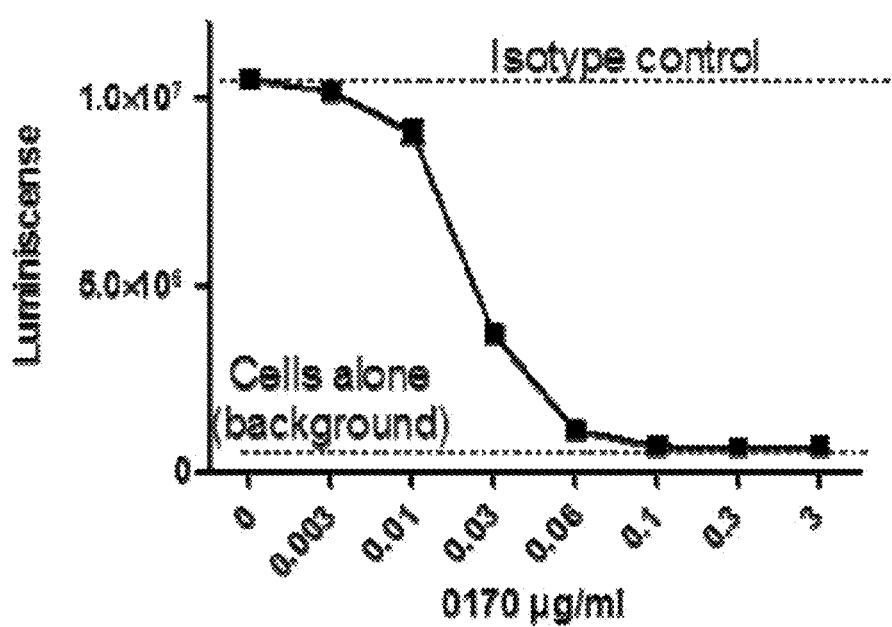
FIG. 9: The BWZ/hTREM-1 reporter cell co-cultured with TREM-1 ligand complex reflects the TREM-1 functionality which was dose-dependently inhibited by TREM-1 mAb-0170.

Example 14 mAb 0170 Efficiently Blocks TREM-1 Activation in the BWZ/hTREM-1 Reporter Cell Assay The BWZ/hTREM-1 reporter cell assay described in Example 6 was used to calculate the potency of mAb 0170 in blocking TREM-1. BWZ/hTREM-1 reporter cells were stimulated with TREM-1 ligand complex and mAb 0170 added at various concentrations. FIG. 9 shows a dose-dependent blocking of the TREM-1 signal resulting in total block of the signal at concentrations higher than 0.2 ug/ml. The IC50 value was determined to be 2.4 nM using the Graphpad Prism software, equation: log(inhibitor) vs. response—Variable slope.

Example 15

Commercially Available TREM-1 Antibodies do not Block TREM-1 Activation in the BWZ/hTREM-1 Reporter Cell Assay Multiple doses of antibody were included in the BWZ/hTREM-1 reporter cell assay, as described previously. SAB1405121 (clone 3F5 from Sigma Aldrich, St. Louis, Mo., USA), WH0054210M4 (clone 2E2 from Sigma Aldrich, St. Louis, Mo., USA), sc-80394 (clone 98Z12 from Santa Cruz, Calif., USA), HM2252 (clone 6B1 from Hycult biotech, 5405 PB UDEN, The Netherlands), 316102 (clone TREM-37 from Biolegend, San Diego, Calif. 92121, USA), and 314907 (clone TREM-26 from Biolegend, San Diego, Calif. 92121, USA), were not able to block the TREM-1 activity significantly, whereas mAb 0170 disclodes herein could block TREM-1 activity with more than 99% at 0.3 ug/ml. Isotype controls had >95% remaining reactivity even at 3 ug/ml.

TABLE 12

| Anti TREM-1 clone | % remaining activity at 0 μg/ml | % remaining activity at 0.003 μg/ml | % remaining activity at 0.03 μg/ml | % remaining activity at 0.3 μg/ml |
|---|---|---|---|---|
| SAB1405121 | 100 | 104 | 101 | 97 |
| WHO054210M4 | 100 | 98 | 104 | 86 |
| sc-80394 | 100 | 120 | 134 | 131 |
| HM2252 | 100 | 96 | 122 | 113 |
| 316102 (0.09% azide) | 100 | 98 | 103 | 90 |
| 314907 | 100 | 100 | 124 | 108 |
| mAb 0170 | 100 | 96 | 80 | 0 |

Example 16 mAb 0170 Blocked Cynomolgus TREM-1

In order to test for functionality against TREM-1 from other species, mouse and cynomolgus monkey TREM-1 was transfected together with human and mouse DAP12, respectively, to generate a reporter cell assay as the one for human. This was essentially done as described for the human system (Examples 1, 2 and 6) but replacing humanTREM-1 with full length murine (m)TREM-1 (SEQ ID NO: 22) or full length cynomolgus monkey (c)TREM-1 (SEQ ID NO: 21). cDNA encoding cTREM-1 (SEQ ID NO: 22) was synthesized at GeneArt and cloned into pHLEF38 (licensed from CMC ICOS), in the XhoI-XbaI orientation.TE alpha NFAT Luc cells was co-transfected with pHLEF38.cynoTrem1 and pNEF38.NFIag hDAP12 using 10 ug of each plasmid and electroporated 8e6 cells in approx. 500 ul total volume (400 ul growth medium and 100 ul DNA) using the BTX electoporator (260 V, 1050 uF, 720 ohms; time constant was 23 msec). Cells were plated for 48 hours in a 10 cm plate, in 10 ml of 50% conditioned medium and plated directly into selection at 8e3 cells/well of a flat bottomed 96W plates (5 plates) in 200 ul/well of 30% conditioned medium with 800 ug/ml G418 and 0.5 mM L-histidinol. After 2 weeks of incubation, 40 single colonies were identified using the Genetix Clone Select Imager.

The only commercially available TREM-1 antibody able to cross react with cynomolgus monkey TREM-1 was 314907 (clone TREM-26 from Biolegend, San Diego, Calif. 92121, USA) (see Example 11). None of the commercially available antibodies tested in Example 15 were able to block the function of cynoTREM-1, not even the one that could bind to cynomolgus monkey TREM-1.

TABLE 13

| % remaining cyno TREM-1 activity [mAb amount] | mAb 0170 | 314907 |
|---|---|---|
| 0 ug/ml | 100.00 | 100.00 |
| 0.74 ug/ml | 7.97 | 103.97 |
| 20 ug/ml | 0 | 87.72 |

Likewise, a reporter cell line with mouse TREM-1 was generated. None of the antibodies able to bind to human TREM-1 or to cynomolgus and human TREM-1 could cross-bind to mouseTREM-1. Thus, antibodies against mouse-TREM-1 were generated essentially as described for generating human TREM-1 antibodies but with mouse TREM-1 as the antigen. These antibodies were screened for mouse TREM-1 binding and blocking function in the murine reporter gene assay. One such antibody (mAb 0174) was able to bind and block the mouse TREM-1 function.

Example 17

TNFalpha Release from M2 Macrophages that were Stimulated by PGLYRP-1 was Blocked by TREM-1 Antibodies Those skilled in the art will recognize the value of establishing a freezer bank collection of primary cells from multiple donors thus providing for convenient replication of experiments. In vitro derived macrophages were produced from peripheral blood monocytes as follows. Negatively enriched monocytes were isolated from a peripheral blood "leukopak" obtained from Research Blood Components (Brighton, Mass., USA) using a Rosette Sep kit (cat. no. 15068) from Stem Cell Technologies (Vancouver, BC, Canada) following the manufacture instructions. Isolated monocytes were suspended in 10% DMSO/FBS aliquots of 50e6 cell/ml and gradually cooled to −80 C. To produce macrophage cells, one or more frozen vials of monocytes were rapidly thawed in a 37 C water bath, diluted to 10 ml with growth media [RPMI 1640 (Gibco, Carlsbad Calif., USA) cat. no. 72400-047) with 10% FBS (Fisher Scientific cat no 03-600-511] and centrifuged 5 minutes at 250 g. Cells were suspended to 2e6 cells/ml in growth media supplemented with 50 ng/ml human MCSF (Gibco cat. no. PHC9501), placed into tissue culture treated, petri style tissue culture plates and into a humidified incubator programmed to maintain a "hypoxic" atmosphere of 5% CO2, 2% O2. On the third day in culture, the cells were fed with the addition of an equal volume of growth media supplemented with 50 ng/ml human MCSF. After 6 days in culture the monocytes had differentiated into M0 macrophages. M0 cells were further differentiated by changing the media to growth media supplemented with 50 ng/ml human IFNg (Gibco cat no PHC4031) for M1 macrophages or 40 ng/ml human IL-4 (Gibco cat no PHC0045) for M2 macrophages and returning to the incubator for an additional 22 hours. On the seventh day, macrophages were suitably differentiated to be used in a bioassay. Briefly, macrophages were recovered from the petri plates by washing with 1×PBS, followed by 5 mM EDTA in PBS. The plates were then returned to 37 C for 30 minutes and cells were "power washed" off the plate using a 10 ml syringe and 22G needle. Cells were then diluted into growth media, centrifuged at 250 g for 5 minutes after which the cell pellet was suspended to a final concentration of 1e6/ml.

Figure 10:
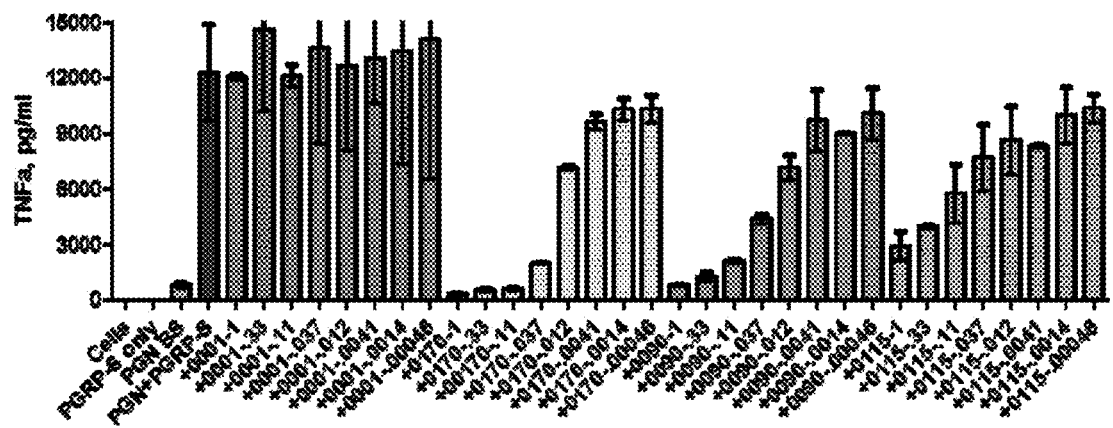
FIG. 10: TNFalpha release from M2 macrophages stimulated by PGLYRP-1 was blocked by TREM-1 antibodies.

Macrophage cells prepared as above were used in bioassays where cytokines such as TNF-alpha produced in response to stimulation of the cells with TREM-1 ligand were measured in the conditioned media by ELISA. Such a bioassay was further utilized to measure blockade of such TREM-1 ligand stimulation by TREM-1 specific antibodies. TREM ligand or negative controls were prepared at 4× concentrations and 50 microliters/well in growth media were added to 96 well microtiter dishes. Final concentrations of TREM-1 ligand consisted of 7.5 ng/ml recombinant human PGLYRP1 (see Example 5) and 3 μg/ml PGN-BS (Invivogen, tlrl-pgnbs, SanDiego Calif., USA). Cells were cultured under humidified hypoxic conditions as described above for 22 hours after which conditioned media was collected and TNF-alpha levels were measured by ELISA, following manufacturer's instructions (R&D Systems, catalogue DY210, MN, USA). FIG. 10 shows that the TREM-1 antibodies decrease TNFalpha release from these stimulated M2 macrophages.

Table 12, below, shows the IC50 values from such experiment indicating that the antibodies disclosed herein are very potent in blocking the TREM-1 dependent cytokine release.

TABLE 14

| Antibody (mAb) | R square | IC50, ng/ml |
|---|---|---|
| 0122 | 0.99 | 14 |
| 0170 | 0.99 | 12 |
| 0090 | 0.99 | 21 |
| 0115 | 0.88 | 92 |

Example 18

TNFalpha Release from Cynomolgus Macrophages can be Blocked by mAb 0170

Peripheral blood derived macrophage serve as an excellent invitro model in the study of innate immune modulation and activation. TREM-1 is known to play a key role in controlling this process. The use of the non-human primate species *Macaca fascicularis*, commonly known as Cynomolgus monkey is critical to understanding the in vivo effects of modulating TREM1 signalling. In this example anti-TREM-1 antibodies are tested for their ability to block production of cytokines in cynomolgus M2 macrophage cultures.

Macrophage cells were generated as follows. Whole blood was harvested from healthy male adult animals (SNBL, Everett Wash., USA) by venipuncture using sodium heparin vacutainer tubes (Cat No 3664870, Bectin Dickinson Franklin Lakes N.J., USA). Whole blood was diluted 30% with PBS, then 30 ml was carefully layered on to 15 ml of Ficoll-Paque (Cat No 17-1440-03 GE Healthcare, Uppsala Sweden) prediluted to 96% with PBS in a 50 ml conical tube. After centrifugation: 30 min, room temperature, 400 g with low acceleration and no brake; peripheral blood mononuclear cells (PBMC) were harvested from the Ficoll/plasma interphase, diluted 3× with PBS and centrifuged 7 minutes, room temperature, 200 g. Supernatant containing contaminating platelets was aspirated and discarded and the cell pellet was resuspended in 30 ml of PBS+0.2% FBS (fetal bovine serum). This cell wash process was repeated 2 additional cycles after which the PBMC cell pellet was resuspended in RPMI culture media (Cat No. 61870-036, Life Technologies, Grand Island N.Y., USA) plus 10% FBS to 2E6 cells/ml and dispensed onto 15 cm petri dishes (Cat No 430599 Corning, Tewksbury Mass., USA) at 20 ml/dish. Monocytes were allowed to adhere to plastic by incubating overnight at 37 C, 5% $CO_2$, 100% humidity after which non adherent cells were removed by gently swirling and rocking the plates for 20 seconds followed by aspiration. 20 ml of fresh growth media supplemented with 50 ng/ml hMCSF (Cat No. PHC9501, Life Technologies, Grand Island N.Y., USA) was added to each plate and placed into hypoxic culture conditions of 37 C, 5% $CO_2$, 2% $O_2$, 100% humidity for 7 days. On the third day in culture, the cells were fed with the addition of an equal volume of growth media supplemented with 50 ng/ml human MCSF. After 6 days in culture the monocytes had differentiated into M0 macrophages. M0 cells were further differentiated by changing the media to growth media supplemented with 50 ng/ml human IFNg (Gibco cat no PHC4031) for M1 macrophages or 40 ng/ml human IL-4 (Cat No. PHC0045, Life Technologies, Grand Island N.Y., USA) for M2 macrophages and returning to the incubator for an additional 22 hours. On the seventh day, macrophages were suitably differentiated to be used in a bioassay. Briefly, macrophages were recovered from the petri plates by washing with 1×PBS, followed by 5 mM EDTA in PBS. The plates were then returned to 37 C for 30 minutes and cells were "power washed" off the plate using a 10 ml syringe and 22G needle. Cells were then diluted into growth media, centrifuged at 250 g for 5 minutes after which the cell pellet was suspended to a final concentration of 1e6/ml.

Macrophage cells prepared as above were used in bioassays where cytokines such as TNF-alpha produced in response to stimulation of the cells with TREM-1 ligand were measured in the conditioned media by ELISA. Such a bioassay was further utilized to measure blockade of such TREM-1 ligand stimulation by TREM-1 specific antibodies. TREM-1 ligand or negative controls were prepared at 4× concentrations and 50 microliters/well in growth media were added to 96 well microtiter dishes. Final concentrations of TREM-1 ligand consisted of 7.5 ng/ml recombinant human PGLYRP1 (generated as described in Example 5) and 3 µg/ml PGN-BS (Cat No. tlrl-pgnbs, Invivogen SanDiego Calif., USA). Antibodies were added in 50 microliters/well of growth media followed by cells in 50 microliters/well of macrophage. Cells were cultured under humidified hypoxic conditions as described above for 22 hours after which conditioned media was collected and TNF-alpha levels were measured by ELISA, following manufacturer's instructions (Cat No. DY1070 R&D Systems, Minneapolis Minn., USA). The table following table shows TNFα values of M2 macrophage cultures stimulated with TREM-1 ligand (PGLYRP1+PGN) in the presence of control antibody or anti-TREM-1 antibody.

| M2 macrophages with: | Donor 1 TNF-α, pg/ml | | Donor 2 TNF-α, pg/ml | |
|---|---|---|---|---|
| | Avg | SD | Avg | SD |
| Cells only | 0.5 | | 19.0 | 12.0 |
| PGRP-S only | 3.5 | | 13.0 | 6.3 |
| PGN BS only | 5.7 | 2.8 | 22.4 | 3.8 |
| PGN + PGRP-S | 295.3 | 49.3 | 307.4 | 75.8 |
| +Fc4 neg -3 | 248.5 | 54.0 | 285.0 | 57.6 |
| +Fc4 neg -1 | 215.6 | 41.5 | 295.0 | 59.0 |
| +Fc4 neg -.33 | 217.5 | 49.7 | 357.7 | 118.6 |
| +Fc4 neg -.11 | 193.9 | 40.4 | 348.4 | 75.7 |
| +Fc4 neg -.037 | 172.6 | 57.6 | 370.7 | 88.6 |
| +Fc4 neg -.012 | 177.6 | 38.1 | 286.7 | 71.5 |
| +Fc4 neg -.0041 | 275.4 | 67.9 | 253.3 | 45.0 |
| +0170-3 | 33.3 | 8.8 | 57.2 | 3.2 |
| +0170-1 | 41.3 | 8.5 | 47.0 | 10.5 |
| +0170-.33 | 45.3 | 14.3 | 80.4 | 21.6 |
| +00170-.11 | 42.2 | 12.4 | 103.8 | 32.8 |
| +0170-.037 | 54.4 | 18.5 | 142.3 | 43.5 |
| +0170-.012 | 86.2 | 24.4 | 203.8 | 55.6 |
| +0170-.0041 | 186.7 | 21.0 | 249.3 | 92.5 |
| +0170-.0014 | 231.2 | 56.0 | 286.1 | 112.8 |
| +0170-.00046 | 246.4 | 22.7 | 254.2 | 70.5 |

This example illustrates that the anti TREM-1 Ab-0170 can effectively block TREM dependent cytokine production in macrophage cells derived from cynomolgus monkeys. The efficacy of this Ab supports its use in cynomolgus monkey in in vivo toxicology and disease treatment models.

Example 19

TNFalpha Release from Stimulated Peripheral Blood Mononuclear Cells can be Blocked by TREM-1 Antibodies PBMC's, from a buffy coat and frozen in RPMI 1640 (Cat. no. 61870, Gibco, N.Y., USA), 20% FBS (Cat #16140-071, Gibco, N.Y., USA, 10% DMSO (Cat# D2650, Sigma, Steinheim, Germany), were thawed and washed twice in RPMI, 10% FBS, 1% Pen/Strep (Cat. no. 15070-06, Gibco, N.Y., USA), and resuspended in same medium to 4×10E6/ml. Cells were then distributed with 400.000 cells/well. 10 µg/ml PGN-SA (Cat # tlrl-pgnsa, Invivogen, San Diego, USA) and 0.2 µg/ml PGLYRP1 were added to the wells for stimulating the cells. Subsequently, the relevant isotype and TREM-1 antibodies were diluted in RPMI and added at 1.34 nM, and 0.167 nM respectively. TNFalpha release were measured by diaplex (Cat #880.090.001, Genprobe, Besancon, France) according to manufacturers protocol after 20 hrs incubation at 37° C., 5% $CO_2$. As shown in Table 13, below, the TREM-1 antibodies disclosed herein (mAbs 0044, 0070 and 0059) are all able to decrease the TNFalpha release from PBMC cells.

TABLE 15

| % Inhibition compared to isotype | Isotype at 1.34 nM | 0 nM | 0.167 nM |
|---|---|---|---|
| a-Trem-1 0044 (mIgG2a) | 100 | 100 | 68 |
| a-Trem-1 0070 ((hIgG4) | 100 | 117 | 76 |
| a-Trem-1 0059 (hzIgG1.1) | 100 | 105 | 61 |

The approximately 70% inhibition of TNFalpha release in PBMCs using a blocking TREM-1 antibody indicates a significant impact on cytokine levels in a stimulated cell culture.

Example 20

Anti-TREM-1 mAb can Inhibit PGN+PGLYRP1-Induced TNFa Production in Normoxic Macrophages Stimulation of macrophages using PGN-BS+human PGLYRP1 as a stimulant of the TREM-1 receptor can be blocked by anti-TREM-1 antibodies.

Monocytes were differentiated into M2 macrophages as in Example 15. All steps of the differentiation and stimulation of the cells were done in a 37° C., 5% CO2 incubator under normal atmospheric oxygen levels (normoxia). The differentiated M2 macrophages were resuspended in RPMI/10% FBS and plated out at 5×10E5 cells/ml in triplicate (unless otherwise noted) test wells. The cells were then stimulated for 24 hours with the following stimulations: no addition, PGLYRP1, PGN-BS (InVivogen, tlrl-pgnbs) (two sets of triplicates), PGN-BS+PGLYRP1 (three sets of triplicates), or PGN-BS+PGLYRP1 in the presence of anti-TREM-1 or isotype control antibody. Supernatants were then harvested and analysed for TNFa using BioPlex (Bio-Rad, 171-B5026M). Antibodies (0.1 µg/ml) mAb-0122 and -0170 directed against TREM-1 were able to lower the TNF-alpha release.

TABLE 16

| Macrophages stimulated with: | Donor 1 TNFa pg/ml | | Donor 2 TNFa pg/ml | |
|---|---|---|---|---|
| | Avg | SD | Avg | SD |
| No addition | 0 | 0 | 0 | 0 |
| PGLYRP1 | 0 | 0 | 0 | 0 |
| PGN-BS | 427 | 86 | 381 | 85 |
| PGN-BS + PGLYRP1 | 728 | 293 | 771 | 220 |
| PGN-BS + PGLYRP1 + hIgG4 isotype control | 987 | 183 | 884 | 41 |
| PGN-BS + PGLYRP1 + mAb 0122 | 243 | 14 | 367 | 16 |
| PGN-BS + PGLYRP1 + mAb 0170 | 122 | 106 | 224 | 54 |

This example illustrates that anti-TREM-1 mAb-0122 and -0170 can inhibit TNFa production from macrophages grown under normoxic conditions.

Example 21

TREM-1 Antibody Specifically Inhibits Rheumatoid Arthritis Synovial Fluid-Induced Response The RA synovial fluid samples from patients suffering from rheumatoid arthritis were assayed for TREM-1 ligand activity in the BWZ reporter assay as described in Example 6. Briefly, synovial fluid was thawed, vortexed, and serially diluted, assayed in duplicate+/−10 µg/ml PGNECndi (Invivogen, SanDiego, Calif., USA) with the addition of TREM-1 antibodies or a negative isotype control. The synovial fluid from a rheumatoid arthritis patient is able to trigger the BWZ/hTREM-1 reporter cell assay in a TREM-1 dependent manner which is further enhanced by adding MAB1278 (R&D Systems, Minneapolis, Minn. 55413, USA: Cat. no. MAB1278)) whereas the blocking TREM-1 antibodies disclosed herein are able to decrease this activation.

The antibodies were tested in two assays indicated by the two columns below, each antibody in concentrations ranging from 0.1 to 10 ug/ml. MAB1278 clearly enhanced the signal, whereas mAbs 0122 and 0170 decreased the signal compared to the isotype control.

TABLE 17

| Concentration | +mAb 0122 | | +mAb 0170 | | +mAb 1278 | | +IgG4 isotype control | |
|---|---|---|---|---|---|---|---|---|
| 10 ug/ml | 80877 | 79731 | 52064 | 50304 | 1079000 | 1054000 | 306906 | 397556 |
| 1 ug/ml | 74191 | 66458 | 48254 | 46978 | 1192000 | 1023000 | 398431 | 363267 |
| 0.1 ug/ml | 133900 | 163521 | 246695 | 169483 | 828866 | 691379 | 293831 | 313445 |

Example 22

Cytokine Release from Synovial Tissue Cells from Rheumatoid Arthritis Patients Upon Stimulation with PGLYRP-1 can be Blocked by mAb 0170

Synovial tissue samples were obtained from RA patients during total knee replacement. Single suspension of synovial tissue cells was isolated by a digestion via 4 mg/ml of collagenase (cat#11088793001, Roche, Mannheim, Germany) and 0.1 mg/ml of DNase (cat#11284932001, Roche, Mannheim, Germany) for 1 h at 37 degrees C.

Synovial tissue cells at 1×10^5/well in culture medium RPMI (cat#R0883, St Louis, Mo., USA)+10% FCS (cat#50115, BioChrom AG, Grand Island, N.Y. 14072, USA) were stimulated with 4 ug/ml of PGLYRP1 and 1 ug/ml of PGN-ECNDi (cat# tlrl-kipgn, Invivogen, San Diego, Calif. 92121, USA) under hypoxic condition in the presence or absence of various concentrations of mAb 0170 or an isotype hIgG4 control. After 24 h incubation, cell supernatants were harvested, and cytokines were measured by either ELISA (TNFa (cat# DY210, R&D, Minneapolis, Minn. 55413 USA), IL-1b (88-7010-88, eBioscience, San Diego, Calif. 92121, USA), GM-CSF (cat#88-7339-88, eBioscience)) or Flowcytomix (TNFa, IL-1b, MIP-1b, MCP-1, IL-6, and IL-8 (cat#BMS, eBioscience). The cytokines were secreted from the synovial tissue cells upon stimulation with the TREM-1 ligand and specifically blocked by TREM-1 antibody mAb 0170.

Below is an example of such experiment, where either 4 ng/ml or 10 ng/ml mAb was used resulting in a decrease of cytokine release when treated with TREM-1 antibody mAb 0170.

TABLE 18

| Cytokine (pg/ml) | PGN | PGN + PGLYRP1 | PGN + PGLYRP1 + 10 ng/ml control | PGN + PGLYRP1 + 10 ng/ml mAb 0170 |
|---|---|---|---|---|
| TNFalpha | 624 | 1445 | 1034 | 429 |
| MIP-1beta | 2458 | 4395 | 3791 | 2321 |
| MCP-1 | 273 | 471 | 391 | 210 |

TABLE 19

| Cytokine (pg/ml) | PGN | PGN + PGLYRP1 | PGN + PGLYRP1 + 4 ng/ml control | PGN + PGLYRP1 + 4 ng/ml 0170 |
|---|---|---|---|---|
| IL-1beta | 2419 | 3773 | 3477 | 2308 |
| GM-CSF | 182 | 616 | 656 | 431 |
| IL-6 | 2057 | 4189 | 3475 | 1632 |
| IL-8 | 2575 | 5509 | 4499 | 2112 |

This example shows that cells from synovial tissue from rheumatoid arthritis patients will respond to stimulation by the TREM-1 ligand, PGLYRP1, by secreting numerous cytokines which can be inhibited by mAb 0170.

Example 23

Type II PGLYRP1 Induced TNFalpha Release in Synovial Tissue Cells from Rheumatoid Arthritis Patients can be Blocked by TREM-1 Antibody mAb 0170

Synovial tissue samples were obtained from RA patients during total knee replacement. Single suspension of synovial tissue cells was isolated by a digestion via 4 mg/ml of collagenase (cat. no. 11088793001, Roche, Mannheim, Germany) and 0.1 mg/ml of DNase (cat. no. 11284932001, Roche, Mannheim, Germany) for 1 h at 37 degree. The synovial tissue cells ($1 \times 10^5$/well in culture medium RPMI (cat. no. 22400105, Gibco, N.Y. 14072, USA)+10% FCS (cat. no. 50115, BioChrom AG, Berlin, Germany)) were co-cultured with various doses of HEK cells transiently transfected with type II PGLYRP1 under hypoxic condition in the presence or absence of 1 ug/ml of mAb 0170 or IgG4 isotype control. After 24 h incubation, cell supernatants were harvested, and cytokines were measured by TNFa ELISA (cat. no. DY210, R&D, Minneapolis, Minn. 55413 USA).

TABLE 20

| Type II PGLYRP1 (HEK transfected)/ Control HEK | TNF-a (pg/ml) release | | | | | |
|---|---|---|---|---|---|---|
| | $1 \times 10^{-5}$ | $3 \times 10^{-4}$ | $1 \times 10^{-4}$ | $3 \times 10^{-3}$ | $1 \times 10^{-3}$ | 0 |
| IgG4 + Type II cells | 121.17 | 114.08 | 95.02 | 54.56 | 57.87 | 33.47 |
| IgG4 + Control cells | 55.65 | 63.73 | 57.99 | 33.78 | 36.40 | 36.32 |
| mAb 0170 + Type II cells | 44.05 | 44.67 | 44.40 | 39.45 | 44.29 | 31.40 |
| mAb 0170 + Control cells | 54.50 | 57.06 | 53.10 | 42.10 | 31.99 | 27.82 |

This example shows that the TREM-1 ligand (type II cells) induced TNF-alpha release in a dose-dependent manner in synovial tissue cells from rheumatoid arthritis patients compared to control cells (mock transfected). This TNFalpha response was blocked by mAb 0170 but not with isotype IgG4. The control cells were not affected.

Example 24

Platebound MAB1278 Induced IL-6 and TNFalpha Response in Macrophages, Showing Agonistic Features, Whereas mAbs 0122 and 0170 Did not Stimulation of macrophages on platebound agonistic anti-TREM-1 antibodies induced production of IL-6 and TNFa. Monocytes were purified from healthy donor buffy coats using RosetteSep (StemCell Technologies, 15068) and differentiated into macrophages by culturing for 6 days in RPMI/10% FBS in the presence of 40 ng/ml human MCSF. The macrophages were then further differentiated to M2 macrophages by changing the media to growth media supplemented with 50 ng/ml human IL-4 and returning to the incubator for an additional 24 hours. On the seventh day, macrophages were recovered from the culture plates by washing with 1×PBS, followed by 5 mM EDTA in PBS. The plates were then returned to 37° C. for 30 minutes before the macrophages were washed off the plates. The macrophages were washed in RPMI/10% FBS before resuspending and plating out. The test wells had been pre-coated with the specified antibodies by incubating them overnight with antibody diluted in PBS, followed by washing ×3 in PBS. The resuspended macrophages were plated out at 5×10E5 cells/ml in triplicate test wells followed by incubation for 24 hours. (All steps of the differentiation and stimulation of the cells were done in a 37° C., 5% CO2 incubator under normal atmospheric oxygen levels (normoxia)). Supernatants were then harvested and analysed for IL-6 and TNFa using BioPlex (Bio-Rad, 171-B5006M and 171-B5026M).

Antibodies mAb-0122 and -0170 showed very low agonism whereas the MAB1278 antibody (RnD Systems, MAB1278) showed potent induction of both IL-6 and TNFa.

TABLE 21

| Platebound mAb stimulation: | IL-6 pg/ml | | TNFa pg/ml | |
|---|---|---|---|---|
| | Avg | SD | Avg | SD |
| No antibody | 1 | 3 | 0.3 | 0.8 |
| mIgG1 isotype cntr 2 µg/ml | 0 | 0 | 0 | 0 |
| mIgG1 isotype cntr 6 µg/ml | 0 | 0 | 0 | 0 |
| mIgG1 isotype cntr 20 µg/ml | 14 | 24 | 5 | 5 |
| MAB1278 2 µg/ml | 412 | 71 | 2004 | 451 |
| MAB1278 6 µg/ml | 877 | 38 | 6454 | 278 |
| MAB1278 20 µg/ml | 1352 | 76 | 7753 | 555 |
| hIgG4 isotype cntr 2 µg/ml | 5 | 5 | 2 | 1 |
| hIgG4 isotype cntr 6 µg/ml | 18 | 15 | 9 | 9 |
| hIgG4 isotype cntr 20 µg/ml | 37 | 3 | 34 | 1 |
| mAb 0122 2 µg/ml | 93 | 48 | 59 | 18 |
| mAb 0122 6 µg/ml | 126 | 8 | 105 | 17 |
| mAb 0122 20 µg/ml | 234 | 10 | 304 | 26 |
| mAb 0170 2 µg/ml | 137 | 29 | 76 | 21 |
| mAb 0170 6 µg/ml | 181 | 12 | 187 | 28 |
| mAb 0170 20 µug/ml | 277 | 15 | 629 | 108 |

This example illustrates that mAb-0122 and -0170 only show very low agonistic activity in macrophages and indicates true blocking features of these mAbs.

Example 25

Blocking TREM-1 in a Mouse Arthritis Model Reduces Disease

The experiments outlined in Table 22 were obtained in the DTH-arthritis model, which is a single paw arthritis model. Single paw arthritis was induced in female C57BL/6 mice by eliciting a classical delayed-type hypersensitivity (DTH) reaction in the right hind paw by immunisation and subsequent challenge with methylated bovine serum albumin (mBSA), with the modification that a cocktail of type II collagen monoclonal antibodies (anti-CII) was administered IV between the immunisation and challenge steps. The left hind paw received PBS challenge and functioned as an intra-animal control. Mice (10 mice/group) were treated 3 times/week with a TREM monoclonal antibody that specifically binds and blocks murine TREM-1, as determined using a murine version of the reporter assay described in Example 6. The first dose was administered on the day of immunization. Mice (9-10 mice/group) were treated with either a control antibody or PBS as a control. Paw swelling was measured from the day of arthritis induction and 11 days onwards. Results are presented as a mean area under the curve (AUC) ±SEM. Statistical significance was tested by using a two sided unpaired t-test, 95% confidence interval.

TABLE 22

Effect of TREM-1 treatment on paw swelling (AUC-mm) in a mouse arthritis model.

| Effect measure | Experiment | TREM-1 mAb§ | Control mAb§ | PBS |
|---|---|---|---|---|
| AUC-mm paw swelling | #1 | 8.03 +/− 1.01** | 12.26 +/− 0.84 | 12.53 +/− 0.87 |
| AUC-mm paw swelling | #2 | 8.45 +/− 0.94** | 11.71 +/− 0.22 | 12.89 +/− 0.36 |

Means +/− SEM.
§mice treated with 5 mg/kg, 3 times/week for 3 weeks
**P ≤ 0.005, two sided unpaired t-test, 95% confidence interval vs. control mAb and vs. PBS Example 26

Activated Neutrophils Release IL-8 which can be Blocked by TREM-1 mAbs

Neutrophils express TREM-1 and neutrophils also express the TREM-1 ligand. To test whether TREM-1 is involved in an autocrine stimulation loop in neutrophils, isolated neutrophils were stimulated with PGN-SA (InVivogen, tlrl-pgnsa), and the release of IL-8 into the culture medium was measured. TREM-1 antibodies mAb-0059, -0067, -0122, and -0170 were able to decrease the PGN-SA-induced IL-8 release. Neutrophils were isolated from human healthy donor whole blood and resuspended in RPMI/10% FBS at 1.5× 10E6 cells/ml, and plated out into triplicate test wells pre-coated with Fibrinogen (pre-coated with 50 l of 1 mg/ml Fibrinogen (Sigma, F3879) in PBS for 2 hours at 37° C., followed by washing ×3 in PBS). The cells were tested under the following conditions: no added stimulation, 10 g/ml PGN-SA only, or 10 g/ml PGN-SA in the presence of mAb-0059, -0067, -0122, -0170 or isotype control antibody at 0.25 g/ml. The samples were cultured 24 hours in a 37° C., 5% $CO_2$ incubator. Supernatants were then harvested and analysed for IL-8 using the Bio-plex Pro Human Cytokine IL-8 set (Bio-Rad, 171-B5008M).

TABLE 23

| | IL-8, pg/ml | |
|---|---|---|
| Neutrophils stimulated with: | Avg | SD |
| Experiment 1 | | |
| No addition | N.D. | N.D. |
| PGN-SA | 562 | 54 |
| PGN-SA + hIgG1.1 isotype contr. | 461 | 80 |
| PGN-SA + mAb 0059 | 165 | 55 |
| PGN-SA + mAb 0067 | 183 | 77 |
| Experiment 2 | | |
| No addition | 857 | 214 |
| PGN-SA | 6116 | 191 |
| PGN-SA + hIgG4 isotype contr. | 6530 | 1962 |
| PGN-SA + mAb 0122 | 2466 | 437 |
| PGN-SA + mAb 0170 | 2171 | 480 |

This example illustrates that IL-8 release from neutrophils induced by stimulation with the bacterially derived PGN can be reduced by TREM-1 antibodies. Thus demonstrating that TREM-1 is involved in an autrocrine activation loop in neutrophils, and the TREM-1 antibodies are potentially useful in downregulating neutrophil responses.

Example 27

Activated Neutrophils can Stimulate Monocytes, which can be Blocked by Anti-TREM-1 mAbs Activated neutrophils express the TREM-1 ligand. To test if activated neutrophils can stimulate other immune cells in a TREM-1-dependent manner, activated neutrophils were used to stimulate isolated monocytes and the release of TNFa into the culture medium was measured. TREM-1 antibodies mAb-0059 and -0170 were able to decrease the neutrophil-induced TNFa release from the monocytes.

Neutrophils were isolated from human healthy donor whole blood and resuspended in RPMI/10% FBS, and plated at 1.5×10E5 cells/well in poly-D-Lysine coated tissue culture 96-well plates (Corning, 3841). The neutrophils were then stimulated with 1 ng/ml PMA (Sigma, P1585)+20 g/ml PGN-SA (InVivogen, tlrl-pgnsa) for 24 hours in a 37° C., 5% CO2 incubator. The cells were then washed gently ×3 with media before adding in freshly isolated monocytes. The monocytes were purified from healthy donor buffy coats using an Easy-Sep kit (Stem cell technologies, 19059), and were plated out with 5×10E4 cells/well in the wells already containing activated, washed neutrophils. The following antibodies were added at 1 g/ml: mAb-0059, mAb-0170, or hIgG4 isotype control. The cells were then cultured for another 24 hours before harvesting the supernatant. The supernatant was diluted 1:10 in RPMI/10% FNS before measuring TNFa by ELISA (eBioscience, BMS223INST).

TABLE 24

| | TNFa pg/ml | |
|---|---|---|
| Monocytes stimulated with: | Avg | SD |
| No neutrophils | 34 | 85 |
| Activated neutrophils | 299 | 67 |
| Activated neutrophils + isotype control | 232 | 32 |
| Activated neutrophils + mAb 0059 | 72 | 14 |
| Activated neutrophils + mAb 0170 | 129 | 9 |

This example illustrated that activated neutrophils can stimulate monocytes in a TREM-1-dependent manner to produce TNFa, and this can be blocked by mAb-0059 and mAb-0170 anti-TREM-1 antibodies. Anti-TREM-1 antibodies are therefore potentially useful for downregulating monocyte responses.

While certain features of the invention have been illustrated and described herein, many modifications, substitutions, changes, and equivalents will now be apparent to those of ordinary skill in the art. It is, therefore, to be understood that the appended claims are intended to cover all such modifications and changes as fall within the true spirit of the invention.

The invention claimed is:

1. An isolated antibody or fragment thereof, wherein the antibody or fragment thereof competes with mAb 0170 for binding to and blocking a triggering receptor expressed on myeloid cells-1 (TREM-1) having an amino acid sequence set for as SEQ ID NO:1 (human TREM-1), SEQ ID NO:12 or SEQ ID NO:21 (cynomolgus monkey TREM-1).

2. The antibody or fragment thereof according to claim 1, which is capable of blocking peptidoglycan recognition protein 1 (PGLYRP1)-induced activation of TREM-1.

3. The antibody or fragment thereof according to claim 1, which is capable of specifically binding a polypeptide comprising amino acids D38 to F48 of SEQ ID NO:1 (human TREM-1).

4. The antibody or fragment thereof according to claim 1, which is capable of specifically binding a polypeptide comprising amino acid residues E19 to L26 of SEQ ID NO: 12 (cynomolgus monkey TREM-1).

5. The antibody or fragment thereof according to claim 1, which has an epitope comprising one, two, three, four, five, six, seven or all of the amino acid residues D38, V39, K40, C41, D42, Y43, T44 and L45 and one, two or all of the amino acid residues E46, K47, F48 of SEQ ID NO: 1 (human TREM-1).

6. The antibody or fragment thereof according to claim 5, which has an epitope further comprising one, two or all of the amino acid residues L31, I86 and V101 of SEQ ID NO: 1 (human TREM-1).

7. The antibody or fragment thereof according to claim 1, which has an epitope comprising one, two, three or all of the amino acid residues D42, E46, D92 and H93 of SEQ ID NO: 1 (human TREM-1).

8. The antibody or fragment thereof according to claim 7, which has an epitope further comprising one, two or all of the amino acid residues L31, I86 and V101 of SEQ ID NO: 1 (human TREM-1).

9. The antibody according to claim 1, which is capable of specifically binding SEQ ID NO: 13 (K20A-hTREM-1-Cmyc2-His6).

10. The antibody according to claim 1, which is capable of specifically binding SEQ ID NO: 14 (A24T/Y28F/N30S/R32Q/P70H-cTREM-1-Cmyc2-His6).

11. The antibody according to claim 1, which is capable of specifically binding SEQ ID NO: 15 (A24T/Y28F/N30S/R32Q/E54K-cTREM-1-Cmyc2-His6).

12. The antibody according to claim 1, wherein mAb 0170 further comprises a heavy chain having an amino acid sequence set forth as SEQ ID NO:4 and a light chain having an amino acid sequence set forth as SEQ ID NO:5; wherein the heavy chain comprises a CDRH1 sequence corresponding to amino acid residues 31 to 35 of SEQ ID NO:4, and/or a CDRH2 sequence corresponding to amino acids 50 to 68 of SEQ ID NO:4, and/or a CDRH3 sequence corresponding to amino acid residues 101 to 110 of SEQ ID NO:4; and wherein the light chain comprises a CDRL1 sequence corresponding to amino acid residues 24 to 38 of SEQ ID NO:5, and/or a CDRL2 sequence corresponding to amino acid residues 54 to 60 of SEQ ID NO:5, and/or a CDRL3 sequence corresponding to amino acid residues 93 to 101 of SEQ ID NO:5.

13. The antibody of claim 12, wherein the CDRH1, CDRH2, CDRH3 sequences may be modified by substituting one, two or three of the amino acid residues.

14. The antibody of claim 12, wherein the CDRL1, CDRL2, and CDRL3 sequences may be modified by substituting one, two or three of the amino acid residues.

* * * * *

SEQUENCE LISTING

<160> NUMBER OF SEQ ID NOS: 23

<210> SEQ ID NO 1
<211> LENGTH: 234
<212> TYPE: PRT
<213> ORGANISM: Homo Sapiens

<400> SEQUENCE: 1

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230

<210> SEQ ID NO 2
<211> LENGTH: 121
<212> TYPE: PRT
<213> ORGANISM: Mus musculus

<400> SEQUENCE: 2

Glu Val Gln Leu Glu Glu Ser Gly Gly Gly Leu Val Gln Pro Lys Gly
1               5                   10                  15

Ser Leu Lys Leu Ser Cys Gly Ala Ser Asp Phe Thr Phe Asn Thr Tyr
            20                  25                  30

Ala Met His Trp Val Arg Gln Ala Pro Gly Met Ala Leu Glu Trp Val
        35                  40                  45

Ala Arg Ile Arg Thr Lys Ser Ser Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Met Tyr

```
                        85                  90                  95
Tyr Cys Val Arg Asp Met Gly Gln Arg Arg Gln Phe Ala Tyr Trp Gly
                100                 105                 110

Gln Gly Thr Leu Val Thr Val Ser Ala
            115                 120

<210> SEQ ID NO 3
<211> LENGTH: 112
<212> TYPE: PRT
<213> ORGANISM: Mus musculus

<400> SEQUENCE: 3

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Val Ala Thr Tyr Tyr Cys Gln Gln Ser Asn
                85                  90                  95

Glu Asp Pro Tyr Thr Phe Gly Gly Gly Thr Lys Leu Glu Ile Glu Arg
                100                 105                 110

<210> SEQ ID NO 4
<211> LENGTH: 448
<212> TYPE: PRT
<213> ORGANISM: Artificial Sequence
<220> FEATURE:
<223> OTHER INFORMATION: heavy chain of a humanised TREM-1 antibody
<220> FEATURE:
<221> NAME/KEY: CHAIN
<222> LOCATION: (1)..(448)
<223> OTHER INFORMATION: heavy chain of a humanised TREM-1 antibody

<400> SEQUENCE: 4

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Asn Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
                100                 105                 110

Gln Gly Thr Leu Val Thr Val Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
```

-continued

```
              145                 150                 155                 160

Ser Trp Asn Ser Gly Ala Leu Thr Ser Gly Val His Thr Phe Pro Ala
                        165                 170                 175

Val Leu Gln Ser Ser Gly Leu Tyr Ser Leu Ser Ser Val Val Thr Val
                        180                 185                 190

Pro Ser Ser Ser Leu Gly Thr Lys Thr Tyr Thr Cys Asn Val Asp His
                        195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
        225                 230                 235                 240

Val Phe Leu Phe Pro Pro Lys Pro Lys Asp Thr Leu Met Ile Ser Arg
                        245                 250                 255

Thr Pro Glu Val Thr Cys Val Val Val Asp Val Ser Gln Glu Asp Pro
                        260                 265                 270

Glu Val Gln Phe Asn Trp Tyr Val Asp Gly Val Glu Val His Asn Ala
                        275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
        305                 310                 315                 320

Lys Cys Lys Val Ser Asn Lys Gly Leu Pro Ser Ser Ile Glu Lys Thr
                        325                 330                 335

Ile Ser Lys Ala Lys Gly Gln Pro Arg Glu Pro Gln Val Tyr Thr Leu
                        340                 345                 350

Pro Pro Ser Gln Glu Glu Met Thr Lys Asn Gln Val Ser Leu Thr Cys
                        355                 360                 365

Leu Val Lys Gly Phe Tyr Pro Ser Asp Ile Ala Val Glu Trp Glu Ser
                        370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Arg Leu Thr Val Asp Lys Ser
                        405                 410                 415

Arg Trp Gln Glu Gly Asn Val Phe Ser Cys Ser Val Met His Glu Ala
                        420                 425                 430

Leu His Asn His Tyr Thr Gln Lys Ser Leu Ser Leu Ser Leu Gly Lys
                        435                 440                 445

<210> SEQ ID NO 5
<211> LENGTH: 218
<212> TYPE: PRT
<213> ORGANISM: Artificial Sequence
<220> FEATURE:
<223> OTHER INFORMATION: light chain of a humanised TREM-1 antibody
<220> FEATURE:
<221> NAME/KEY: CHAIN
<222> LOCATION: (1)..(218)
<223> OTHER INFORMATION: light chain of a humanised TREM-1 antibody

<400> SEQUENCE: 5

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Phe
                20                  25                  30

Asp Tyr Ser Phe Leu His Trp Tyr Gln Gln Lys Pro Gly Gln Pro Pro
            35                  40                  45
```

```
Lys Leu Leu Ile Tyr Arg Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 6
<211> LENGTH: 448
<212> TYPE: PRT
<213> ORGANISM: Artificial Sequence
<220> FEATURE:
<223> OTHER INFORMATION: heavy chain of a humanised TREM-1 antibody
<220> FEATURE:
<221> NAME/KEY: CHAIN
<222> LOCATION: (1)..(448)
<223> OTHER INFORMATION: heavy chain of a humanised TREM-1 antibody

<400> SEQUENCE: 6

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Thr Tyr
             20                  25                  30

Ala Met His Trp Val Arg Gln Ala Ser Gly Lys Gly Leu Glu Trp Val
         35                  40                  45

Gly Arg Ile Arg Thr Lys Ser Ser Asn Tyr Ala Thr Tyr Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg Asp Met Gly Gln Arg Arg Gln Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

Val Leu Gln Ser Ser Gly Leu Tyr Ser Leu Ser Ser Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 7
<211> LENGTH: 218
<212> TYPE: PRT
<213> ORGANISM: Artificial Sequence
<220> FEATURE:
<223> OTHER INFORMATION: light chain of a humanised TREM-1 antibody
<220> FEATURE:
<221> NAME/KEY: CHAIN
<222> LOCATION: (1)..(218)
<223> OTHER INFORMATION: light chain of a humanised TREM-1 antibody

<400> SEQUENCE: 7

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser

```
                65                  70                  75                  80
Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 8
<211> LENGTH: 121
<212> TYPE: PRT
<213> ORGANISM: Mus musculus

<400> SEQUENCE: 8

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Thr Lys Ser Asn Asn Tyr Ala Thr Tyr Tyr Val Asp
    50                  55                  60

Ser Val Lys Asp Arg Ile Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Asp Met Gly Ile Arg Arg Gln Phe Ala Tyr Trp Gly
            100                 105                 110

Gln Gly Thr Leu Val Thr Val Ser Ala
        115                 120

<210> SEQ ID NO 9
<211> LENGTH: 112
<212> TYPE: PRT
<213> ORGANISM: Mus musculus

<400> SEQUENCE: 9

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Phe
            20                  25                  30

Gly Ile Ser Phe Met His Trp Tyr Gln Gln Ser Pro Gly Gln Pro Pro
        35                  40                  45

Lys Leu Leu Ile Tyr Arg Ala Ser Asn Leu Glu Ser Gly Ile Pro Ala
```

```
                    50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                     85                  90                  95

Glu Asp Pro Tyr Thr Phe Gly Gly Gly Thr Lys Leu Glu Ile Lys Arg
                100                 105                 110

<210> SEQ ID NO 10
<211> LENGTH: 121
<212> TYPE: PRT
<213> ORGANISM: Mus musculus

<400> SEQUENCE: 10

Glu Val Gln Leu Val Glu Ser Gly Gly Gly Leu Val Gln Pro Lys Gly
  1               5                  10                  15

Ser Leu Lys Leu Ser Cys Gly Ala Ser Asp Phe Thr Phe Asn Thr Tyr
                 20                  25                  30

Ala Met His Trp Val Arg Gln Ala Pro Gly Met Ala Leu Glu Trp Val
             35                  40                  45

Ala Arg Ile Arg Thr Lys Ser Ser Asn Tyr Ala Thr Tyr Tyr Ala Asp
 50                  55                  60

Ser Val Lys Asp Arg Phe Thr Ile Ser Arg Asp Asp Ser Gln Asn Met
 65                  70                  75                  80

Leu Tyr Leu Gln Met Asn Asn Leu Lys Thr Glu Asp Thr Ala Met Tyr
                 85                  90                  95

Tyr Cys Val Arg Asp Met Gly Gln Arg Arg Gln Phe Ala Tyr Trp Gly
                100                 105                 110

Gln Gly Thr Leu Val Thr Val Ser Ala
        115                 120

<210> SEQ ID NO 11
<211> LENGTH: 112
<212> TYPE: PRT
<213> ORGANISM: Mus musculus

<400> SEQUENCE: 11

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Thr Phe
                 20                  25                  30

Asp Tyr Ser Phe Leu His Trp Tyr Gln Gln Lys Pro Gly Gln Pro Pro
             35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Tyr Thr Phe Gly Gly Gly Thr Lys Leu Glu Ile Glu Arg
                100                 105                 110

<210> SEQ ID NO 12
<211> LENGTH: 180
<212> TYPE: PRT
<213> ORGANISM: Macaca fascicularis

<400> SEQUENCE: 12
```

Met Thr Thr Glu Leu Thr Glu Lys Tyr Glu Tyr Lys Glu Gly Gln
1               5                   10                  15

Thr Leu Glu Val Lys Cys Asp Tyr Ala Leu Glu Lys Tyr Ala Asn Ser
            20                  25                  30

Arg Lys Ala Trp Gln Lys Met Glu Gly Lys Met Pro Lys Ile Leu Ala
        35                  40                  45

Lys Thr Glu Arg Pro Ser Glu Asn Ser His Pro Val Gln Val Gly Arg
50                  55                  60

Ile Thr Leu Glu Asp Tyr Pro Asp His Gly Leu Leu Gln Val Gln Met
65                  70                  75                  80

Thr Asn Leu Gln Val Glu Asp Ser Gly Leu Tyr Gln Cys Val Ile Tyr
            85                  90                  95

Gln His Pro Lys Glu Ser His Val Leu Phe Asn Pro Ile Cys Leu Val
            100                 105                 110

Val Thr Lys Gly Ser Ser Gly Thr Pro Gly Ser Ser Glu Asn Ser Thr
            115                 120                 125

Gln Asn Val Tyr Arg Thr Pro Ser Thr Thr Ala Lys Ala Leu Gly Pro
        130                 135                 140

Arg Tyr Thr Ser Pro Arg Thr Val Thr Gln Ala Pro Pro Glu Ser Thr
145                 150                 155                 160

Val Val Val Ser Thr Pro Gly Ser Glu Ile Asn Leu Thr Asn Val Thr
            165                 170                 175

Asp Ile Ile Arg
            180

<210> SEQ ID NO 13
<211> LENGTH: 206
<212> TYPE: PRT
<213> ORGANISM: Artificial sequence
<220> FEATURE:
<223> OTHER INFORMATION: K20A-hTREM-1-Cmyc2-His6

<400> SEQUENCE: 13

Ala Thr Lys Leu Thr Glu Glu Lys Tyr Glu Leu Lys Glu Gly Gln Thr
1               5                   10                  15

Leu Asp Val Ala Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
            85                  90                  95

Gln Pro Pro Lys Glu Pro His Met Leu Phe Asp Arg Ile Arg Leu Val
            100                 105                 110

Val Thr Lys Gly Phe Ser Gly Thr Pro Gly Ser Asn Glu Asn Ser Thr
            115                 120                 125

Gln Asn Val Tyr Lys Ile Pro Pro Thr Thr Lys Ala Leu Cys Pro
        130                 135                 140

Leu Tyr Thr Ser Pro Arg Thr Val Thr Gln Ala Pro Pro Lys Ser Thr
145                 150                 155                 160

Ala Asp Val Ser Thr Pro Asp Ser Glu Ile Asn Leu Thr Asn Val Thr
            165                 170                 175

Asp Ile Ile Arg Glu Gln Lys Leu Ile Ser Glu Glu Asp Leu Glu Gln
             180                 185                 190

Lys Leu Ile Ser Glu Glu Asp Leu His His His His His His
         195                 200                 205

<210> SEQ ID NO 14
<211> LENGTH: 205
<212> TYPE: PRT
<213> ORGANISM: Artificial sequence
<220> FEATURE:
<223> OTHER INFORMATION: A24/Y28F/N30S/R32Q/P70H-cTREM-1-Cmyc2-His6

<400> SEQUENCE: 14

Thr Thr Glu Leu Thr Glu Glu Lys Tyr Glu Tyr Lys Glu Gly Gln Thr
 1               5                  10                  15

Leu Glu Val Lys Cys Asp Tyr Thr Leu Glu Lys Phe Ala Ser Ser Gln
             20                  25                  30

Lys Ala Trp Gln Lys Met Glu Gly Lys Met Pro Lys Ile Leu Ala Lys
         35                  40                  45

Thr Glu Arg Pro Ser Glu Asn Ser His Pro Val Gln Val Gly Arg Ile
     50                  55                  60

Thr Leu Glu Asp Tyr His Asp His Gly Leu Leu Gln Val Gln Met Thr
65                  70                  75                  80

Asn Leu Gln Val Glu Asp Ser Gly Leu Tyr Gln Cys Val Ile Tyr Gln
                 85                  90                  95

His Pro Lys Glu Ser His Val Leu Phe Asn Pro Ile Cys Leu Val Val
            100                 105                 110

Thr Lys Gly Ser Ser Gly Thr Pro Gly Ser Ser Glu Asn Ser Thr Gln
        115                 120                 125

Asn Val Tyr Arg Thr Pro Ser Thr Thr Ala Lys Ala Leu Gly Pro Arg
    130                 135                 140

Tyr Thr Ser Pro Arg Thr Val Thr Gln Ala Pro Pro Glu Ser Thr Val
145                 150                 155                 160

Val Val Ser Thr Pro Gly Ser Glu Ile Asn Leu Thr Asn Val Thr Asp
                165                 170                 175

Ile Ile Arg Glu Gln Lys Leu Ile Ser Glu Glu Asp Leu Glu Gln Lys
            180                 185                 190

Leu Ile Ser Glu Glu Asp Leu His His His His His
        195                 200                 205

<210> SEQ ID NO 15
<211> LENGTH: 205
<212> TYPE: PRT
<213> ORGANISM: Artificial sequence
<220> FEATURE:
<223> OTHER INFORMATION: A24T/Y28F/N30S/R32Q/E54K-cTREM-1-Cmyc2-His6

<400> SEQUENCE: 15

Thr Thr Glu Leu Thr Glu Glu Lys Tyr Glu Tyr Lys Glu Gly Gln Thr
 1               5                  10                  15

Leu Glu Val Lys Cys Asp Tyr Thr Leu Glu Lys Phe Ala Ser Ser Gln
             20                  25                  30

Lys Ala Trp Gln Lys Met Glu Gly Lys Met Pro Lys Ile Leu Ala Lys
         35                  40                  45

Thr Glu Arg Pro Ser Lys Asn Ser His Pro Val Gln Val Gly Arg Ile
     50                  55                  60

Thr Leu Glu Asp Tyr Pro Asp His Gly Leu Leu Gln Val Gln Met Thr

```
                65                  70                  75                  80
Asn Leu Gln Val Glu Asp Ser Gly Leu Tyr Gln Cys Val Ile Tyr Gln
                    85                  90                  95

His Pro Lys Glu Ser His Val Leu Phe Asn Pro Ile Cys Leu Val Val
            100                 105                 110

Thr Lys Gly Ser Ser Gly Thr Pro Gly Ser Ser Glu Asn Ser Thr Gln
        115                 120                 125

Asn Val Tyr Arg Thr Pro Ser Thr Thr Ala Lys Ala Leu Gly Pro Arg
    130                 135                 140

Tyr Thr Ser Pro Arg Thr Val Thr Gln Ala Pro Pro Glu Ser Thr Val
145                 150                 155                 160

Val Val Ser Thr Pro Gly Ser Glu Ile Asn Leu Thr Asn Val Thr Asp
                165                 170                 175

Ile Ile Arg Glu Gln Lys Leu Ile Ser Glu Glu Asp Leu Glu Gln Lys
            180                 185                 190

Leu Ile Ser Glu Glu Asp Leu His His His His His
        195                 200                 205

<210> SEQ ID NO 16
<211> LENGTH: 29
<212> TYPE: DNA
<213> ORGANISM: Artificial sequence
<220> FEATURE:
<223> OTHER INFORMATION: Primer

<400> SEQUENCE: 16
tagtagggat ccgctggtgc acaggaagg                                     29

<210> SEQ ID NO 17
<211> LENGTH: 32
<212> TYPE: DNA
<213> ORGANISM: Artificial sequence
<220> FEATURE:
<223> OTHER INFORMATION: Primer

<400> SEQUENCE: 17
tagtaggcgg ccgcttcgtg ggcctagggt ac                                 32

<210> SEQ ID NO 18
<211> LENGTH: 140
<212> TYPE: PRT
<213> ORGANISM: Artificial sequence
<220> FEATURE:
<223> OTHER INFORMATION: hTREM-1-IgV-His6

<400> SEQUENCE: 18

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
                20                  25                  30

Glu Gly Gln Thr Leu Asp Val Lys Cys Asp Tyr Thr Leu Glu Lys Phe
            35                  40                  45

Ala Ser Ser Gln Lys Ala Trp Gln Ile Ile Arg Asp Gly Glu Met Pro
        50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
```

```
            100                 105                 110
Cys Val Ile Tyr Gln Pro Pro Lys Glu Pro His Met Leu Phe Asp Arg
        115                 120                 125

Ile Arg Leu Val Val Thr His His His His His
        130                 135                 140

<210> SEQ ID NO 19
<211> LENGTH: 205
<212> TYPE: PRT
<213> ORGANISM: Artificial sequence
<220> FEATURE:
<223> OTHER INFORMATION: cTREM-1-Cmyc2-His6

<400> SEQUENCE: 19

Thr Thr Glu Leu Thr Glu Glu Lys Tyr Glu Tyr Lys Glu Gly Gln Thr
1               5                   10                  15

Leu Glu Val Lys Cys Asp Tyr Ala Leu Glu Lys Tyr Ala Asn Ser Arg
            20                  25                  30

Lys Ala Trp Gln Lys Met Glu Gly Lys Met Pro Lys Ile Leu Ala Lys
        35                  40                  45

Thr Glu Arg Pro Ser Glu Asn Ser His Pro Val Gln Val Gly Arg Ile
50                  55                  60

Thr Leu Glu Asp Tyr Pro Asp His Gly Leu Leu Gln Val Gln Met Thr
65                  70                  75                  80

Asn Leu Gln Val Glu Asp Ser Gly Leu Tyr Gln Cys Val Ile Tyr Gln
                85                  90                  95

His Pro Lys Glu Ser His Val Leu Phe Asn Pro Ile Cys Leu Val Val
            100                 105                 110

Thr Lys Gly Ser Ser Gly Thr Pro Gly Ser Ser Glu Asn Ser Thr Gln
        115                 120                 125

Asn Val Tyr Arg Thr Pro Ser Thr Thr Ala Lys Ala Leu Gly Pro Arg
    130                 135                 140

Tyr Thr Ser Pro Arg Thr Val Thr Gln Ala Pro Pro Glu Ser Thr Val
145                 150                 155                 160

Val Val Ser Thr Pro Gly Ser Glu Ile Asn Leu Thr Asn Val Thr Asp
                165                 170                 175

Ile Ile Arg Glu Gln Lys Leu Ile Ser Glu Glu Asp Leu Glu Gln Lys
            180                 185                 190

Leu Ile Ser Glu Glu Asp Leu His His His His His
        195                 200                 205

<210> SEQ ID NO 20
<211> LENGTH: 206
<212> TYPE: PRT
<213> ORGANISM: Artificial sequence
<220> FEATURE:
<223> OTHER INFORMATION: hTREM-1-Cmyc2-His6

<400> SEQUENCE: 20

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
50                  55                  60
```

```
Ile Ile Leu Glu Asp Tyr His Asp His Gly Leu Arg Val Arg Met
 65                  70                  75                  80

Val Asn Leu Gln Val Glu Asp Ser Gly Leu Tyr Gln Cys Val Ile Tyr
                 85                  90                  95

Gln Pro Pro Lys Glu Pro His Met Leu Phe Asp Arg Ile Arg Leu Val
                100                 105                 110

Val Thr Lys Gly Phe Ser Gly Thr Pro Gly Ser Asn Glu Asn Ser Thr
            115                 120                 125

Gln Asn Val Tyr Lys Ile Pro Pro Thr Thr Lys Ala Leu Cys Pro
        130                 135                 140

Leu Tyr Thr Ser Pro Arg Thr Val Thr Gln Ala Pro Pro Lys Ser Thr
145                 150                 155                 160

Ala Asp Val Ser Thr Pro Asp Ser Glu Ile Asn Leu Thr Asn Val Thr
                165                 170                 175

Asp Ile Ile Arg Glu Gln Lys Leu Ile Ser Glu Glu Asp Leu Glu Gln
                180                 185                 190

Lys Leu Ile Ser Glu Glu Asp Leu His His His His His His
            195                 200                 205
```

<210> SEQ ID NO 21
<211> LENGTH: 233
<212> TYPE: PRT
<213> ORGANISM: Macaca fascicularis

<400> SEQUENCE: 21

```
Met Arg Lys Thr Arg Leu Trp Gly Leu Leu Trp Met Leu Phe Val Ser
 1               5                  10                  15

Glu Leu Arg Ala Thr Thr Glu Leu Thr Glu Glu Lys Tyr Glu Tyr Lys
                 20                  25                  30

Glu Gly Gln Thr Leu Glu Val Lys Cys Asp Tyr Ala Leu Glu Lys Tyr
            35                  40                  45

Ala Asn Ser Arg Lys Ala Trp Gln Lys Met Glu Gly Lys Met Pro Lys
 50                  55                  60

Ile Leu Ala Lys Thr Glu Arg Pro Ser Glu Asn Ser His Pro Val Gln
 65                  70                  75                  80

Val Gly Arg Ile Thr Leu Glu Asp Tyr Pro Asp His Gly Leu Leu Gln
                 85                  90                  95

Val Gln Met Thr Asn Leu Gln Val Glu Asp Ser Gly Leu Tyr Gln Cys
                100                 105                 110

Val Ile Tyr Gln His Pro Lys Glu Ser His Val Leu Phe Asn Pro Ile
            115                 120                 125

Cys Leu Val Val Thr Lys Gly Ser Gly Thr Pro Gly Ser Ser Glu
130                 135                 140

Asn Ser Thr Gln Asn Val Tyr Arg Thr Pro Ser Thr Thr Ala Lys Ala
145                 150                 155                 160

Leu Gly Pro Arg Tyr Thr Ser Pro Arg Thr Val Thr Gln Ala Pro Pro
                165                 170                 175

Glu Ser Thr Val Val Ser Thr Pro Gly Ser Glu Ile Asn Leu Thr
            180                 185                 190

Asn Val Thr Asp Ile Ile Arg Val Pro Val Phe Asn Ile Val Ile Ile
        195                 200                 205

Val Ala Gly Gly Phe Leu Ser Lys Ser Leu Val Phe Ser Val Leu Phe
    210                 215                 220

Ala Val Thr Leu Arg Ser Phe Gly Pro
225                 230
```

<210> SEQ ID NO 22
<211> LENGTH: 230
<212> TYPE: PRT
<213> ORGANISM: Mus musculus

<400> SEQUENCE: 22

Met Arg Lys Ala Gly Leu Trp Gly Leu Leu Cys Val Phe Phe Val Ser
1               5                   10                  15

Glu Val Lys Ala Ala Ile Val Leu Glu Glu Arg Tyr Asp Leu Val
            20                  25                  30

Glu Gly Gln Thr Leu Thr Val Lys Cys Pro Phe Asn Ile Met Lys Tyr
        35                  40                  45

Ala Asn Ser Gln Lys Ala Trp Gln Arg Leu Pro Asp Gly Lys Glu Pro
    50                  55                  60

Leu Thr Leu Val Val Thr Gln Arg Pro Phe Thr Arg Pro Ser Glu Val
65                  70                  75                  80

His Met Gly Lys Phe Thr Leu Lys His Asp Pro Ser Glu Ala Met Leu
                85                  90                  95

Gln Val Gln Met Thr Asp Leu Gln Val Thr Asp Ser Gly Leu Tyr Arg
            100                 105                 110

Cys Val Ile Tyr His Pro Pro Asn Asp Pro Val Val Leu Phe His Pro
        115                 120                 125

Val Arg Leu Val Val Thr Lys Gly Ser Ser Asp Val Phe Thr Pro Val
    130                 135                 140

Ile Ile Pro Ile Thr Arg Leu Thr Glu Arg Pro Ile Leu Ile Thr Thr
145                 150                 155                 160

Lys Tyr Ser Pro Ser Asp Thr Thr Thr Arg Ser Leu Pro Lys Pro
                165                 170                 175

Thr Ala Val Val Ser Ser Pro Gly Leu Gly Val Thr Ile Ile Asn Gly
            180                 185                 190

Thr Asp Ala Asp Ser Val Ser Ser Ser Val Thr Ile Ser Val Ile
        195                 200                 205

Cys Gly Leu Leu Ser Lys Ser Leu Val Phe Ile Ile Leu Phe Ile Val
    210                 215                 220

Thr Lys Arg Thr Phe Gly
225                 230

<210> SEQ ID NO 23
<211> LENGTH: 175
<212> TYPE: PRT
<213> ORGANISM: Homo sapiens

<400> SEQUENCE: 23

Gln Glu Thr Glu Asp Pro Ala Cys Cys Ser Pro Ile Val Pro Arg Asn
1               5                   10                  15

Glu Trp Lys Ala Leu Ala Ser Glu Cys Ala Gln His Leu Ser Leu Pro
            20                  25                  30

Leu Arg Tyr Val Val Val Ser His Thr Ala Gly Ser Ser Cys Asn Thr
        35                  40                  45

Pro Ala Ser Cys Gln Gln Gln Ala Arg Asn Val Gln His Tyr His Met
    50                  55                  60

Lys Thr Leu Gly Trp Cys Asp Val Gly Tyr Asn Phe Leu Ile Gly Glu
65                  70                  75                  80

Asp Gly Leu Val Tyr Glu Gly Arg Gly Trp Asn Phe Thr Gly Ala His
                85                  90                  95

```
Ser Gly His Leu Trp Asn Pro Met Ser Ile Gly Ile Ser Phe Met Gly
            100             105             110

Asn Tyr Met Asp Arg Val Pro Thr Pro Gln Ala Ile Arg Ala Ala Gln
        115             120             125

Gly Leu Leu Ala Cys Gly Val Ala Gln Gly Ala Leu Arg Ser Asn Tyr
    130             135             140

Val Leu Lys Gly His Arg Asp Val Gln Arg Thr Leu Ser Pro Gly Asn
145             150             155             160

Gln Leu Tyr His Leu Ile Gln Asn Trp Pro His Tyr Arg Ser Pro
                165             170             175
```